United States Patent
Ong et al.

(10) Patent No.: US 9,833,453 B2
(45) Date of Patent: Dec. 5, 2017

(54) THERAPEUTIC COMPOUNDS AND USES THEREOF

(71) Applicant: Kala Pharmaceuticals, Inc., Waltham, MA (US)

(72) Inventors: Winston Zapanta Ong, Waltham, MA (US); Pawel Wojciech Nowak, Waltham, MA (US); Ben C. Askew, Marshfield, MA (US); Jinsoo Kim, Waltham, MA (US)

(73) Assignee: Kala Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 15/139,121

(22) Filed: Apr. 26, 2016

(65) Prior Publication Data
US 2016/0235753 A1    Aug. 18, 2016

Related U.S. Application Data

(63) Continuation of application No. 14/184,886, filed on Feb. 20, 2014, now Pat. No. 9,353,123.

(60) Provisional application No. 61/767,087, filed on Feb. 20, 2013, provisional application No. 61/898,741, filed on Nov. 1, 2013.

(51) Int. Cl.
| | | |
|---|---|---|
| C07D 491/107 | (2006.01) | |
| A61K 31/517 | (2006.01) | |
| C07D 403/12 | (2006.01) | |
| A61K 9/00 | (2006.01) | |
| C07D 519/00 | (2006.01) | |

(52) U.S. Cl.
CPC .......... *A61K 31/517* (2013.01); *A61K 9/0048* (2013.01); *C07D 403/12* (2013.01); *C07D 491/107* (2013.01); *C07D 519/00* (2013.01)

(58) Field of Classification Search
CPC .................................................. C07D 491/07
See application file for complete search history.

(56) References Cited

U.S. PATENT DOCUMENTS

| | | |
|---|---|---|
| 4,910,225 A | 3/1990 | Ogawa et al. |
| 4,996,335 A | 2/1991 | Bodor |
| 5,190,956 A | 3/1993 | Afonso et al. |
| 5,364,884 A | 11/1994 | Varma et al. |
| 5,442,039 A | 8/1995 | Hefner, Jr. et al. |
| 5,486,512 A | 1/1996 | Gregor |
| 5,518,187 A | 5/1996 | Bruno et al. |
| 5,534,259 A | 7/1996 | Zalipsky et al. |
| 5,580,870 A | 12/1996 | Barker et al. |
| 5,718,388 A | 2/1998 | Czekai et al. |
| 5,747,061 A | 5/1998 | Amselem et al. |
| 5,773,476 A | 6/1998 | Chen et al. |
| 5,862,999 A | 1/1999 | Czekai et al. |
| 5,922,357 A | 7/1999 | Coombes et al. |
| 6,046,208 A | 4/2000 | Adams et al. |
| 6,106,819 A | 8/2000 | Sucher |
| 6,153,607 A | 11/2000 | Pflugfelder et al. |
| 6,153,617 A | 11/2000 | Bridges |
| 6,165,509 A | 12/2000 | Hoffman et al. |
| 6,197,346 B1 | 3/2001 | Mathiowitz et al. |
| 6,217,908 B1 | 4/2001 | Mathiowitz et al. |

(Continued)

FOREIGN PATENT DOCUMENTS

| | | |
|---|---|---|
| CA | 2564982 A1 | 11/2005 |
| CN | 1724521 A | 1/2006 |

(Continued)

OTHER PUBLICATIONS

U.S. Appl. No. 15/139,135, filed Apr. 26, 2016.*

(Continued)

*Primary Examiner* — Paul V Ward
(74) *Attorney, Agent, or Firm* — K&L Gates LLP; Louis C. Cullman; Michelle Glasky Bergman

(57) ABSTRACT

Described herein are compounds of Formula (I)-(III), pharmaceutically acceptable salts thereof, and pharmaceutical compositions thereof. Also provided are particles (e.g., nanoparticles) comprising compounds of Formula (I)-(III) and pharmaceutical compositions thereof that are mucus penetrating. Methods of using the compounds or pharmaceutical compositions thereof for treating and/or preventing diseases are also provided.

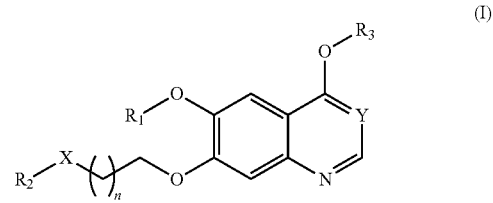

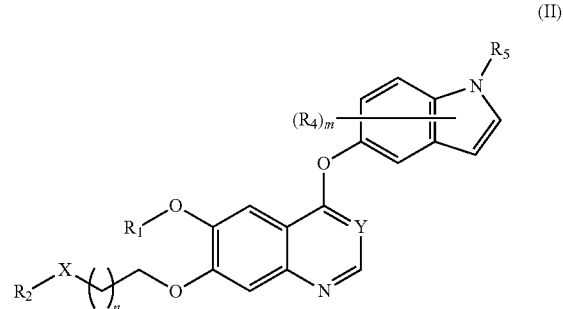

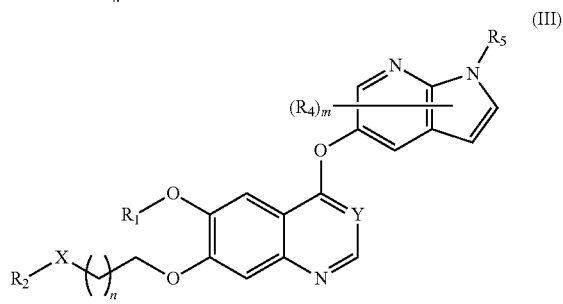

25 Claims, No Drawings

(56) References Cited

U.S. PATENT DOCUMENTS

| | | | |
|---|---|---|---|
| 6,235,313 B1 | 5/2001 | Mathiowitz et al. | |
| 6,264,981 B1 | 7/2001 | Zhang et al. | |
| 6,288,082 B1 | 9/2001 | Wissner et al. | |
| 6,365,187 B2 | 4/2002 | Mathiowitz et al. | |
| 6,372,246 B1 | 4/2002 | Wei et al. | |
| 6,627,228 B1 | 9/2003 | Milstein et al. | |
| 6,706,289 B2 | 3/2004 | Lewis et al. | |
| 7,153,524 B2 | 12/2006 | Yoshihara et al. | |
| 7,262,201 B1 | 8/2007 | Hennequin et al. | |
| 7,268,230 B2* | 9/2007 | Hennequin | C07D 401/14 544/284 |
| 7,534,449 B2 | 5/2009 | Saltzman et al. | |
| 7,550,441 B2 | 6/2009 | Farokhzad et al. | |
| 7,795,237 B2 | 9/2010 | Ahmed et al. | |
| 7,842,232 B2 | 11/2010 | Bosch et al. | |
| 7,906,136 B2 | 3/2011 | Wong et al. | |
| 7,989,460 B2* | 8/2011 | Hennequin | C07D 401/14 514/266.1 |
| 8,293,902 B2 | 10/2012 | Hennequin | |
| 8,492,560 B2 | 7/2013 | Stokes et al. | |
| 9,353,122 B2* | 5/2016 | Ong | C07D 491/107 |
| 2001/0000521 A1 | 4/2001 | Bigg et al. | |
| 2002/0013322 A1 | 1/2002 | Smith et al. | |
| 2002/0026052 A1 | 2/2002 | Boschelli et al. | |
| 2002/0107392 A1 | 8/2002 | Renhowe et al. | |
| 2002/0147205 A1 | 10/2002 | Carter et al. | |
| 2003/0032624 A1 | 2/2003 | Yang | |
| 2003/0055049 A1 | 3/2003 | Kath et al. | |
| 2003/0092721 A1 | 5/2003 | Pitts et al. | |
| 2003/0092908 A1 | 5/2003 | Pitts et al. | |
| 2003/0100573 A1 | 5/2003 | Wang et al. | |
| 2003/0114452 A1 | 6/2003 | Adams et al. | |
| 2003/0114486 A1 | 6/2003 | Metcalf et al. | |
| 2003/0181472 A1 | 9/2003 | Clark et al. | |
| 2003/0199491 A1 | 10/2003 | Hennequin | |
| 2003/0212276 A1 | 11/2003 | Boschelli et al. | |
| 2004/0063955 A1 | 4/2004 | Biediger et al. | |
| 2004/0092535 A1 | 5/2004 | Barsanti et al. | |
| 2004/0235848 A1 | 11/2004 | Okuzumi et al. | |
| 2005/0009809 A1 | 1/2005 | Gerlach et al. | |
| 2005/0009815 A1 | 1/2005 | DeVita et al. | |
| 2005/0026915 A1 | 2/2005 | DeVita et al. | |
| 2005/0038050 A1 | 2/2005 | Moore et al. | |
| 2005/0054662 A1 | 3/2005 | Hennequin et al. | |
| 2005/0058603 A1 | 3/2005 | Gao et al. | |
| 2005/0085465 A1 | 4/2005 | Hennequin et al. | |
| 2005/0101617 A1 | 5/2005 | Wallace et al. | |
| 2005/0124562 A1 | 6/2005 | Guiles et al. | |
| 2005/0137395 A1 | 6/2005 | Hong et al. | |
| 2005/0137399 A1 | 6/2005 | Cai et al. | |
| 2005/0148607 A1 | 7/2005 | Suzuki et al. | |
| 2005/0187247 A1 | 8/2005 | Berger et al. | |
| 2005/0191359 A1 | 9/2005 | Goldshtein et al. | |
| 2005/0239825 A1 | 10/2005 | Heise et al. | |
| 2005/0245547 A1 | 11/2005 | Kim et al. | |
| 2005/0256157 A1 | 11/2005 | Gesner et al. | |
| 2005/0261307 A1 | 11/2005 | Cai et al. | |
| 2005/0266067 A1 | 12/2005 | Sengupta | |
| 2005/0266090 A1 | 12/2005 | Prokop | |
| 2005/0282802 A1 | 12/2005 | Kostik et al. | |
| 2006/0004017 A1 | 1/2006 | Stokes et al. | |
| 2006/0025406 A1 | 2/2006 | Zembower et al. | |
| 2006/0058325 A1 | 3/2006 | Mortlock | |
| 2006/0058523 A1 | 3/2006 | Mortlock et al. | |
| 2006/0079515 A1 | 4/2006 | Frost | |
| 2006/0116357 A1 | 6/2006 | Heron et al. | |
| 2006/0167026 A1 | 7/2006 | Nawa et al. | |
| 2006/0223783 A1 | 10/2006 | Xu et al. | |
| 2006/0241115 A1 | 10/2006 | Potashman et al. | |
| 2006/0252777 A1 | 11/2006 | Kim et al. | |
| 2006/0257487 A1 | 11/2006 | Owen et al. | |
| 2006/0264460 A1 | 11/2006 | Green et al. | |
| 2006/0270668 A1 | 11/2006 | Chew et al. | |
| 2006/0270669 A1 | 11/2006 | Chew et al. | |
| 2007/0032518 A1 | 2/2007 | Norman et al. | |
| 2007/0054916 A1 | 3/2007 | Patel et al. | |
| 2007/0059552 A1 | 3/2007 | Takeda et al. | |
| 2007/0060608 A1 | 3/2007 | Vanderslice et al. | |
| 2007/0060613 A1 | 3/2007 | Kim | |
| 2007/0093432 A1 | 4/2007 | Yang | |
| 2007/0149480 A1 | 6/2007 | Ghosh et al. | |
| 2007/0149523 A1 | 6/2007 | Ehlert et al. | |
| 2007/0178051 A1 | 8/2007 | Pruitt et al. | |
| 2007/0196860 A1 | 8/2007 | Gee et al. | |
| 2007/0213319 A1 | 9/2007 | Zembower et al. | |
| 2007/0231821 A1 | 10/2007 | Bupp et al. | |
| 2007/0299044 A1 | 12/2007 | Farng | |
| 2008/0027099 A1 | 1/2008 | Govek et al. | |
| 2008/0096193 A1 | 4/2008 | Bupp et al. | |
| 2008/0125448 A1 | 5/2008 | Qian et al. | |
| 2008/0153799 A1 | 6/2008 | Laurent et al. | |
| 2008/0159984 A1 | 7/2008 | Ben-Sasson | |
| 2008/0175887 A1 | 7/2008 | Wang | |
| 2008/0194468 A1 | 8/2008 | Bodor | |
| 2008/0200464 A1 | 8/2008 | Bellon et al. | |
| 2008/0221161 A1 | 9/2008 | Pinkerton et al. | |
| 2008/0248125 A1 | 10/2008 | Irache Garreta et al. | |
| 2008/0267876 A1 | 10/2008 | Benita et al. | |
| 2008/0280917 A1 | 11/2008 | Albrecht et al. | |
| 2008/0306053 A1 | 12/2008 | Tachdjian et al. | |
| 2008/0312232 A1 | 12/2008 | Kim et al. | |
| 2008/0318943 A1 | 12/2008 | Chang et al. | |
| 2009/0036474 A1 | 2/2009 | Ple | |
| 2009/0047244 A1 | 2/2009 | Parsy et al. | |
| 2009/0062279 A1 | 3/2009 | Marsais et al. | |
| 2009/0062337 A1 | 3/2009 | Schwan et al. | |
| 2009/0076044 A1 | 3/2009 | Qian et al. | |
| 2009/0087493 A1 | 4/2009 | Dai et al. | |
| 2009/0105211 A1 | 4/2009 | Bahceci et al. | |
| 2009/0131461 A1 | 5/2009 | Davidson et al. | |
| 2009/0221591 A1 | 9/2009 | Hartmann et al. | |
| 2009/0253148 A1 | 10/2009 | Piper et al. | |
| 2010/0015136 A1 | 1/2010 | Michel et al. | |
| 2010/0048447 A1 | 2/2010 | Haetzelt et al. | |
| 2010/0056506 A1 | 3/2010 | Huang et al. | |
| 2010/0076045 A1 | 3/2010 | Castillo | |
| 2010/0168149 A1 | 7/2010 | Lavielle et al. | |
| 2010/0204234 A1 | 8/2010 | Hartmann et al. | |
| 2010/0222308 A1 | 9/2010 | Zhang | |
| 2010/0226931 A1 | 9/2010 | Valiante et al. | |
| 2010/0290983 A1 | 11/2010 | Rabinow et al. | |
| 2011/0053931 A1 | 3/2011 | Gaudino et al. | |
| 2011/0104161 A1 | 5/2011 | Burgess et al. | |
| 2011/0166168 A1 | 7/2011 | Buchmann et al. | |
| 2011/0172186 A1 | 7/2011 | Behnke et al. | |
| 2011/0275643 A1 | 11/2011 | Liou et al. | |
| 2011/0306572 A1 | 12/2011 | Estok et al. | |
| 2011/0319403 A1 | 12/2011 | Zhou et al. | |
| 2012/0021897 A1 | 1/2012 | Iwata et al. | |
| 2012/0121718 A1 | 5/2012 | Lai et al. | |
| 2012/0214803 A1 | 8/2012 | Buhr et al. | |
| 2012/0225875 A1 | 9/2012 | Jonczyk et al. | |
| 2012/0232110 A1 | 9/2012 | Moy et al. | |
| 2012/0252756 A1 | 10/2012 | Coffey | |
| 2012/0264715 A1 | 10/2012 | Takeuchi et al. | |
| 2012/0264730 A1 | 10/2012 | Takeuchi et al. | |
| 2012/0264732 A1 | 10/2012 | Takeuchi et al. | |
| 2012/0289486 A1 | 11/2012 | Bodor | |
| 2012/0292571 A1 | 11/2012 | Buesing et al. | |
| 2012/0305852 A1 | 12/2012 | Anemian et al. | |
| 2013/0102603 A1 | 4/2013 | Dorsch et al. | |
| 2013/0109713 A1 | 5/2013 | Lavoie et al. | |
| 2013/0116279 A1 | 5/2013 | Govek et al. | |
| 2013/0123344 A1 | 5/2013 | Kristie et al. | |
| 2013/0210844 A1 | 8/2013 | Gharat et al. | |
| 2013/0245032 A1 | 9/2013 | Chen et al. | |
| 2013/0281402 A1 | 10/2013 | Chen et al. | |
| 2013/0324570 A1 | 12/2013 | Hansen et al. | |
| 2013/0344165 A1 | 12/2013 | Boden et al. | |
| 2014/0024661 A1 | 1/2014 | Zhou et al. | |
| 2014/0142137 A1 | 5/2014 | Cohen et al. | |
| 2014/0163037 A1 | 6/2014 | Guenther et al. | |
| 2014/0228361 A1 | 8/2014 | Zhang et al. | |
| 2014/0235548 A1 | 8/2014 | Zhou et al. | |

(56) References Cited

U.S. PATENT DOCUMENTS

| | | |
|---|---|---|
| 2014/0235657 A1 | 8/2014 | Ong et al. |
| 2014/0239281 A1 | 8/2014 | Ise et al. |
| 2014/0294764 A1 | 10/2014 | Yoon et al. |
| 2014/0294973 A1 | 10/2014 | Kan et al. |
| 2014/0296136 A1 | 10/2014 | Rudd et al. |
| 2014/0315886 A1 | 10/2014 | Suzuki et al. |
| 2016/0237094 A1 | 8/2016 | Ong et al. |

FOREIGN PATENT DOCUMENTS

| | | |
|---|---|---|
| CN | 1955183 A | 5/2007 |
| CN | 101012224 A | 8/2007 |
| CN | 101012225 A | 8/2007 |
| CN | 101108846 A | 1/2008 |
| CN | 101747306 B | 8/2012 |
| CN | 103304572 A | 9/2013 |
| CN | 103804292 A | 5/2014 |
| CN | 103102342 B | 10/2014 |
| CN | 103102345 B | 6/2015 |
| DE | 102005009705 A1 | 9/2006 |
| EP | 0837063 A1 | 4/1998 |
| EP | 1021414 B1 | 6/2003 |
| EP | 1117659 B1 | 12/2003 |
| EP | 0692510 | 12/2004 |
| EP | 1785420 A1 | 5/2007 |
| EP | 1268431 B1 | 8/2007 |
| EP | 1744759 B1 | 9/2009 |
| EP | 2127655 A1 | 12/2009 |
| EP | 2010496 B1 | 8/2010 |
| EP | 2335686 A1 | 6/2011 |
| EP | 2247579 B1 | 4/2012 |
| GB | 2345486 A | 7/2000 |
| JP | 2008214323 A | 9/2008 |
| JP | 2011178753 A | 9/2011 |
| KR | 20140072295 A | 6/2014 |
| KR | 20140103391 A | 8/2014 |
| KR | 20140105634 A | 9/2014 |
| WO | 9503356 A1 | 2/1995 |
| WO | 9522318 A1 | 8/1995 |
| WO | 97/03069 A1 | 1/1997 |
| WO | 9703069 A1 | 1/1997 |
| WO | 9720578 A1 | 6/1997 |
| WO | 9744013 A1 | 11/1997 |
| WO | 9829097 A1 | 7/1998 |
| WO | 9830545 A1 | 7/1998 |
| WO | 9831346 A1 | 7/1998 |
| WO | 9901498 A1 | 1/1999 |
| WO | 0018761 A1 | 4/2000 |
| WO | 00/42026 A1 | 7/2000 |
| WO | 0042026 | 7/2000 |
| WO | 0046147 A2 | 8/2000 |
| WO | 0051991 A1 | 9/2000 |
| WO | 0055141 A1 | 9/2000 |
| WO | 0068199 A1 | 11/2000 |
| WO | 0068200 A1 | 11/2000 |
| WO | 0172711 A1 | 10/2001 |
| WO | 0194341 A1 | 12/2001 |
| WO | 0218372 A1 | 3/2002 |
| WO | 0222618 A1 | 3/2002 |
| WO | 0238127 A2 | 5/2002 |
| WO | 02053189 A2 | 7/2002 |
| WO | 02/060868 A2 | 8/2002 |
| WO | 02060868 A2 | 8/2002 |
| WO | 02076976 A2 | 10/2002 |
| WO | 02092571 A1 | 11/2002 |
| WO | 02100874 A1 | 12/2002 |
| WO | 03000237 A2 | 1/2003 |
| WO | 03051906 A3 | 11/2003 |
| WO | 2004/046101 A2 | 6/2004 |
| WO | 2004046101 A2 | 6/2004 |
| WO | 2005007643 A1 | 1/2005 |
| WO | 2005035521 A1 | 4/2005 |
| WO | 2005072710 A2 | 8/2005 |
| WO | 2005094836 A2 | 10/2005 |
| WO | 2005105146 A1 | 11/2005 |
| WO | 2005097134 A3 | 1/2006 |
| WO | 2005097137 A3 | 2/2006 |
| WO | 2006030941 A1 | 3/2006 |
| WO | 2006044660 A2 | 4/2006 |
| WO | 2006063249 A2 | 6/2006 |
| WO | 2006/089150 A2 | 8/2006 |
| WO | 2006089150 A2 | 8/2006 |
| WO | 2006094808 A2 | 9/2006 |
| WO | 2006117570 A1 | 11/2006 |
| WO | 2007015569 A1 | 2/2007 |
| WO | 2007015578 A1 | 2/2007 |
| WO | 2007104696 A1 | 9/2007 |
| WO | 2007107318 A1 | 9/2007 |
| WO | 2007119046 A1 | 10/2007 |
| WO | 2007/133211 A1 | 11/2007 |
| WO | 2007133211 A1 | 11/2007 |
| WO | 2007133808 A2 | 11/2007 |
| WO | 2008001956 A1 | 1/2008 |
| WO | 2008030557 A2 | 3/2008 |
| WO | 2008033924 A1 | 3/2008 |
| WO | 2008020302 A3 | 4/2008 |
| WO | 2008/056148 A1 | 5/2008 |
| WO | 2008056148 A1 | 5/2008 |
| WO | 2008113161 A1 | 9/2008 |
| WO | 2008124632 A1 | 10/2008 |
| WO | 2008053221 A3 | 12/2008 |
| WO | 2009030224 A2 | 3/2009 |
| WO | 2008041960 A3 | 5/2009 |
| WO | 2009089851 A1 | 7/2009 |
| WO | 2009094211 A1 | 7/2009 |
| WO | 2010021918 A1 | 2/2010 |
| WO | 2010056758 A1 | 5/2010 |
| WO | 2010/102811 A1 | 9/2010 |
| WO | 2010102811 A1 | 9/2010 |
| WO | 2011106168 A1 | 9/2011 |
| WO | 2011106702 A2 | 9/2011 |
| WO | 2011157428 A2 | 12/2011 |
| WO | 2011159328 A1 | 12/2011 |
| WO | 2012013884 A2 | 2/2012 |
| WO | 2012014114 A1 | 2/2012 |
| WO | 2012/025237 A1 | 3/2012 |
| WO | 2012025237 A1 | 3/2012 |
| WO | 2012038942 A1 | 3/2012 |
| WO | 2012038943 A1 | 3/2012 |
| WO | 2012038944 A1 | 3/2012 |
| WO | 2012039979 A2 | 3/2012 |
| WO | 2012054923 A2 | 4/2012 |
| WO | 2012040499 A3 | 5/2012 |
| WO | 2012059158 A1 | 5/2012 |
| WO | 2012061703 A1 | 5/2012 |
| WO | 2012071042 A1 | 5/2012 |
| WO | 2012074980 A2 | 6/2012 |
| WO | 2012088431 A1 | 6/2012 |
| WO | 2012088469 A1 | 6/2012 |
| WO | 2012093117 A1 | 7/2012 |
| WO | 2012109363 A2 | 8/2012 |
| WO | 2012127506 A1 | 9/2012 |
| WO | 2012149228 A1 | 11/2012 |
| WO | 2012155062 A1 | 11/2012 |
| WO | 2012162698 A1 | 11/2012 |
| WO | 2013013614 A1 | 1/2013 |
| WO | 2013040347 A1 | 3/2013 |
| WO | 2013061269 A1 | 5/2013 |
| WO | 2013065028 A1 | 5/2013 |
| WO | 2013090804 A2 | 6/2013 |
| WO | 2013097753 A1 | 7/2013 |
| WO | 2013120057 A1 | 8/2013 |
| WO | 2013158928 A3 | 12/2013 |
| WO | 2013179144 A3 | 3/2014 |
| WO | 2013188813 A3 | 3/2014 |
| WO | 2014074517 A1 | 5/2014 |
| WO | 2014074848 A1 | 5/2014 |
| WO | 2014074926 A1 | 5/2014 |
| WO | 2014086284 A1 | 6/2014 |
| WO | 2014094962 A3 | 9/2014 |
| WO | 2014134705 A1 | 9/2014 |
| WO | 2014147611 A1 | 9/2014 |
| WO | 2014159837 A1 | 10/2014 |
| WO | 2014111269 A3 | 11/2014 |

(56) References Cited

FOREIGN PATENT DOCUMENTS

| | | | |
|---|---|---|---|
| WO | 2014182954 A1 | 11/2014 | |
| WO | 2014186398 A1 | 11/2014 | |
| WO | 2014141057 A3 | 2/2015 | |
| WO | 2014141110 A3 | 4/2015 | |

OTHER PUBLICATIONS

Vila et al., "Transport of PLA-PEG particles across the nasal mucosa: effect of particle size and PEG coating density", Journal of Controlled Release, (2004), vol. 98, pp. 231-244.
Wang et al., "Addressing the PEG Mucoadhesivity Paradox to Engineer Nanoparticles that "Slip" through the Human Mucus Barrier", Angew. Chem. Int. Ed., (2008), vol. 47, pp. 1-5.
Wang et al., "Mucoadhesive Nanoparticles May Disrupt the Protective Human Mucus Barrier by Altering Its Microstructure", PLoS ONE, (Jun. 2011), vol. 6, Issue 6, pp. 1-7.
Webster's Ninth New Collegiate Dictionary, (1988), pp. 58.
Whaley et al., "Novel Approaches to Vaginal Delivery and Safety of Microbicides: Biopharmaceuticals, Nanoparticles, and Vaccines", Antiviral Research, (2010), vol. 885, pp. S55-S66.
Wu et al., "Novel Nanoparticles Formed via Self-Assembly of Poly(ethylene glycol-b-sebacic anhydride) and Their Degradation in Water", Macromolecules, (2000), vol. 33, pp. 9040-9043.
Xu et al., "Nanoparticle diffusion in, and microrheology of, the bovine vitreous ex vivo", Journal of Controlled Release, (2013), vol. 167, pp. 76-84.
Xu et al., "Scalable method to produce biodegradable nanoparticles that rapidly penetrate human mucus", Journal of Controlled Release, (2013), vol. 170, pp. 279-286.
Yamagata et al., Improvement of the Oral Drug Absorption of Topotecan through the Inhibition of Intestinal Xenobiotic Efflux Transporter, Breast Cancer Resistance Protein, by Excipients, 35(7) Drug Metabolism and Disposition 1142-1148 (2007).
Yang et al., "Biodegradable Nanoparticles Composed Entirely of Safe Materials that Rapible Penetrate Human Mucus", Angew. Chem. Int. Ed., (2011), vol. 50, pp. 2597-2600.
Yoncheva et al., "Bioadhesive properties of pegylated nanoparticles", Expert Opin. Drug Deliv., (2005), vol. 2, No. 2, pp. 205-218.
Yoncheva et al., "Evaluation of bioadhesive potential and intestinal transport of pegylated poly(anhydride) nanoparticles", International Journal of Pharmaceutics, (2007), vol. 334, pp. 156-165.
Yoo et al., "Biodegradable Nanoparticles Containing Doxorubicin-PLGA Conjugate for Sustained Release", Pharmaceutical Research, (1999), vol. 16, No. 7, pp. 1114-1118.
Yu et al., "Biodegradable mucus-penetrating nanoparticles composed of diblock copolymers of polyethylene glycol and poly(lactic-co-glycolic acid)", Drug Deliv. and Transl. Res., (2012), vol. 2, pp. 124-128.
"Lutrol® L and Lutrol F-Grades", Pharma Ingredients & Services, (Apr. 2010), 8 pages.
Abelson et al., "Loteprednol Etabonate in the Management of Dry Eye Inflammation", Refractive eyecare for ophthalmologists, (Nov. 2000), vol. 4, No. 11, pp. 4-7.
Albertsson et al, "Synthesis, Characterization and Degradation of Aliphatic Polyanhydrides", British Polymer Journal, (1990), vol. 23, No. 3, pp. 205-212.
Alexandridis, "Poly(ethylene oxide)/poly(propylene oxide) block copolymer surfactants", Current Opinion in Colloid & Interface Science, (Oct. 1997), vol. 2, Issue 5, pp. 478-489.
Apgar et al., "Multiple-Particle Tracking Measurements of the Heterogeneities in Solutions of Actin Filaments and Actin Bundles", Biophysical Journal, (Aug. 2000), vol. 79, No. 2, pp. 1095-1106.
Batrakove et al., "Pluronic Block Copolymers: Evolution of Drug Delivery Concept from Inert Nanocarriers to Biological Response Modifiers", J. Control Release, (Sep. 10, 2008), vol. 130, No. 2, 25 pages.

Bhalla, "Microtubule-targeted anticancer agents and apoptosis", Oncogene, (2003), vol. 22, pp. 9075-9086.
Bin Choy et al., "Mucoadhesive Microparticles Engineered for Ophthalmic Drug Delivery", J. Phys. Chem Solids, (May 2008), vol. 69, No. 5-6, 8 pages.
Boskey et al., "A Self-Sampling Method to Obtain Large Volumes of Undiluted Cervicovaginal Secretions", Sexually Transmitted Diseases, (Feb. 2003), vol. 30, No. 2, pp. 107-109.
Boylan et al., "Enhancement of airway gene transfer by DNA nanoparticles using a pH-responsive block copolymer glycol and poly-L-lysine", Biomaterials, (2012) vol. 33, pp. 2361-2371.
Boylan et al., "Highly compacted DNA nanoparticles with low MW PEG coatings: In vitro, ex vivo and in vivo evaluation", Journal of Controlled Release, (2012), vol. 157, pp. 72-79.
Brorson et al., "Mutational Analysis of Avidity and Fine Specificity of Anti-Levan Antibodies", The Journal of Immunology, (1999), pp. 6694-6701.
Brummell et al., "Probing the Combining Site of an Anti-Carbohydrate Antibody by Saturation-Mutagenesis: Role of the Heavy-Chain CDR3 Residues", Biochemistry, (1993), vol. 32, No. 4, pp. 1180-1187.
Bures et al., "Surface modifications and molecular imprinting of polymers in medical and pharmaceutical applications", Journal of Controlled Release, (2001), vol. 72, pp. 25-33.
Burks et al., "In vitro scanning saturation mutagenesis of an antibody binding pocket", Proc. Natl. Acad. Sci. USA, (Jan. 1997), vol. 94, pp. 412-417.
Chan et al., "Phase behavior and miscibility in blends of poly(sebacic anhydride)/poly(ethylene glycol)", Biomaterials, (2002), vol. 23, pp. 2353-2358.
Colman, "Effects of amino acid sequence changes on antibody-antigen interactions", Research in Immunology, (1994), vol. 145, pp. 33-36.
Cone, "Barrier properties of mucus", Advanced Drug Delivery Reviews, (2009), vol. 61, pp. 75-85.
Cone, "Mucus", Mucosal Immunology, (1999), Section Edition, Chapter 4, pp. 43-64.
Cu et al., "Controlled surface modification with poly(ethylene)glycol enhances diffusion of PLGA nanoparticles in human cervical mucus", Mol Pharm., (2009), vol. 6, No. 1, 18 pages.
Dawson et al., "Enhanced Viscoelasticity of Human Cystic Fibrotic Sputum Correlates with Increasing Microheterogeneity in Particle Transport", The Journal of Biological Chemistry, (2003), vol. 278, No. 50, pp. 50393-50401.
Dawson et al., "Primary parenteral transmission of bovine spongiform encephalopathy to the pig", The Veterinary Record, (Sep. 29, 1990), 1 page.
Dawson et al., "Transport of Polymeric Nanoparticle Gene Carriers in Gastric Mucus", Biotechnol. Prog., (2004), vol. 20, No. 3, pp. 851-857.
De Campos et al., "The effect of a PEG versus a chitosan coating on the interaction of drug colloidal carriers with the ocular mucosa", European Journal of Pharmaceutical Sciences, (2003), vol. 20, pp. 73-81.
Declaration of Dr. Alexey Popov executed Feb. 21, 2013 with Curriculum vitae.
Delgado et al., "Radiolabelled biodegradable microspheres for lung imaging", European Journal of Pharmaceutics and Biopharmaceutics, (2000), vol. 50, pp. 227-236.
Denis-Mize et al., "Plasmid DNA adsorbed onto cationic microparticles mediates target gene expression and antigen presentation by dendritic cells", Gene Therapy, (2000), vol. 7, pp. 2105-2112.
Donaldson et al., "A placebo-controlled multi-centred evaluation of an anaesthetic gel (Oraqixe®) for periodontal therapy", Journal of Clinical Peridontology, (2003), vol. 30, pp. 171-175.
Dufner et al., "Harnessing phage and ribosome display for antibody optimisation", Trends in Biotechnology, (2006), vol. 24, No. 11, pp. 523-529.
Dumortier et al., "A Review of Poloxamer 407 Pharmaceutical and Pharmacological Characteristics", Pharmaceutical Research, (Dec. 2006), vol. 23, No. 12, pp. 2709-2728.

(56) References Cited

OTHER PUBLICATIONS

Ehrhardt et al., "Drug Absorption by the Respiratory Mucosa: Cell Culture Models and Particulate Drug Carriers", Journal of Aerosol Medicine, (2002), vol. 15, No. 2, pp. 131-139.

Emanuele, "FLOCOR(TM): a new anti-adhesive, rheologic agent", Expert Opinion on Investigational Drugs, (1998), vol. 7, No. 7, pp. 1193-1200.

Emanuele, "FLOCOR™: a new anti-adhesive, rheologic agent", Expert Opinion on Investigational Drugs, (1998), vol. 7, No. 7, pp. 1193-1200.

Ensign et al., "Enhanced vaginal drug delivery through the use of hypotonic formulations that induce fluid uptake", Biomaterials, (2013), vol. 34, pp. 6922-6929.

Ensign et al., "Ex Vivo Characterization of Particle Transport in Mucus Secretions Coating Freshly Excised Mucosal Tissues", Molecular Pharmaceutics, (2013), vol. 10, pp. 2176-2182.

Ensign et al., "Mucus Penetrating Nanoparticles: Biophysical Tool and Method of Drug and Gene Delivery", Advanced Materials, (2012), vol. 24, pp. 3887-3894.

Ensign et al., "Mucus-Penetrating Nanoparticles for Vaginal Drug Deliver Protect Against Herpes Simplex Virus", Science Translational Medicine, (2012), vol. 4, Issue 138, pp. 1-10.

Ensign et al., "Oral drug delivery with polymeric nanoparticles: The gastrointestinal mucus barriers", Advanced Drug Delivery Reviews, (2012), vol. 64, pp. 557-570.

Escobar-Chávez et al., "Application of Thermo-Reversible Pluronic F-127 Gels in Pharmaceutical Formulations", J. Pharm. Pharmaceut. Sci., (2006), vol. 9, No. 3, pp. 339-358.

Farokhzad et al., "Targeted nanoparticle-aptamer bioconjugates for cancer chemotherapy in vivo", PNAS, (Apr. 18, 2006), vol. 103, No. 16, pp. 6315-6320.

Fresta et al., "Ocular Tolerability and In Vivo Bioavailability of Poly(ethylene glycol) (PEG)-Coated Polyethyl-2-Cyanoacrylate Nanosphere-Encapsulated Acyclovir", Journal of Pharmaceutical Science, (Mar. 2001), vol. 90, No. 3, pp. 288-297.

Fu et al., "New polymeric carriers for controlled drug delivery following inhalation or injection", Biomaterials, (2002), vol. 23, pp. 4425-4433.

Giannavola et al., "Influence of Preparation Conditions on Acyclovir-Loaded Poly-d,I-Lactic Acid Nanospheres and Effect of PEG Coating on Ocular Drug Bioavailability", Pharmaceutical Research, (Apr. 2003), vol. 20, No. 4, pp. 584-590.

Giunchedi et al., "Emulsion Spray-Drying for the Preparation of Albumin-Loaded PLGA Microspheres", Drug Development and Industrial Pharmacy, (2001), vol. 27, No. 7, pp. 745-750.

Hancock et al., "What is the True Solubility Advantage for Amorphous Pharmaceuticals?", Pharmaceutical Research, (Nov. 4, 2000), vol. 17, No. 4, pp. 397-404.

Hida et al., "Common Gene Therapy Viral Vectors Do Not Efficiently Penetrate Sputum from Cystic Fibrosis Patients", PLoS ONE, (May 2011), vol. 6, Issue 5, pp. 1-6.

Huang et al., "Molecular aspects of muco- and bioadhesion: Tethered structures and site-specific surfaces", Journal of controlled Release, (2000), vol. 65, pp. 63-71.

International Search Report (Form PCT/ISA/210)dated Mar. 12, 2008, by the International Bureau of WIPO in corresponding International Patent Application No. PCT/US2007/019522. (5 pages).

International Search Report dated Aug. 26, 2013, in PCT/US2013/039499.

International Search Report dated Oct. 17, 2013, in PCT/US2013/039540.

Jachak et al., "Transport of metal oxide nanoparticles and single walled carbon nanotubes in human mucus", Nanotoxicology, (Sep. 2012), vol. 6, No. 6, pp. 614-622.

Jang et al., "The structural basis for DNA binding by an anti-DNA autoantibody", Molecular Immunology, (1998), vol. 35, pp. 1207-1217.

Jiang et al., "Pulsatile protein release from a laminated device comprising of polyanhydrides and pH-sensitive complexes", International Journal of Pharmaceutics, (2000), vol. 194, pp. 51-60.

Jiang et al., Preparation, characterization and degradation characteristics of polyanhydrides contained poly(ethylene glycol), Polymer International, (1999), vol. 48, pp. 47-52.

Kapin et al., "Inflammation-Mediated Retinal Edema in the Rabbit is Inhibited by Topical Nepafenac", Inflammation, (Oct. 2003), vol. 27, No. 5, pp. 281-291.

Kim et al., "Comparison of the pharmacokinetic profiles of two locally administered doxycycline gels in crevicular fluid and saliva", Journal of Clinical Periodontology, (2004), vol. 31, pp. 286-292.

Kim et al., "Use of Single-Site-Functionalized PEG Dendrons to Prepare Gene Vectors that Penetrate Human Mucus Barriers", Angewandte Chemie International Edition, (2013), vol. 52, pp. 3985-3988.

Knowles et al., "Mucus clearance as primary innate defense mechanism for mammalian airways", The Journal of Clinical Investigation, (Mar. 2002), vol. 109, No. 5, pp. 571-577.

Kobayashi et al., "Tryptophan H33 plays an important role in pyrimidine (6-4) pyrimidone photoproduct binding by a high-affinity antibody", Protein Engineering, (1999), vol. 12, No. 10, pp. 879-884.

Lai et al., "Altering Mucus Rheology to "Solidify" Human Mucus at the Nanoscale", PLoS ONE, (Jan. 2009), vol. 4, Issue 1, pp. 1-6.

Lai et al., "Drug carrier nanoparticles that penetrate human chronic rhinosinusitis mucus", Biomaterials, (2011), vol. 32, pp. 6285-6290.

Lai et al., "Micro- and macrorheology of mucus", Advanced Drug Delivery Reviews, (2009), vol. 61, pp. 86-100.

Lai et al., "Mucus-penetrating nanoparticles for drug and gene delivery to mucosal tissues", Adv. Drug Deliv. Rev., (Feb. 27, 2009), vol. 61, No. 2, 36 pages.

Lai et al., "Nanoparticles reveal that human cervicovaginal mucus is riddled with pores larger than viruses", PNAS, (Jan. 12, 2010), vol. 107, No. 2, pp. 598-603.

Lai et al., "Rapid transport of large polymeric nanoparticles in fresh undiluted human mucus", PNAS, (Jan. 30, 2007), vol. 104, No. 5, pp. 1482-1487.

Lin et al., "Carbopol.pluronic phase change solutions for ophthalmic drug delivery", Journal of Controlled Release, (2000), vol. 69, pp. 379-388.

Lipman et al., "Monoclonal Versus Polyclonal Antibodies: Distinguishing Characteristics, Applications, and Information Resources", ILAR Journal, (2005), vol. 46, No. 3, pp. 258-268.

Lo et al., "Formulation design and pharmaceutical development of a novel controlled release form of azithromycin for single-dose therapy", Drug Development and Industrial Pharmacy, (2009), vol. 35, No. 12, pp. 1522-1529.

Mert et al., "A poly(ethylene glycol)-based surfactant for formulation of drug-loaded mucus penetrating particles", Journal of Controlled Release, (2012), vol. 157, pp. 455-460.

Mu et al., "Vitamin E TPGS used as emulsifier in the solvent evaporation/extraction technique for fabrication of polymeric nanospheres for controlled release of paclitaxel (Taxol®)", Journal of Controlled Release, (2002), vol. 80, pp. 129-144.

Nance et al., "A Dense Poly(Ethylene Glycol) Coating Improves Penetration of Large Polymeric Nanoparticles Within Brain Tissue", Science Translational Medicine, (Aug. 29, 2012), vol. 4, Issue 149, pp. 1-8.

Newman et al., "Uptake of poly(D,L-lactic-co-glycolic acid) microspheres by antigen-presenting cells in vivo", Journal of Biomedical Materials Research, (Jun. 5, 2002), vol. 60, Issue 3, pp. 480-486.

Norris et al., "Effect of Size, Surface Charge, and Hydrophobicity on the Translocation of Polystyrene microspheres Through Gastrointestinal Mucin", Journal of Applied Polymer Science, (Mar. 14, 1997), vol. 63, Issue 11, pp. 1481-1492.

Norris et al., "The Uptake and Translocation of Microparticles through GI Mucin", Pharma. Res., (1995), vol. 12, pp. S233 abstract only.

Peppas et al., "Poly(ethylene glycol)-containing hydrogels in drug delivery", Journal of Controlled Release, (1999), vol. 62, pp. 81-87.

(56) References Cited

OTHER PUBLICATIONS

Peppas et al., "Ultrapure poly(vinyl alcohol) hydrogels with mucoadhesive drug delivery characteristics", European Journal of Pharmaceutics and Biopharmaceutics, (1997), vol. 43, pp. 51-58.
Peracchia et al., "PEG-coated nanospheres from amphiphilic diblock and multiblock copolymers: Investigation of their drug encapsulation and release characteristics", Journal of Controlled Release, (1997), vol. 46, pp. 223-231.
Perry, "Sorbent Materials and Sorption-Process Analysis", Perry's Chemical Engineers' Handbook, (1984), vol. 6, pp. 16-5-16-6.
Pillai et al., "Polymers in drug delivery", Current Opinion in Chemical Biology, (2001), vol. 5, pp. 447-451.
Prasad et al., "Confocal microscopy of colloids", Journal of Physics Condensed Matter, (2007), vol. 19, pp. 1-25.
Prego et al., "The potential of chitosan for the oral administration of peptides", Expert Opinion Drug Deliver, (2005), vol. 2, No. 5, pp. 843-854.
Pui, "Rasburicase: a potent uricolytic agent", Expert Opin. Pharmacother., (2002), vol. 3, No. 4, pp. 433-452.
Qiu et al., "Compatibility and degradation of new polyphosphazene/polyanhydride blend", CAPLUS, (2001), No. 5, Abstract Only.
Qiu et al., "Design of a core-shelled polymer cylinder for potential programmable drug delivery", International Journal of Pharmaceutics, (2001), vol. 219, pp. 151-160.
Rodeheaver et al., "Pluronic F-68: A Promising New Skin Wound Cleanser", Ann Emerg Med, (Nov. 1980), vol. 9, No. 11, pp. 572-576.
Rolland et al., "Direct Fabrication and Harvesting of Monodisperse, Shape-Specific Nanobiomaterials", J. Am. Chem. Soc., (2005), vol. 127, No. 28, pp. 10096-10100.
Rowbottom MV, et al. "Identification of 1-(3-(6,7-dimethoxyquinazolin-4-yloxy)phenyl)-3-(5-(1,1,1-trifluoro-2-methylpropan-2-yl)isoxazol-3-yl)urea hydrochloride (CEP-32496), a highly potent and orally efficacious inhibitor of V-RAF murine sarcoma oncogene homologue B1 (BRAF) V600E," J. Med. Chem. 55:1082-1105, 2012.
Schuster et al., "Nanoparticle diffusion in respiratory mucus from humans without lung disease", Biomaterials, (2013), vol. 34, pp. 3439-3446.
Serra et al., "Design of poly(ethylene glycol)-tethered copolymers as novel mucoadhesive drug delivery systems", European Journal of Pharmaceutics and Biopharmaceutics, (2006), vol. 63, pp. 11-18.
Serra et al., "Engineering Design and Molecular Dynamics of Mucoadhesive Drug Delivery Systems as Targeting Agents", Eur. J. Pharm. Biopharm., (Mar. 2009), vol. 71, No. 3, 24 pages.
Shakesheff et al., "The Adsorption of Poly(vinyl alcohol) to Biodegradable Microparticles Studied by X-Ray Photoelectron Spectroscopy (XPS)", Journal of Colloid and Interface Science, (1997), vol. 185, pp. 538-547.
Shuai et al., "Synthesis and characterization of several degradable aliphatic polyanhydrides", Journal of Beijing Institute of Technology (English Edition), (1996), vol. 5, No. 2, pp. 130-136 abstract only.
Singh et al., "Cationic microparticles: A potent delivery system for DNA vaccines", PNAS, (Jan. 18, 2000), vol. 97, No. 2, pp. 811-816.
Singla et al., "Paclitaxel and its formulations", International Journal of Pharmaceutics, (2002), vol. 235, pp. 179-192.
Suh et al., "PEGylation of nanoparticles improves their cytoplasmic transport", International Journal of Nanomedicine, (2007), vol. 2, No. 4, pp. 735-741.
Suh et al., "Real-time multiple-particle tracking: applications to drug and gene delivery", Advanced Drug Delivery Reviews, (2005), vol. 57, pp. 63-78.
Suk et al., "N-acetylcysteine Enhances Cystic Fibrosis Sputum Penetration and Airway Gene Transfer by Highly compacted DNA Nanoparticles", Molecular Therapy, (Nov. 2011), vol. 19, No. 11, pp. 1981-1989.
Suk et al., "Rabid transport of muco-inert nanoparticles in cystic fibrosis sputum treated with N-acetyl cysteine", Nanomedicine, (2011), vol. 6, No. 2, pp. 365-375.
Suk et al., "The penetration of fresh undiluted sputum expectorated by cystic fibrosis patients by non-adhesive polymer nanoparticles", Biomaterials, (2009), vol. 30, pp. 2591-2597.
Tang et al., "Biodegradable polymer nanoparticles that rapidly penetrate the human mucus barrier", PNAS, (Nov. 17, 2009), vol. 106, No. 46, pp. 19268-19273.

\* cited by examiner

THERAPEUTIC COMPOUNDS AND USES THEREOF

FIELD OF THE INVENTION

This invention relates to therapeutic compounds and methods of treating proliferative diseases and diseases associated with angiogenesis such as cancer and macular degeneration.

BACKGROUND OF THE INVENTION

Growth factors play an important role in angiogenesis, lymphangiogenesis, and vasculogenesis. Growth factors regulate angiogenesis in a variety of processes including embryonic development, wound healing, and several aspects of female reproductive function. Undesirable or pathological angiogenesis is associated with diseases including diabetic retinopathy, psoriasis, cancer, rheumatoid arthritis, atheroma, Kaposi's sarcoma, and hemangioma (Fan et al., 1995, *Trends Pharmacol. Sci.* 16: 57 66; Folkman, 1995, *Nature Medicine* 1: 27 31). Angiogenic ocular conditions represent the leading cause of irreversible vision loss in developed countries. In the United States, for example, retinopathy of prematurity, diabetic retinopathy, and age-related macular degeneration are the principal causes of blindness in infants, working age adults, and the elderly, respectively. Efforts have been developed to promote angiogenesis in treatment of these conditions (Roskoski, *Critical Reviews in Oncology/Hematology*, 62 (2007), 179-213).

Therefore, there is a need for new therapeutic compounds for the treatment of diseases associated with aberrant signaling of growth factors, such as cancer, macular degeneration, and diabetic retinopathy.

SUMMARY OF THE INVENTION

The present invention provides compounds of Formulae (I)-(III), pharmaceutical compositions thereof, and kits to treat proliferative diseases, ocular diseases, dermatological diseases, inflammatory diseases, autoimmune diseases, autoinflammatory diseases, and metabolic diseases. The present invention also provides methods of using the inventive compounds, and pharmaceutically acceptable salts, solvates, hydrates, polymorphs, co-crystals, tautomers, stereoisomers, isotopically labeled derivatives, or prodrugs thereof, and compositions thereof, to study the inhibition of growth factor signaling and/or to treat and/or prevent proliferative diseases, ocular diseases, dermatological diseases, inflammatory diseases, autoimmune diseases, autoinflammatory diseases, and metabolic diseases. The inventive compounds are particularly useful in treating diseases associated with angiogenesis.

In one aspect, the present invention provides compounds of Formula (I):

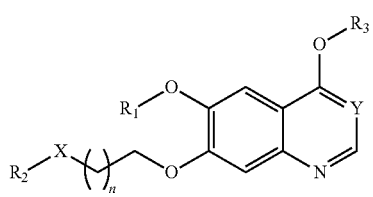

or a pharmaceutically acceptable salt, solvate, hydrate, polymorph, co-crystal, tautomer, stereoisomer, isotopically labeled derivative, or prodrug thereof, wherein $R_1$, $R_2$, $R_3$, X, Y, and n are as defined herein.

In one aspect, the present invention provides compounds of Formula (II):

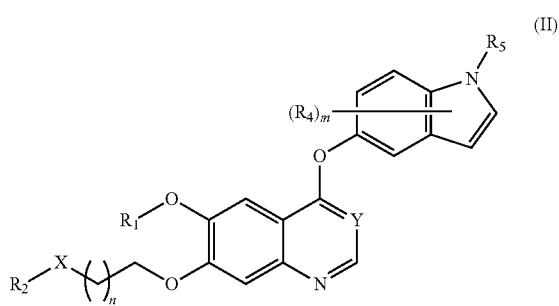

or a pharmaceutically acceptable salt, solvate, hydrate, polymorph, co-crystal, tautomer, stereoisomer, isotopically labeled derivative, or prodrug thereof, wherein $R_1$, $R_2$, $R_4$, $R_5$, X, Y, m, and n are as defined herein.

In one aspect, the present invention provides compounds of Formula (III):

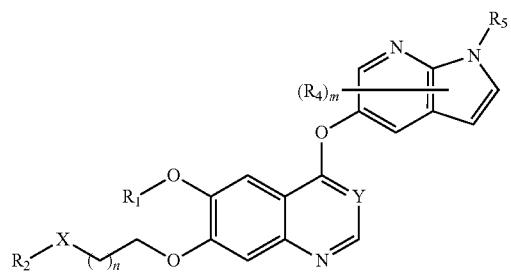

or a pharmaceutically acceptable salt, solvate, hydrate, polymorph, co-crystal, tautomer, stereoisomer, isotopically labeled derivative, or prodrug thereof, wherein $R_1$, $R_2$, $R_4$, $R_5$, X, Y, m, and n are as defined herein.

Exemplary compounds of Formulae (I)-(III) include, but are not limited to:

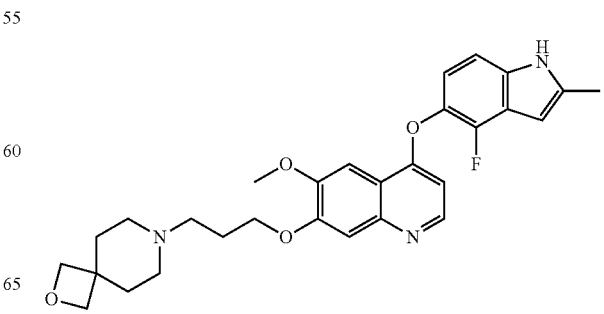

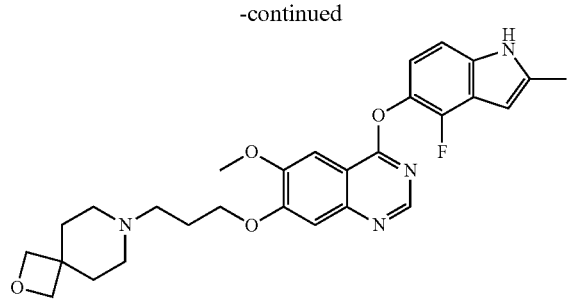
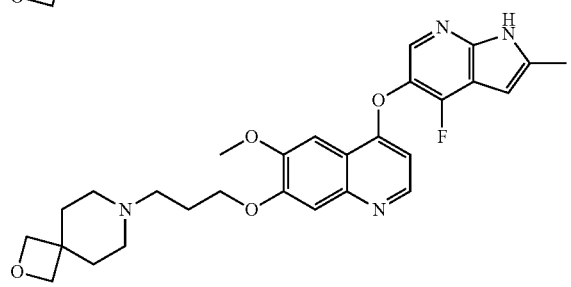
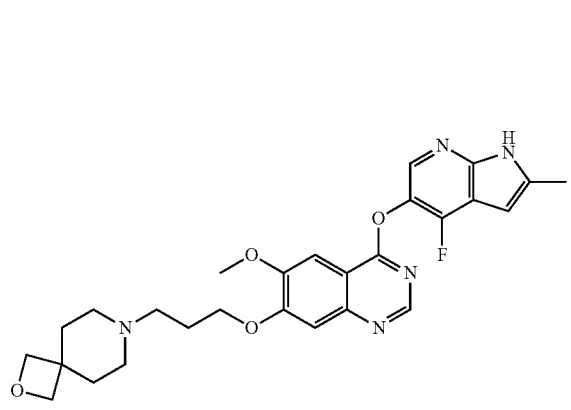
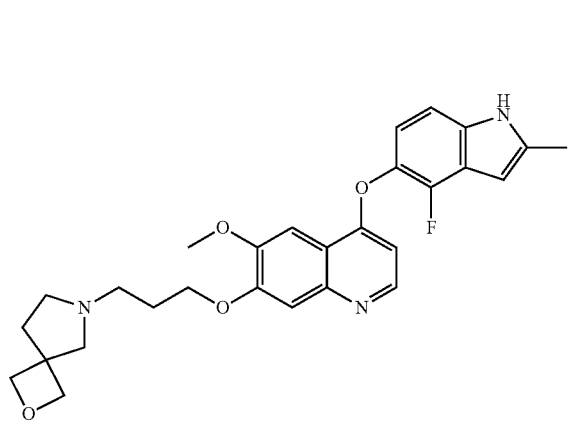
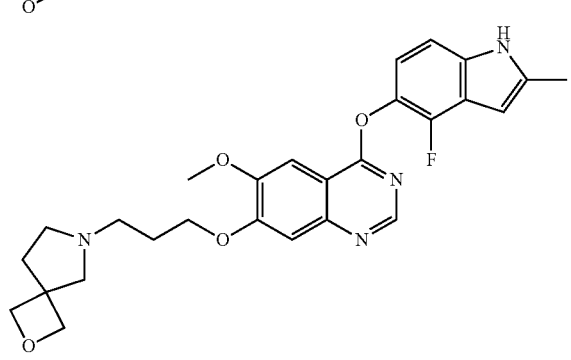
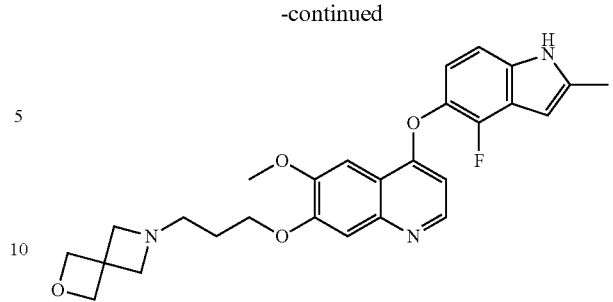
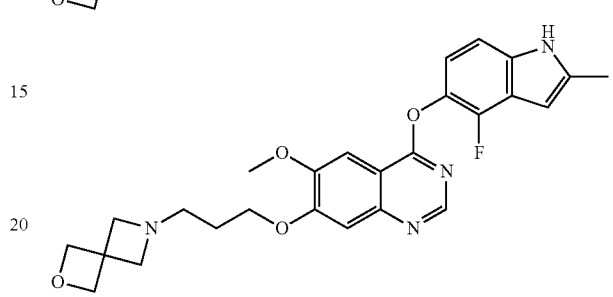
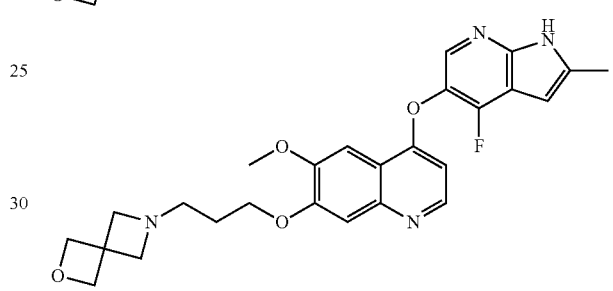
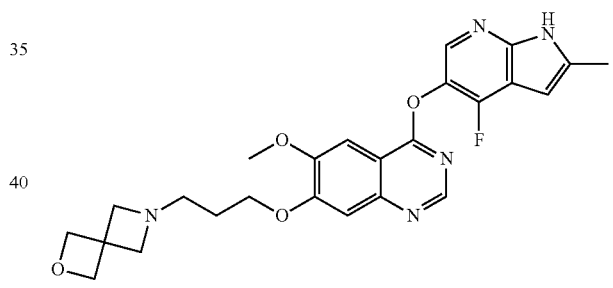
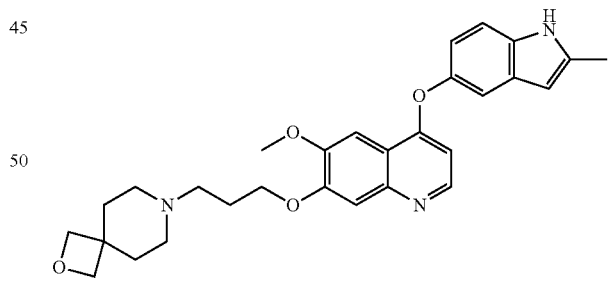
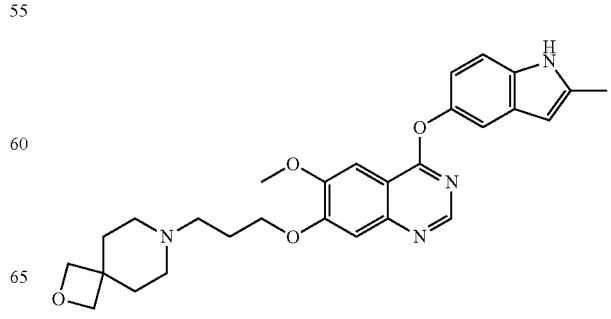

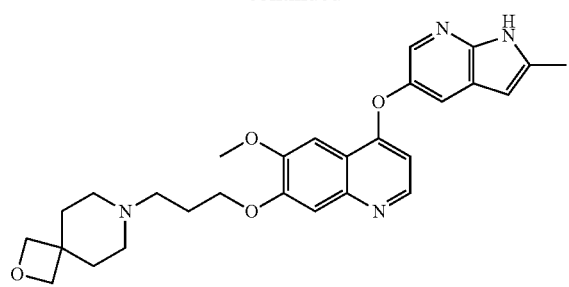
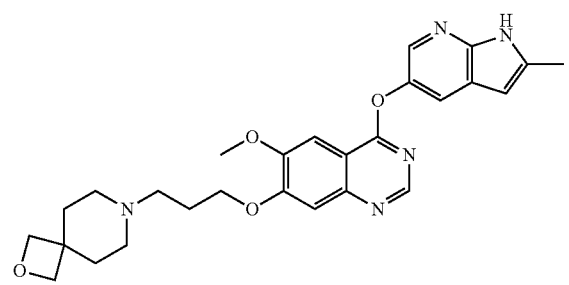
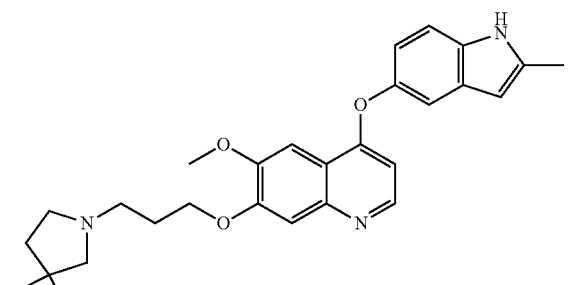
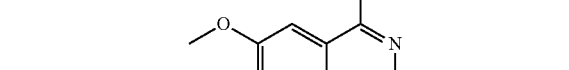
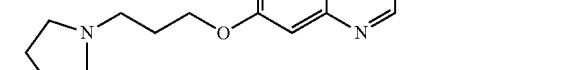
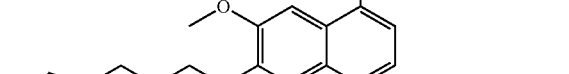
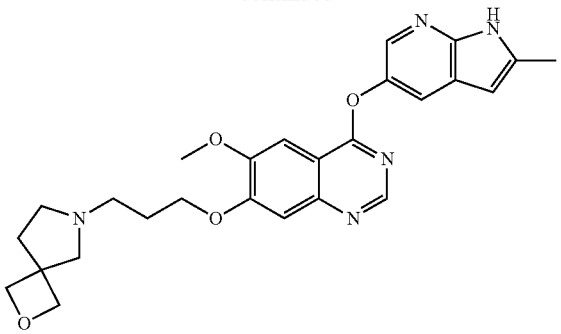
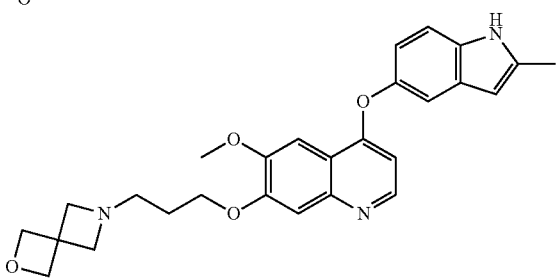
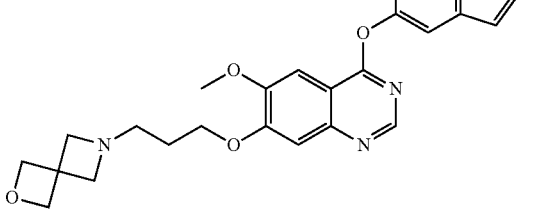
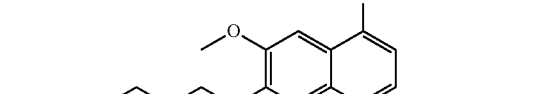
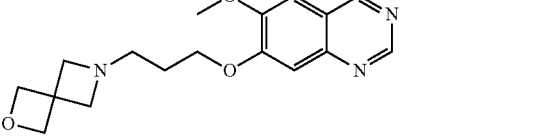
Other exemplary compounds of Formulae (I)-(III) include, but are not limited to:

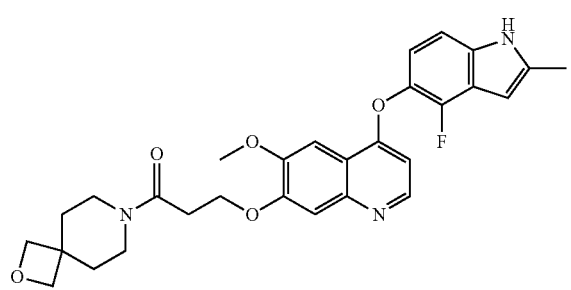
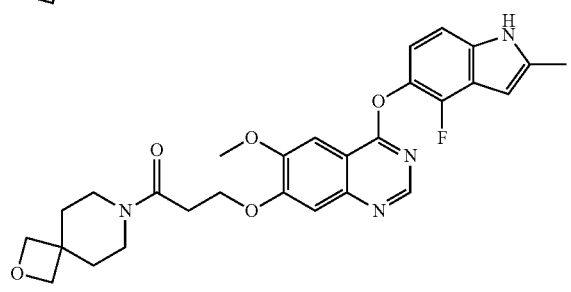
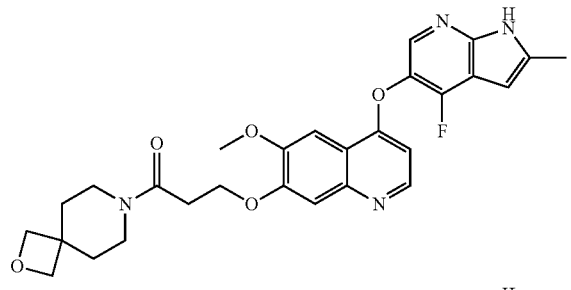
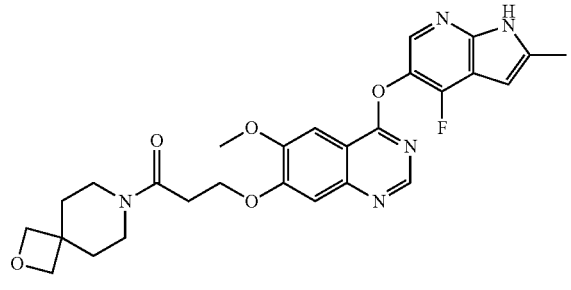
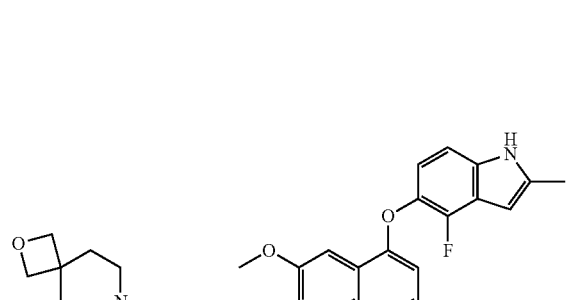
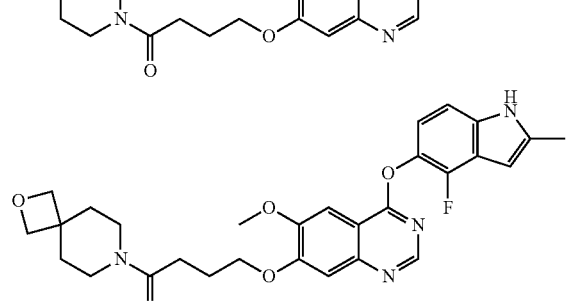
-continued
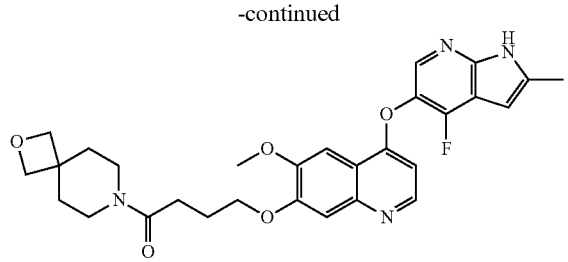
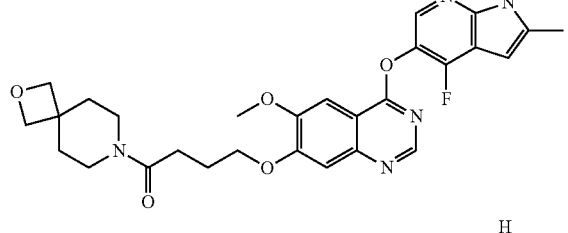
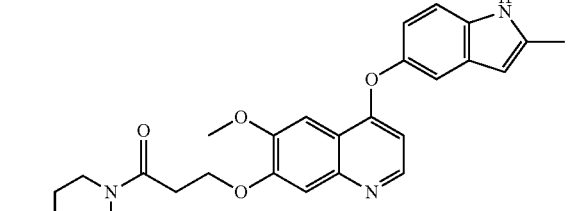
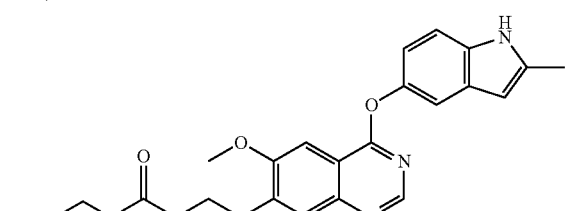
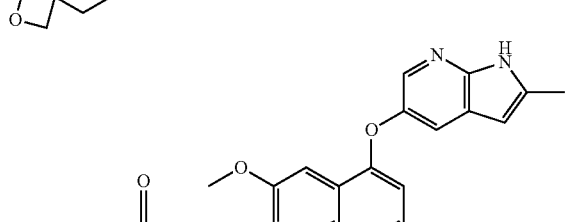
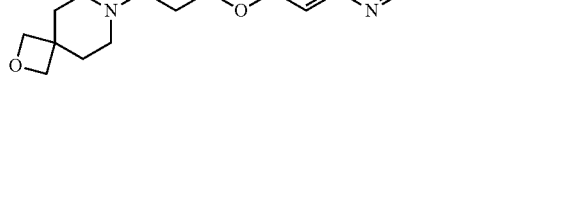
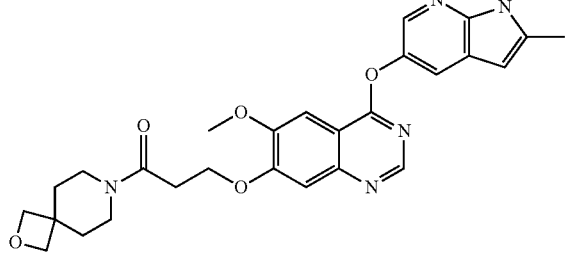

-continued
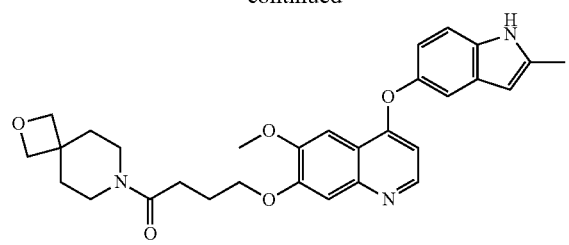
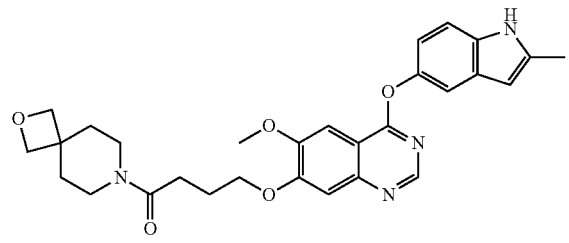
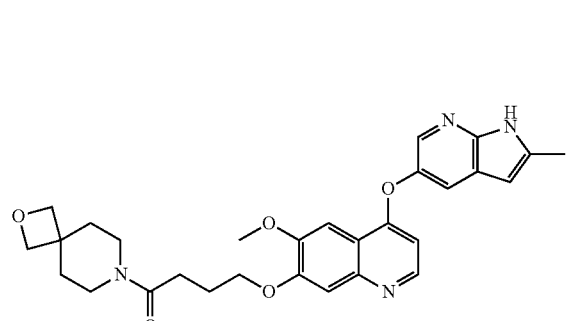
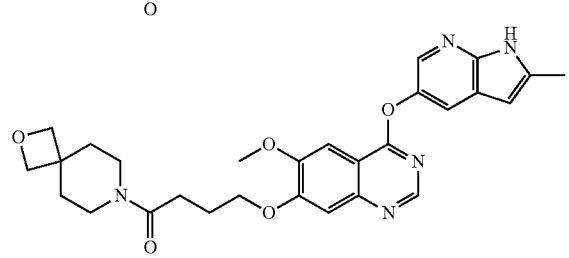
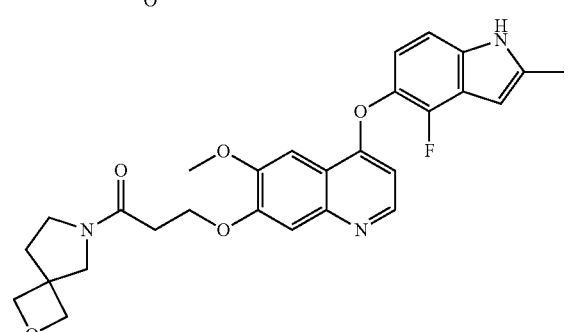
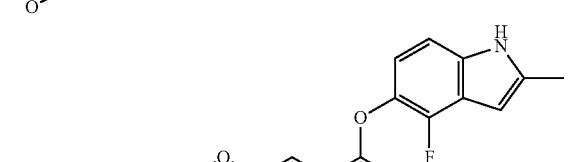
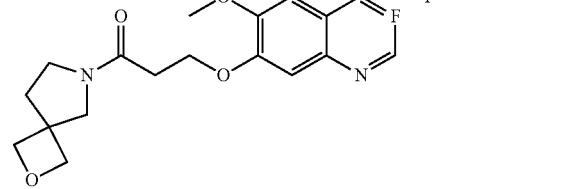
-continued
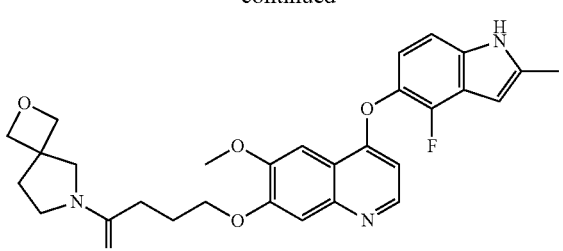
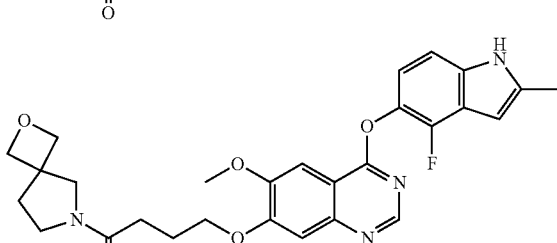
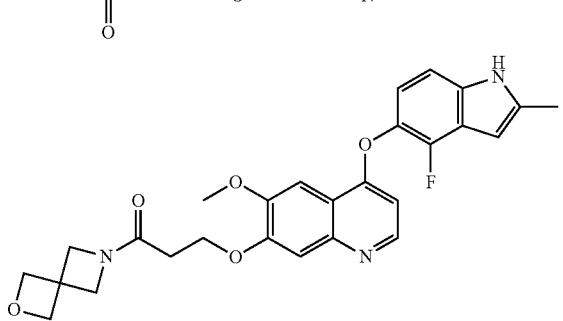
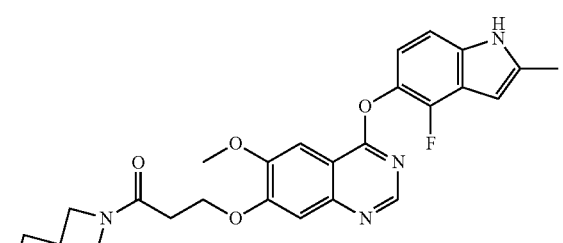
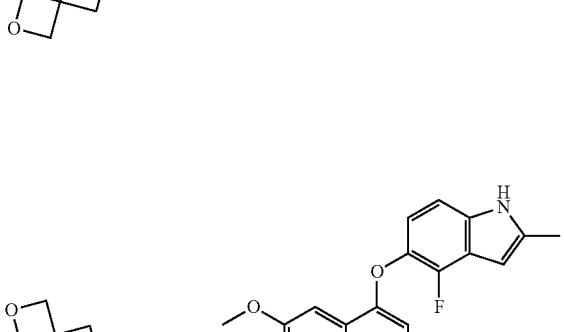
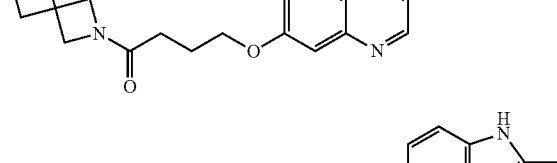
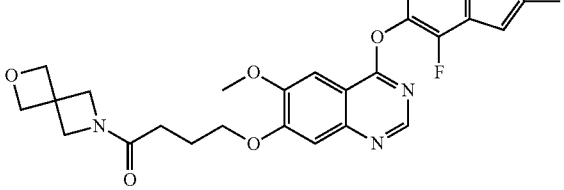

-continued
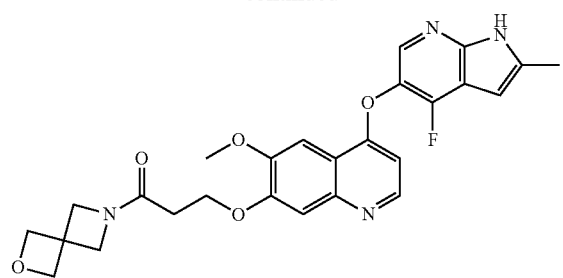
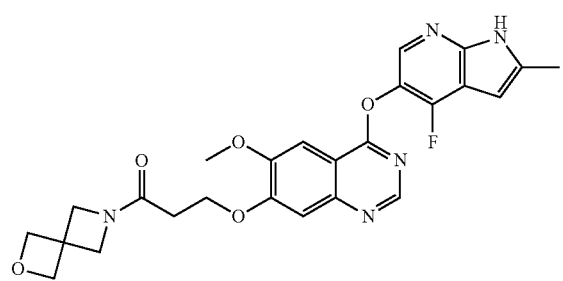
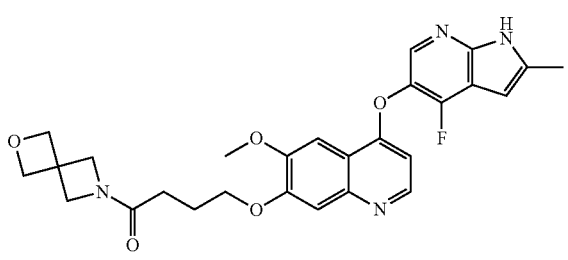
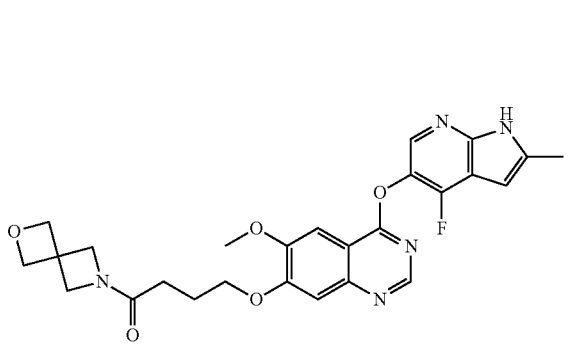
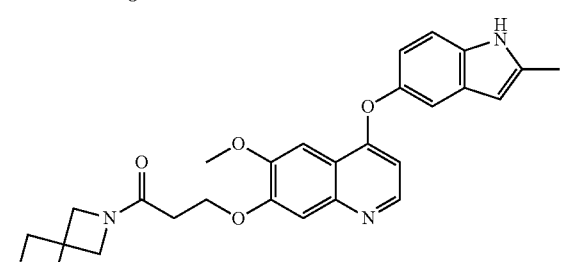
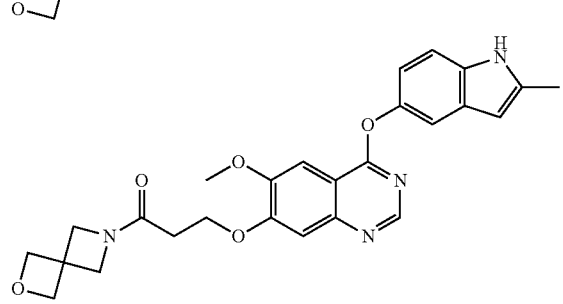
-continued
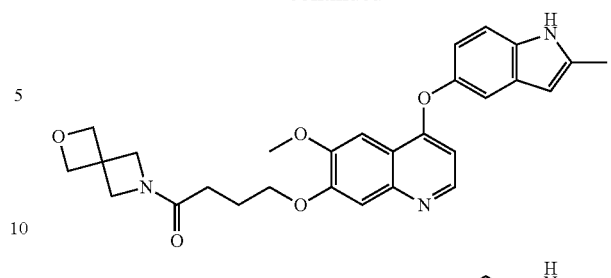
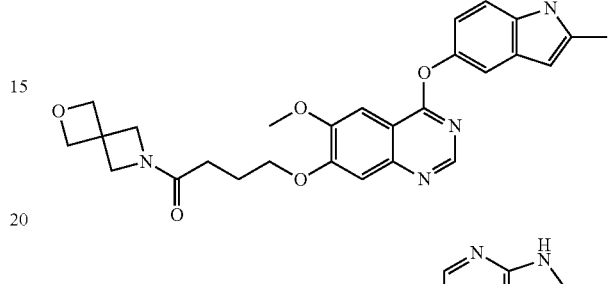
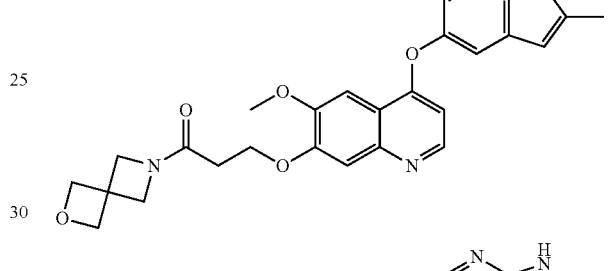
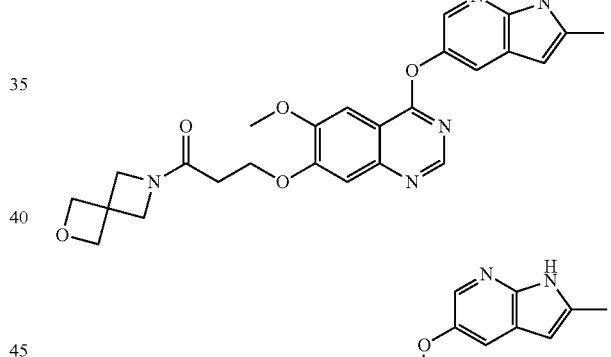
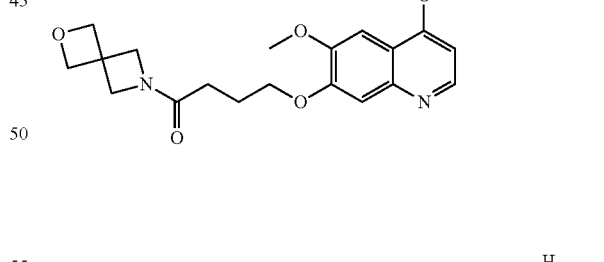
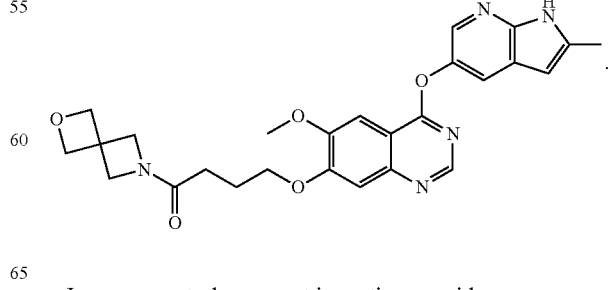
In one aspect, the present invention provides a compound of Formula (I):

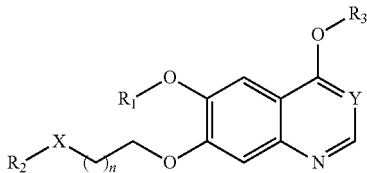

I or a pharmaceutically acceptable salt, solvate, hydrate, polymorph, co-crystal, tautomer, stereoisomer, isotopically labeled derivative, or prodrug thereof, wherein $R_2$, is hydrogen, X is a bond, n is 0, and $R_1$, $R_3$, and Y are as defined herein.

In certain embodiments, the compound of the invention is

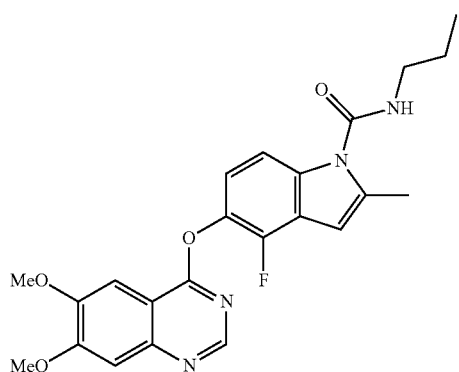 [SMILES: CCCNC(=O)n1c(C)cc2c(F)c(Oc3ncnc4cc(OC)c(OC)cc34)ccc21]

or a pharmaceutically acceptable salt, solvate, hydrate, polymorph, co-crystal, tautomer, stereoisomer, isotopically labeled derivative, or prodrug thereof.

In another aspect, the present invention provides pharmaceutical compositions comprising a compound of Formula (I), (II), or (III), or a pharmaceutically acceptable salt, solvate, hydrate, polymorph, co-crystal, tautomer, stereoisomer, isotopically labeled derivative, or prodrug thereof, and optionally a pharmaceutically acceptable carrier. In certain embodiments, the pharmaceutical compositions described herein include a therapeutically effective amount of a compound of Formula (I), (II), or (III), or a pharmaceutically acceptable salt, solvate, hydrate, polymorph, co-crystal, tautomer, stereoisomer, isotopically labeled derivative, or prodrug thereof. The pharmaceutical composition may be useful for treating proliferative diseases, ocular diseases, dermatological diseases, inflammatory diseases, autoimmune diseases, autoinflammatory diseases, and metabolic diseases. In certain embodiments, the ocular disease being treated is macular degeneration.

In some embodiments, the compounds described herein may be intended for delivery in a subject's tissues having mucus (e.g., eye, respiratory tract, gastrointestinal tract, genito-urinary tract), which is a viscoelastic and adhesive substance that traps most foreign objects (e.g., microorganisms, particles, dust). For effective drug delivery, compound or particles that are immobilized in the mucus are quickly eliminated by mucus clearance mechanisms; therefore, they are not able to effectively deliver the intended therapeutic effect. In these tissues, for the compound to be effective, it must quickly penetrate the mucus and/or avoid mucus clearance mechanisms. Accordingly, modifying mucoadhesive compounds or particles containing compounds with a coating to reduce the mucoadhesiveness, and decreasing the size of the particles of compound may allow for efficient delivery and therapeutic effect.

In one aspect of the invention, the compounds described herein are formulated into mucus penetrating particles or mucus penetrating crystals (collectively, MPPs) suitable for administration (e.g., topical or inhalation) to tissues of the subject having mucus (e.g., eye, respiratory tract, gastrointestinal tract, genito-urinary tract). In certain embodiments, the inventive compounds are crystalline.

In another aspect, the present invention provides particles containing a compound described herein or particles comprising a compound described herein. In certain embodiments, the particles are mucus penetrating. The particles of the invention may include a coating surrounding a core. The core may contain primarily a compound of the invention, or the core may be a polymeric core with the compound encapsulated in the polymer. In certain embodiments, the inventive particles are nanoparticles (e.g., particles having an average diameter of at least about 10 nm and less than about 1 μm). The inventive particles may be useful in delivering the pharmaceutical agent to a subject. In certain embodiments, the particles of the invention are capable of delivering the pharmaceutical agent in or through mucus of a subject.

Another aspect of the invention relates to pharmaceutical compositions comprising an inventive compound and/or a plurality of inventive particles. In certain embodiments, the pharmaceutical compositions are useful in delivering a pharmaceutical agent (e.g., the compound of the invention) to a subject.

In another aspect of the invention, the present invention provides pharmaceutical composition comprising a plurality of particles comprising (i) a core comprising a compound of the invention described herein, or a pharmaceutically acceptable salt thereof, and (ii) a coating of a surface altering agent surrounding the core, wherein the surface altering agent is present on the outer surface of the core at a density of at least 0.01 surface altering agent per $nm^2$, and optionally, at least one pharmaceutically acceptable excipient. In some embodiments, the surface altering agent is a triblock copolymer of the structure (hydrophilic block)-(hydrophobic block)-(hydrophilic block). In some aspects, the triblock copolymer is a PLURONIC or poloxamer.

In certain embodiments, the compound, particle, or pharmaceutical composition is formulated to be mucus penetrating.

In another aspect, the present invention provides methods of treating or preventing a disease by administering to a subject in need thereof a therapeutically effective amount of a compound of Formula (I), (II), or (III). The diseases include proliferative diseases, ocular diseases, dermatological diseases, inflammatory diseases, autoimmune diseases, autoinflammatory diseases, and metabolic diseases.

In another aspect, the present invention provides kits comprising a compound of Formula (I), (II), or (III), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (I), (II), or (III), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment of proliferative diseases, ocular diseases, dermatological diseases, inflammatory diseases, autoimmune diseases, autoinflammatory diseases, and metabolic diseases. In certain embodiments, the kits described herein further include instructions for administering the compound of Formula (I), (II), or (III), or the pharmaceutically acceptable salt, solvate, hydrate, polymorph, co-crystal, tautomer, stereoisomer, isotopically labeled derivative, or prodrug thereof, or the pharmaceutical composition thereof. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a dropper for ocular administration or a syringe for parenteral administration.

The details of certain embodiments of the invention are set forth herein. Other features, objects, and advantages of the invention will be apparent from the Detailed Description, Figures, Examples, and Claims.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, a "hydrocarbon chain" refers to a substituted or unsubstituted divalent alkyl, alkenyl, or alkynyl group. A hydrocarbon chain includes at least one chain, each node ("carbon unit") of which including at least one carbon atom between the two radicals of the hydrocarbon chain. For example, hydrocarbon chain —$C^A$H($C^B$H$_2$$C^C$H$_3$)— includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —CH($C_2H_5$)— is a $C_1$ hydrocarbon chain, and

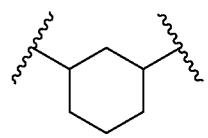 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —(CH$_2$)$_4$—). In certain embodiments, the hydrocarbon chain is substituted (e.g., —CH($C_2H_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

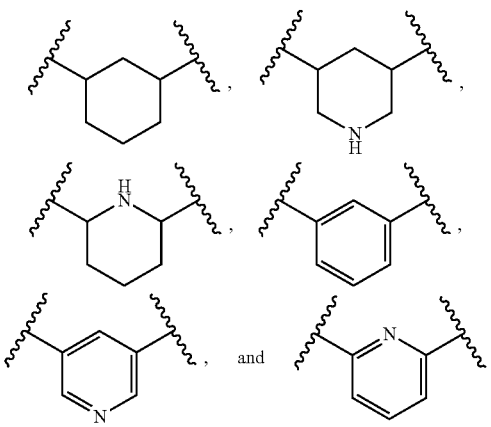

are all examples of a hydrocarbon chain. In contrast, in certain embodiments

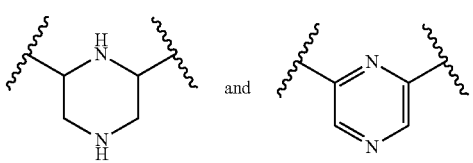 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —CH$_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused to one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl, and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Arylalkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen, and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix-ene, e.g., alkylene, alkenylene, alkynylene, carbocyclylene, heterocyclylene, arylene, and heteroarylene.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —ON, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —ON, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electrostaticneutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)$R^{aa}$, —CHO, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2$$R^{aa}$, —C(=S)N($R^{bb}$)$_2$, —C(=O)S$R^{aa}$, and —C(=S)S$R^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachloro-benzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxy-piperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl 5,5-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate(levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate(mesitoate), alkyl methyl carbonate, 9-fluorenylmethyl carbonate (Fmoc), alkyl ethyl carbonate, t-butyl carbonate (BOC), alkyl 2,2,2-trichloroethylcarbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$ $R^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formulae (I)-(III) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound, and x is a number greater than 0. A given compound may form more than one type of hydrates, including, e.g., monohydrates (x is 1), lower hydrates (x is a number greater than 0 and smaller than 1, e.g., hemihydrates (R.0.5 H$_2$O)), and polyhydrates (x is a number greater than 1, e.g., dihydrates (R.2 H$_2$O) and hexahydrates (R.6 H$_2$O)).

As used herein, the term "tautomer" includes two or more interconvertable forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I), which have cleavable groups and become by solvolysis or under physiological conditions the compounds of Formula (I)-(III) which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy) alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formulae (I)-(III) may be preferred in certain instances.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formulae (I)-(III) refers to an amount sufficient to elicit a desired biological response, i.e., treating the condition. As will be appreciated by those of ordinary skill in this art, the effective amount of a compound of Formulae (I)-(III) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor. In treating macular degeneration, an effective amount of an inventive compound may improve sight, reduce the risk of vision loss, or prevent central vision loss from worsening.

A "therapeutically effective amount" of a compound of Formulae (I)-(III) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formulae (I)-(III) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and growth of new blood vessels. Normal angiogenesis occurs in the body of a healthy subject during wound healing and for restoring blood flow to tissues after injury. The body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can result in new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyosifis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fascilitis, and necrotizing enterocolitis.

As used herein, an "autoimmune disease" refers to a disease arising from an inappropriate immune response in the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppressants, e.g., medications which decrease the immune response. Exemplary autoimmune diseases include, but are not limited to, glomerulonephritis, Goodspature's syndrome, necrotizing vasculitis, lymphadenitis, peri-arteritis nodosa, systemic lupus erythematosus, rheumatoid, arthritis, psoriatic arthritis, systemic lupus erythematosus, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjogren's syndrome, Crohn's disease, Reiter's syndrome, ankylosing spondylitis, Lyme arthritis, Guillain-Barre syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behcet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

A "protein" or "peptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

The term "kinase" refers to any enzyme that catalyzes the addition of a phosphate group to a residue of a protein. For example, a serine kinase catalyzes the addition of a phosphate group to a serine residue of a protein.

The term "ocular disease" or "ocular disorder" refers to any eye disease and/or disorder. For example, ocular diseases can be disorders of the eyelid, lacrimal system and orbit, disorders of conjunctiva, disorders of sclera, cornea, iris and ciliary body, disorders of choroid and retina, glaucoma, disorders of optic nerve and visual pathways, or disorders of ocular muscles. Additionally, orcular disease can also refer to discomfort following injury, surgery, or laser treatment. Diseases and disorders of the eye include, but are not limited to, macular degeneration, dry eye syndrome, uveitis, allergic conjunctivitis, glaucoma, and rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals. Uveitis or iridocyclitis refers to inflammation of the middle layer of the eye (the "uvea") and in common usage may refer to any inflammatory process involving the interior of the eye. Allergic conjunctivitis is inflammation of the conjunctiva (the membrane covering the white part of the eye) due to allergy. Glaucoma refers to a group of diseases that affect the optic nerve and involves a loss of retinal ganglion cells in a characteristic pattern, i.e., a type of optic neuropathy. Raised intraocular pressure is a significant risk factor for developing glaucoma (above 22 mmHg or 2.9 kPa), and inflammatory processes, e.g., uveitis, can cause this rise in intraocular pressure. Rosacea is a chronic inflammatory condition characterized by facial erythema but it can affect the eyes.

The terms "macular degeneration," "age-related macular degeneration," "dry AMD," and "central geographic atrophy" are used interchangeably herein. These terms refer to diseases that result from atrophy of the retinal pigment epithelial layer below the neurosensory retina, which causes vision loss through loss of photoreceptors (rods and cones) in the central part of the retinal.

The term "VEGF" is used interchangeably with vascular endothelial growth factor herein. VEGF includes, but is not limited to, VEGF-related proteins such as placenta growth factor (PlGF), VEGF-A, VEGF-B, VEGF-C, VEGF-D, VEGF-E, and VEGF-F. The term VEGF also covers a number of proteins from two families that result from alternate splicing of mRNA from a single, 8-exon, VEGF gene. The two different families are referred to according to their terminal exon (exon 8) splice site—the proximal splice site (denoted $VEGF_{xxx}$) or distal splice site ($VEGF_{xxxb}$). In addition, alternate splicing of exon 6 and 7 alters their heparin-binding affinity, and amino acid number (in humans: $VEGF_{121}$, $VEGF_{121b}$, $VEGF_{145}$, $VEGF_{165}$, $VEGF_{165b}$, $VEGF_{189}$, $VEGF_{206}$; the rodent orthologs of these proteins contain one fewer amino acid). These domains have important functional consequences for the VEGF splice variants, as the terminal (exon 8) splice site determines whether the proteins are pro-angiogenic (proximal splice site, expressed during angiogenesis) or anti-angiogenic (distal splice site, expressed in normal tissues). In addition, inclusion or exclusion of exons 6 and 7 mediate interactions with heparan sulfate proteoglycans (HSPGs) and neuropilin co-receptors on the cell surface, enhancing their ability to bind and activate the VEGF receptors (VEGFRs). The term "VEGF" also encompasses VEGF receptors. There are three main subtypes of VEGFR, numbered 1, 2 and 3. Also, they may be membrane-bound (mbVEGFR) or soluble (sVEGFR), depending on alternative splicing.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals (e.g., crystalline forms of compounds or active pharmaceutical agent), aggregates, composites, pulverized, milled, or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having a characteristic dimension of less than about 1 micrometer and at least about 1 nanometer, where the characteristic dimension of the particle is the smallest cross-sectional dimension of the particle. A crystalline nanoparticle is referred to as a "nanocrystal."

The term "microparticle" refers to a particle having a characteristic dimension of less than about 1 millimeter and at least about 1 micrometer, where the characteristic dimension of the particle is the smallest cross-sectional dimension of the particle.

The term "nanostructure" refers to a structure having at least one region or characteristic dimension with a dimension of less than about 1000 nm, e.g., less than about 300 nm, less than about 200 nm, less than about 100 nm, or less than about 50 nm. Typically, the region or characteristic dimension will be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), and the like. Nanostructures can be substantially homogeneous in material properties, or in certain embodiments can be heterogeneous (e.g. heterostructures). Nanostructures can be, e.g., substantially crystalline, substantially monocrystalline, polycrystalline, amorphous, or a combination thereof. In one aspect, each of the three dimensions of the nanostructure has a dimension of less than about 1000 nm, e.g., or even less than about 300 nm, less than about 200 nm, less than about 100 nm, or less than about 50 nm. Nanostructures can comprise one or more surface ligands (e.g., surfactants).

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein. The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal. When not used with respect to a nanostructure, the term "monocrystalline" to materials that are composed of substantially a single crystallite of substantially the same size and orientation.

"Nanocrystal" is a nanostructure that is substantially monocrystalline. A nanocrystal thus has at least one region or characteristic dimension with a dimension of less than about 1000 nm, e.g., less than about 300 nm less than about 200 nm, less than about 100 nm, or less than about 50 nm. Typically, the region or characteristic dimension will be along the smallest axis of the structure. Examples of such structures include nanowires, nanorods, nanotubes, branched nanowires, nanotetrapods, nanotripods, nanobipods, nanocrystals, nanodots, quantum dots, nanoparticles, nanoribbons, and the like. Nanostructures can be substantially homogeneous in material properties, or in certain embodiments can be heterogeneous (e.g. heterostructures). Optionally, a nanocrystal can comprise one or more surface ligands (e.g., surfactants). The nanocrystal is optionally substantially single crystal in structure (a "single crystal nanostructure" or a "monocrystalline nanostructure"). While nanostructures for use in the present invention can be fabricated from essentially any convenient material or material, preferably the nanostructure is prepared from an inorganic material, e.g., an inorganic conductive or semiconductive material. A conductive or semi-conductive nanostructure often displays 1-dimensional quantum confinement, e.g., an electron can often travel along only one dimension of the structure. Nanocrystals can be substantially homogeneous in material properties, or in certain embodiments can be heterogeneous (e.g. heterostructures). The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. The nanocrystals can be fabricated from essentially any convenient material or materials.

The term "polycrystalline" refers to materials that are composed of many crystallites of varying size and orientation. When used with respect to nanostructures, the term "polycrystalline" refers to a crystalline nanostructure that is not monocrystalline.

A "biocompatible" material refers to a material that does not typically induce an adverse response when inserted or injected into a subject. The adverse response includes significant inflammation and/or acute rejection of the material by the immune system of the subject, for instance, via a T-cell-mediated response. It is recognized that "biocompatibility" is a relative term and that some degree of immune response is to be expected even for materials that are highly compatible with living tissues of the subject. However, as used herein, "biocompatibility" refers to the acute rejection of a material by at least a portion of the immune system, i.e., a material that lacks biocompatibility (i.e. being non-biocompatible) in a subject provokes an immune response in the subject that is severe enough such that the rejection of the material by the immune system cannot be adequately controlled and often is of a degree such that the material must be removed from the subject in order for the subject to be as well as it was before the non-biocompatible material was introduced into the subject. One test to determine biocompatibility of a material is to expose the material to cells (e.g., fibroblasts or epithelial cells) in vitro; the material is considered biocompatible if it does not result in significant cell death at moderate concentrations, e.g., at concentrations of about 50 micrograms/$10^6$ cells. In certain embodiments, there is no significant cell death if less than about 20% of the cells are dead, even if phagocytosed or otherwise uptaken by the cells. In some embodiments, a material is biocompatible if contacting it with cells in vitro results in less than 20% cell death and if the administration of the material in vivo does not induce unwanted inflammation or other adverse responses. In certain embodiments, a biocompatible material is biodegradable. A non-limiting example of biocompatible materials is biocompatible polymers (including biocompatible copolymers).

A "biodegradable" material refers to a material that is able to degrade chemically and/or biologically (e.g., by hydrolysis or enzymatic activity), within a physiological environment, such as within the body or when introduced to cells. For instance, the material may be one that hydrolyzes spontaneously upon exposure to water (e.g., within a subject) and/or may degrade upon exposure to heat (e.g., at temperatures of about 37° C.). Degradation of a material may occur at varying rates, depending on the material used. For example, the half-life of the material (the time at which 50% of the material is degraded into smaller components) may be on the order of days, weeks, months, or years. The material may be biologically degraded, e.g., by enzymatic activity or cellular machinery, for example, through exposure to a lysozyme. In some embodiments, the material may be broken down into smaller components that cells can either reuse or dispose of without significant toxic effect on the cells (e.g., fewer than about 20% of the cells are killed when the components are added to cells in vitro). Non-limiting examples of biodegradable materials are biodegradable polymers (including biodegradable copolymers). Examples of biodegradable polymers include, but are not limited to, poly(ethylene glycol)-poly(propylene oxide)-poly(ethylene glycol) triblock copolymers, poly(vinyl alcohol) (PVA), poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters), and copolymers thereof (e.g., poly(lactide-co-glycolide) (PLGA)).

As used herein, the terms "pharmaceutical composition" and "formulation" are used interchangeably.

As used herein, the terms "pharmaceutical agent" and "drug" are used interchangeably.

DETAILED DESCRIPTION OF CERTAIN EMBODIMENTS OF THE INVENTION

The present invention provides compounds of Formulae (I)-(III). Also provided are methods of using compounds of Formulae (I)-(III), to treat proliferative diseases, ocular diseases, dermatological diseases, inflammatory diseases, autoimmune diseases, autoinflammatory diseases, and metabolic diseases. The present invention further provides methods of using the compounds of Formulae (I)-(III) as therapeutics, e.g., in the treatment and/or prevention of diseases associated with growth factor activity or angiogenesis. In certain embodiments, the disease being treated is a proliferative disease. Exemplary proliferative diseases include, but are not limited to, cancers, benign neoplasms, diseases associated with angiogenesis, inflammatory diseases, autoinflammatory diseases, and autoimmune diseases. In certain embodiments, the disease is an ocular disease. Exemplary ocular diseases include, but are not limited to, macular degeneration, dry eye syndrome, uveitis, allergic conjunctivitis, glaucoma, and rosacea.

Compounds

As generally described above, provided herein are compounds of Formulae (I)-(III). In certain embodiments, the present disclosure provides compounds of Formula (I):

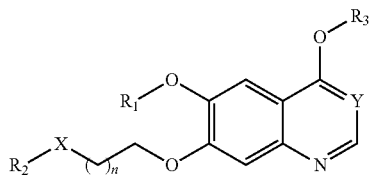

and pharmaceutically acceptable salts, solvates, hydrates, polymorphs, co-crystals, tautomers, stereoisomers, isotopically labeled derivatives, and prodrugs thereof, wherein:

$R_1$ is independently hydrogen or optionally substituted $C_{1-6}$ alkyl;

$R_2$ is optionally substituted carbocyclyl, optionally substituted heterocyclyl, optionally substituted aryl, or optionally substituted heteroaryl;

$R_3$ is optionally substituted alkyl, optionally substituted aryl, optionally substituted heteroaryl, optionally substituted heterocyclyl, optionally substituted heterocyclylalkyl, optionally substituted heteroaralkyl;

X is a bond, —O—, —S—, —$NR^{41}$—, —C(=O)—, or branched or unbranched optionally substituted $C_{1-6}$ alkylene, wherein $R^{41}$ is independently hydrogen, optionally substituted acyl, optionally substituted alkyl, or a nitrogen protecting group;

Y is N or CH; and n is 0, 1, 2, 3, 4, 5, 6, 7, 8, 9, or 10.

In certain embodiments, the present disclosure provides compounds of Formula (I):

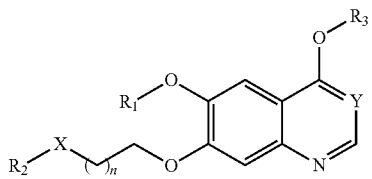

and pharmaceutically acceptable salts, solvates, hydrates, polymorphs, co-crystals, tautomers, stereoisomers, isotopically labeled derivatives, and prodrugs thereof, wherein $R_2$ is hydrogen, X is a bond, n is 0, and $R_1$ is independently hydrogen or optionally substituted $C_{1-6}$ alkyl;

$R_2$ is hydrogen;

$R_3$ is optionally substituted alkyl, optionally substituted aryl, optionally substituted heteroaryl, optionally substituted heterocyclyl, optionally substituted heterocyclylalkyl, optionally substituted heteroaralkyl;

X is a bond;

Y is N or CH; and

N is 0.

As generally described above, $R_3$ is optionally substituted alkyl, optionally substituted aryl, optionally substituted heteroaryl, optionally substituted heterocyclyl, optionally substituted heterocyclylalkyl, optionally substituted heteroaralkyl. In certain embodiments, $R_3$ is unsubstituted methyl. In certain embodiments, $R_3$ is substituted methyl. In certain embodiments, $R_3$ is unsubstituted ethyl. In certain embodiments, $R_3$ is substituted ethyl. In certain embodiments, $R_3$ is optionally substituted propyl. In certain embodiments, $R_3$ is substituted n-propyl. In certain embodiments, $R_3$ is unsubstituted n-propyl. In certain embodiments, $R_3$ is substituted iso-propyl. In certain embodiments, $R_3$ is unsubstituted iso-propyl.

In certain embodiments, $R_3$ is optionally substituted heteroaryl having 1-4 heteroatoms independently selected from nitrogen, oxygen, and sulfur. In certain embodiments, $R_3$ is optionally substituted monocyclic heteroaryl. In certain embodiments, $R_3$ is optionally substituted bicyclic heteroaryl.

In certain embodiments, $R_3$ is a heteroaryl ring fused with one or more carbocyclic, heterocyclic, aryl, or heteroaryl groups. In certain embodiments, $R_3$ is a bicyclic heteroaryl ring. In certain embodiments, $R_3$ is a monocyclic heteroaryl ring fused with an aryl ring. In certain embodiments, $R_3$ is of the formula:

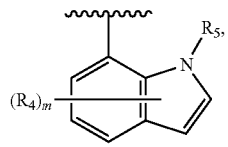

wherein each instance of $R^4$ is independently hydrogen, halogen, optionally substituted alkyl, optionally substituted carbocyclyl, optionally substituted heterocyclyl, optionally substituted aryl, optionally substituted heteroaryl, —$OR^{4A}$, —$N(R^{4A})_2$, —$SR^{4A}$, —CN, —C(=O)$R^{4A}$, —C(=O)$OR^{4A}$, —C(=O)N($R^{4A})_2$, —$NO_2$, —$N_3$, —N($R^{4A})_3^+X^-$, wherein $X^-$ is a counterion, —OC(=O)$R^{4A}$, or —OC(=O)$OR^{4A}$, or two $R^4$ groups are joined to form an optionally substituted carbocyclic, optionally substituted heterocyclic, optionally substituted aryl, or optionally substituted heteroaryl ring; wherein each occurrence of $R^{4A}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or a sulfur protecting group when attached to a sulfur atom, or two $R^{4A}$ groups are joined to form an optionally substituted heterocyclic ring; $R^5$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; and m is 0, 1, 2, 3, 4, or 5.

In certain embodiments, m is 0. In certain embodiments, m is 1. In certain embodiments, m is 2. In certain embodiments, m is 3. In certain embodiments, m is 4. In certain embodiments, m is 5.

In certain embodiments, $R_3$ is of the formula:

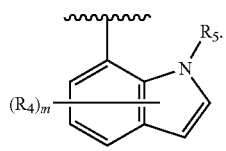

In certain embodiments, $R_3$ is of the formula:

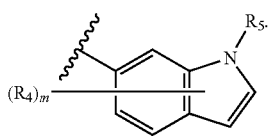

In certain embodiments, $R_3$ is of the formula:

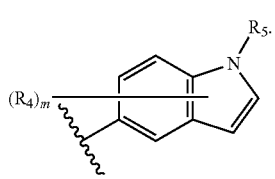

In certain embodiments, $R_3$ is of the formula:

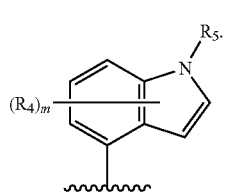

In certain embodiments, $R_3$ is of the formula:

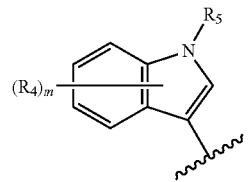

In certain embodiments, $R_3$ is of the formula:

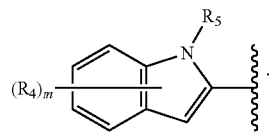

In certain embodiments, $R_4$ is halogen. In certain embodiments, $R_4$ is —F. In certain embodiments, $R_4$ is —Cl. In certain embodiments, $R_4$ is —Br. In certain embodiments, $R_4$ is —I. In certain embodiments, $R_4$ is optionally substituted, branched or unbranched $C_{1-6}$ alkyl. In certain embodiments, $R_4$ is unsubstituted methyl. In certain embodiments, $R_4$ is substituted methyl. In certain embodiments, $R_4$ is unsubstituted ethyl. In certain embodiments, $R_4$ is substituted ethyl. In certain embodiments, $R_4$ is optionally substituted propyl. In certain embodiments, $R_4$ is substituted n-propyl. In certain embodiments, $R_4$ is unsubstituted n-propyl. In certain embodiments, $R_4$ is substituted iso-propyl. In certain embodiments, $R_4$ is unsubstituted iso-propyl. In certain embodiments, $R_4$ is halogen, or optionally substituted, branched or unbranched $C_{1-6}$ alkyl, and m is 1 or 2. In certain embodiments, $R_4$ is unsubstituted methyl, and m is 1. In certain embodiments, $R_4$ is substituted methyl, and m is 1. In certain embodiments, $R_3$ is of the formula:

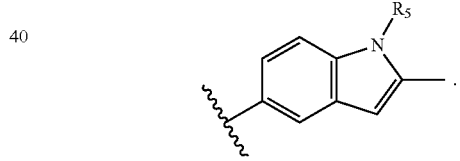

In certain embodiments, $R_3$ is of the formula:

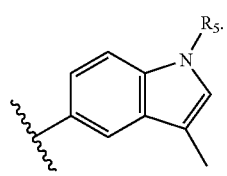

In certain embodiments, $R_3$ is of the formula:

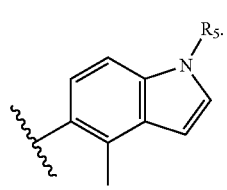

In certain embodiments, $R_3$ is of the formula:

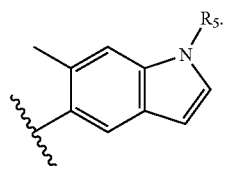

In certain embodiments, $R_3$ is of the formula:

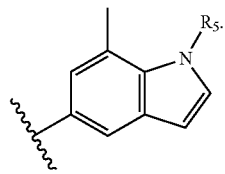

In certain embodiments, $R_4$ is F, Cl, Br, I, or $CH_3$, and m is 2. In certain embodiments, $R_3$ is of the formula:

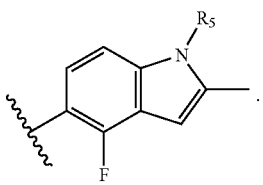

In certain embodiments, $R_3$ is of the formula:

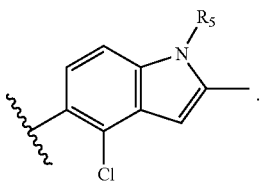

In certain embodiments, $R_3$ is of the formula:

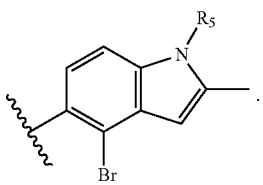

In certain embodiments, $R_3$ is of the formula:

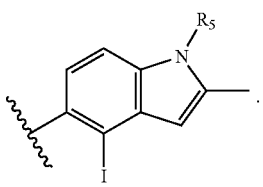

In certain embodiments, $R_5$ is hydrogen. In certain embodiments, $R_5$ is unsubstituted methyl. In certain embodiments, $R_5$ is substituted methyl. In certain embodiments, $R_5$ is unsubstituted ethyl. In certain embodiments, $R_5$ is substituted ethyl. In certain embodiments, $R_5$ is optionally substituted propyl. In certain embodiments, $R_5$ is substituted n-propyl. In certain embodiments, $R_5$ is unsubstituted n-propyl. In certain embodiments, $R_5$ is substituted iso-propyl. In certain embodiments, $R_5$ is unsubstituted iso-propyl.

In certain embodiments, $R_3$ is a monocyclic heteroaryl ring fused with another monocyclic heteroaryl ring. In certain embodiments, $R_3$ is of the formula:

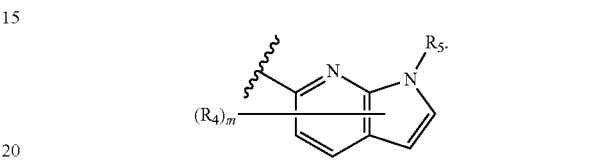

In certain embodiments, $R_3$ is of the formula:

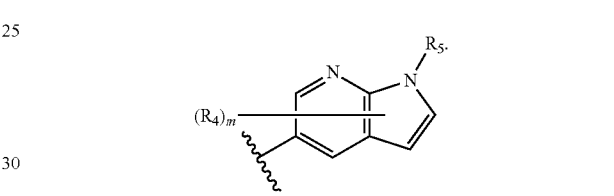

In certain embodiments, $R_4$ is halogen. In certain embodiments, $R_4$ is —F. In certain embodiments, $R_4$ is —Cl. In certain embodiments, $R_4$ is —Br. In certain embodiments, $R_4$ is —I. In certain embodiments, $R_4$ is optionally substituted, branched or unbranched $C_{1-6}$ alkyl. In certain embodiments, $R_4$ is unsubstituted methyl. In certain embodiments, $R_4$ is substituted methyl. In certain embodiments, $R_4$ is unsubstituted ethyl. In certain embodiments, $R_4$ is substituted ethyl. In certain embodiments, $R_4$ is optionally substituted propyl. In certain embodiments, $R_4$ is substituted n-propyl. In certain embodiments, $R_4$ is unsubstituted n-propyl. In certain embodiments, $R_4$ is substituted iso-propyl. In certain embodiments, $R_4$ is unsubstituted iso-propyl. In certain embodiments, $R_4$ is halogen, or optionally substituted, branched or unbranched $C_{1-6}$ alkyl, and m is 1 or 2. In certain embodiments, $R_4$ is unsubstituted methyl, and m is 1. In certain embodiments, $R_4$ is substituted methyl, and m is 1. In certain embodiments, $R_3$ is of the formula:

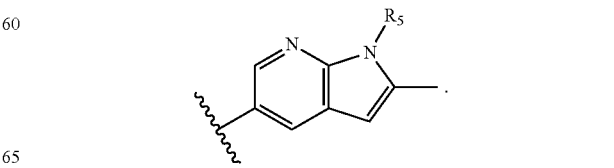

In certain embodiments, R₃ is of the formula:

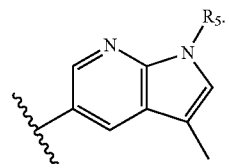

In certain embodiments, R₃ is of the formula:

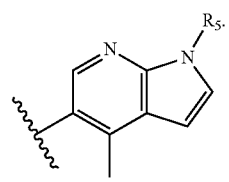

In certain embodiments, R₃ is of the formula:

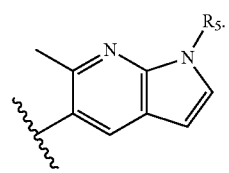

In certain embodiments, R₄ is F, Cl, Br, I, or CH₃, and m is 2. In certain embodiments, R₃ is of the formula:

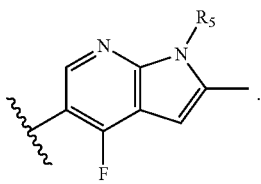

In certain embodiments, R₃ is of the formula:

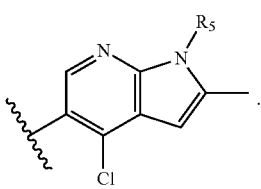

In certain embodiments, R₃ is of the formula:

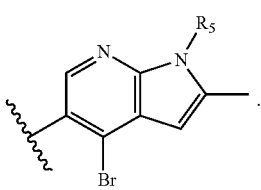

In certain embodiments, R₃ is of the formula:

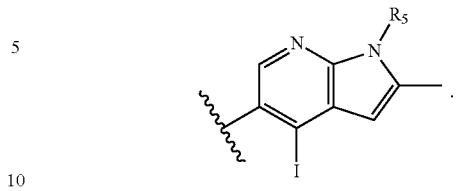

In certain embodiments, R₃ is of the formula:

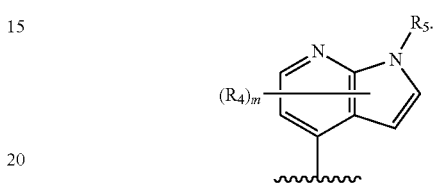

In certain embodiments, R₃ is of the formula:

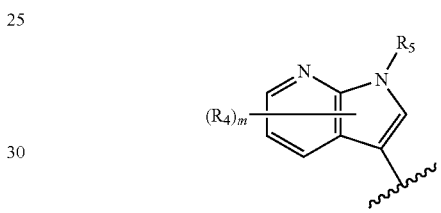

In certain embodiments, R₃ is of the formula:

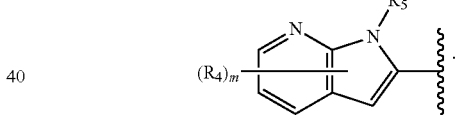

In certain embodiments, R₅ is hydrogen. In certain embodiments, R₅ is unsubstituted methyl. In certain embodiments, R₅ is substituted methyl. In certain embodiments, R₅ is unsubstituted ethyl. In certain embodiments, R₅ is substituted ethyl. In certain embodiments, R₅ is optionally substituted propyl. In certain embodiments, R₅ is substituted n-propyl. In certain embodiments, R₅ is unsubstituted n-propyl. In certain embodiments, R₅ is substituted iso-propyl. In certain embodiments, R₅ is unsubstituted iso-propyl.

In certain embodiments, R₃ is optionally substituted heteroaralkyl with at least one oxygen or nitrogen in the heteroaryl ring. In certain embodiments, R₃ is optionally substituted heterocyclylalkyl with at least one oxygen or nitrogen in the heteroaryl ring. In certain embodiments, R₃ is optionally substituted heterocyclylalkyl with 1-4 oxygen in the heteroaryl ring. In certain embodiments, R₃ is optionally substituted heterocyclylalkyl with one oxygen in the heteroaryl ring. In certain embodiments, R₃ is of the formula —(CH₂)ᵣ—Rᶻ, wherein Rᶻ is optionally substituted heterocyclyl, and r is 1, 2, 3, 4, 5, 6, 7, 8, 9, or 10. In certain embodiments, r is 1. In certain embodiments, r is 2, In certain embodiments, r is 3. In certain embodiments, r is 4. In certain embodiments, r is 5. In certain embodiments, r is 6. In certain embodiments, r is 7. In certain embodiments, r is 8. In certain embodiments, r is 9. In certain embodiments, r is 10. In certain embodiments, $R^z$ is optionally substituted heterocyclyl with 1-4 oxygen. In certain embodiments, $R^z$ is of the formula:

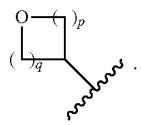

In certain embodiments, p is 1, and q is 1. In certain embodiments, p is 1, and q is 2. In certain embodiments, p is 1, and q is 3. In certain embodiments, p is 1, and q is 4. In certain embodiments, p is 2, and q is 2. In certain embodiments, p is 2, and q is 3. In certain embodiments, p is 2, and q is 4. In certain embodiments, p is 3, and q is 3. In certain embodiments, p is 3, and q is 4. In certain embodiments, p is 4, and q is 4. In certain embodiments, $R^z$ is of the formula

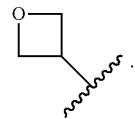

In certain embodiments, $R_3$ is of the formula

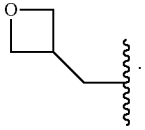

In compounds of Formula (I), Y is N or CH. In certain embodiments, Y is N. In certain embodiments, Y is CH.

In compounds of Formula (I), linker X is a divalent linker moiety. X may contain 0-4 carbon atoms or hetero atoms in the backbone of X. X may be substituted or unsubstituted. X may be branched or unbranched. In certain embodiments, X is a bond. In certain embodiments, X is —C(=O)—. In certain embodiments, X is —O—. In certain embodiments, X is —S—. In certain embodiments, X is a substituted $C_{1-6}$ alkylene. In certain embodiments, X is an unsubstituted $C_{1-6}$ alkylene. In certain embodiments, X is —$CH_2$—. In certain embodiments, X is —$(CH_2)_2$—. In certain embodiments, X is —$(CH_2)_3$—. In certain embodiments, X is —$(CH_2)_4$—. In certain embodiments, X is —$(CH_2)_5$—. In certain embodiments, X is —$(CH_2)_6$—. In certain embodiments, X is an optionally substituted $C_{1-6}$ hydrocarbon chain, wherein one or more carbon units of the hydrocarbon chain is replaced with —O—, —S—, —$NR^{Xa}$—, —$NR^{Xa}C(=O)$—, —$C(=O)NR^{Xa}$—, —$SC(=O)$—, —$C(=O)S$—, —$OC(=O)$—, —$C(=O)O$—, —$NR^{Xa}C(=S)$—, —$C(=S)NR^{Xa}$—, trans-$CR^{Xb}=CR^{Xb}$—, cis-$CR^{Xb}=CR^{Xb}$—, —C≡C—, —$S(=O)_2O$—, —$OS(=O)_2$—, —$S(=O)_2NR^{Xa}$—, or —$NR^{Xa}S(=O)_2$—, wherein $R^{Xa}$ is optionally substituted alkyl or a nitrogen protectin group; and $R^{Xb}$ is optionally substituted alkyl. In certain embodiments, X is —$(C=O)(CH_2)_5$—. In certain embodiments, X is —$(C=O)(CH_2)_4$—. In certain embodiments, X is —$(C=O)(CH_2)_3$—. In certain embodiments, X is —$(C=O)(CH_2)_2$—. In certain embodiments, X is —$(C=O)CH_2$—. In certain embodiments, X is —$O(CH_2)_5$—. In certain embodiments, X is —$O(CH_2)_4$—. In certain embodiments, X is —$O(CH_2)_3$—. In certain embodiments, X is —$O(CH_2)_2$—. In certain embodiments, X is —$OCH_2$—.

As defined generally above, $R_2$ is optionally substituted carbocyclyl, optionally substituted heterocyclyl, optionally substituted aryl, or optionally substituted heteroaryl. In certain embodiments, $R_2$ is unsubstituted. In certain embodiments, $R_2$ is substituted with one, two, or three $R_4$ groups. In certain embodiments, $R_2$ is an optionally substituted monocyclic or bicyclic carbocyclic ring. In certain embodiments, $R_2$ is an optionally substituted monocyclic or bicyclic heterocyclic ring with 0-4 heteroatoms independently selected from nitrogen, oxygen, and sulfur. In certain embodiments, $R_2$ is an optionally substituted monocyclic or bicyclic heteroaryl ring.

In certain embodiments, $R_2$ is an optionally substituted monocyclic hetero-ring with 1-4 oxygen. In certain embodiments, $R_2$ is an optionally substituted monocyclic ring with one oxygen. In certain embodiments, $R_2$ is of the formula

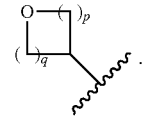

In certain embodiments, p is 0, and $R_2$ is hydroxyl alkyl. In certain embodiments, p is 1. In certain embodiments, p is 2. In certain embodiments, p is 3. In certain embodiments, p is 4. In certain embodiments, q is 0, and $R_2$ is hydroxyalkyl. In certain embodiments, q is 1. In certain embodiments, q is 2. In certain embodiments, q is 3. In certain embodiments, q is 4. In certain embodiments, p is 1; and q is 1. In certain embodiments, p is 1; and q is 2. In certain embodiments, when p is 1; and q is 3. In certain embodiments, p is 1; and q is 4. In certain embodiments, p is 2; and q is 2. In certain embodiments, p is 2; and q is 3. In certain embodiments, p is 2; and q is 4. In certain embodiments, p is 3; and q is 3. In certain embodiments, p is 3; and q is 4. In certain embodiments, p is 4; and q is 4. In certain embodiments, $R_2$ is of the formula:

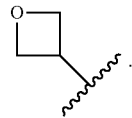

In certain embodiments, $R_2$ is of the formula:

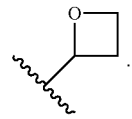

In certain embodiments, R₂ is of the formula:

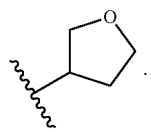 [SMILES: *C1CCOC1]

In certain embodiments, R₂ is of the formula:

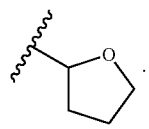 [SMILES: *C1CCCO1]

In certain embodiments, R₂ is of the formula:

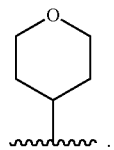

In certain embodiments, R₂ is of the formula:

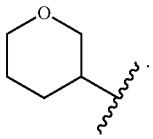 [SMILES: *C1CCCOC1]

In certain embodiments, R₂ is of the formula:

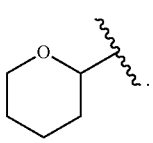 [SMILES: *C1CCCCO1]

In certain embodiments, R₂ is an optionally substituted bicyclic hetero-ring with 1-4 heteroatoms independently selected from nitrogen and oxygen. In certain embodiments, R₂ is an optionally substituted bicyclic heterocyclic ring with one nitrogen and one oxygen. In certain embodiments, R₂ is of the formula

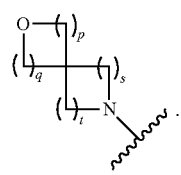

In certain embodiments, p is 1; q is 1; s is 1; and t is 1. In certain embodiments, p is 1; q is 1; s is 1; and t is 2. In certain embodiments, when p is 1; q is 1; s is 1; and t is 3. In certain embodiments, p is 1; q is 1; s is 2; and t is 2. In certain embodiments, p is 1; q is 1; s is 2; and t is 3. In certain embodiments, p is 1; q is 1; s is 3; and t is 3. In certain embodiments, p is 1; q is 1; s is 1; and t is 1. In certain embodiments, p is 1; q is 2; s is 1; and t is 2. In certain embodiments, p is 1; q is 2; s is 1; and t is 3. In certain embodiments, p is 1; q is 2; s is 2; and t is 2. In certain embodiments, p is 1; q is 2; s is 2; and t is 3. In certain embodiments, p is 1; q is 2; s is 3; and t is 3. In certain embodiments, p is 2; q is 2; s is 1; and t is 1. In certain embodiments, p is 2; q is 2; s is 1; and t is 2. In certain embodiments, p is 2; q is 2; s is 1; t is 3. In certain embodiments, p is 2; q is 2; s is 2; and t is 2. In certain embodiments, p is 2; q is 2; s is 2; and t is 3. In certain embodiments, p is 2; q is 2; s is 3; and t is 3. In certain embodiments, R₂ is of one of the following formulae:

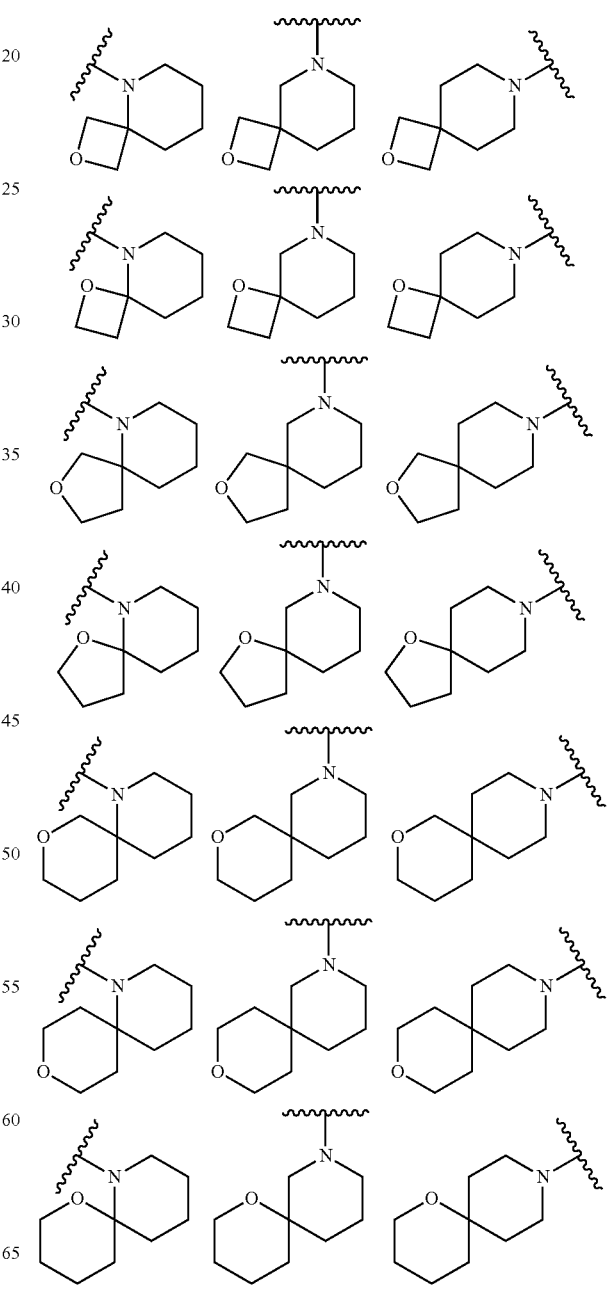

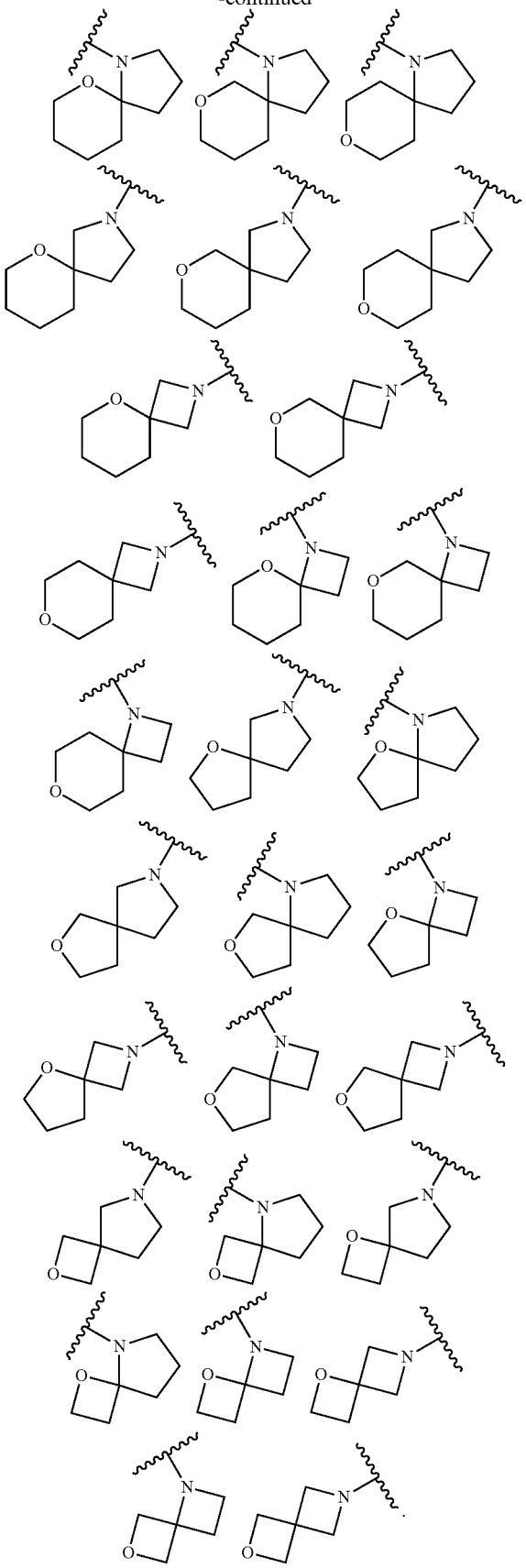

In certain embodiments, R₂ is of the formula:

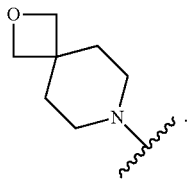 [SMILES: *N1CCC2(CC1)COC2]

In certain embodiments, R₂ is of the formula:

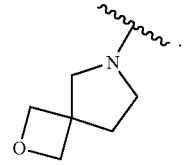 [SMILES: *N1CCC2(COC2)C1]

In certain embodiments, R₂ is of the formula:

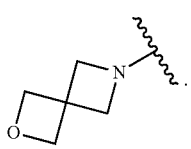 [SMILES: *N1CC2(COC2)C1]

In certain embodiments, $R_1$ is hydrogen. In certain embodiments, $R_1$ is optionally substituted, branched or unbranched, $C_{1-6}$ alkyl. In certain embodiments, $R_1$ is substituted methyl. In certain embodiments, $R_1$ is unsubstituted methyl. In certain embodiments, $R_1$ is substituted ethyl. In certain embodiments, $R_1$ is unsubstituted ethyl. In certain embodiments, $R_1$ is substituted n-propyl. In certain embodiments, $R_1$ is unsubstituted n-propyl. In certain embodiments, $R_1$ is substituted iso-propyl. In certain embodiments, $R_1$ is unsubstituted iso-propyl.

In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10.

In certain embodiments, the compound of Formula (I) is of the Formula (II):

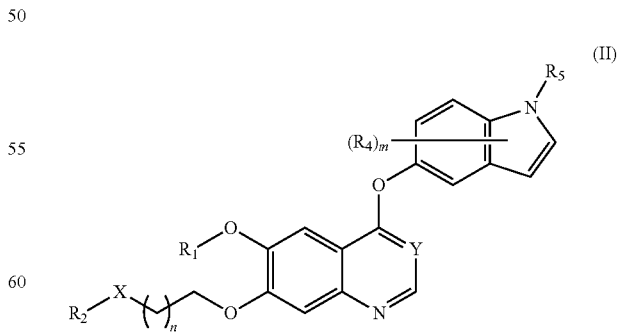

(II)

or a pharmaceutically acceptable salt, solvate, hydrate, polymorph, co-crystal, tautomer, stereoisomer, isotopically labeled derivative, or prodrug thereof, wherein $R_1$, $R_2$, $R_4$, $R_5$, X, Y, m, and n are as defined herein.

In certain embodiments, the compound of Formula (I) is of the Formula (II-a):

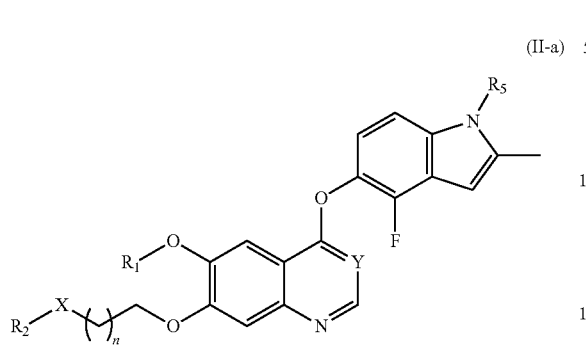

or a pharmaceutically acceptable salt, solvate, hydrate, polymorph, co-crystal, tautomer, stereoisomer, isotopically labeled derivative, or prodrug thereof, wherein $R_1$, $R_2$, $R_5$, X, Y, and n are as defined herein.

In certain embodiments, the compound of Formula (I) is of the Formula (II-b):

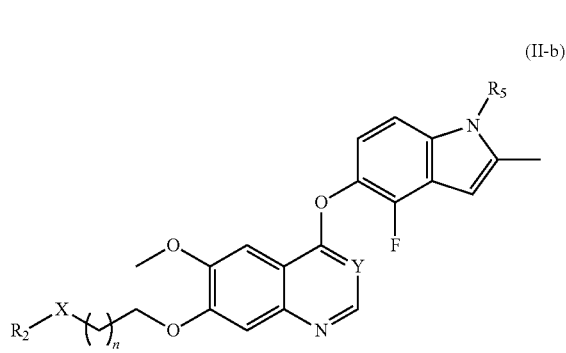

or a pharmaceutically acceptable salt, solvate, hydrate, polymorph, co-crystal, tautomer, stereoisomer, isotopically labeled derivative, or prodrug thereof, wherein $R_2$, $R_5$, X, Y, and n are as defined herein.

In certain embodiments, the compound of Formula (I) is of the Formula (II-b1):

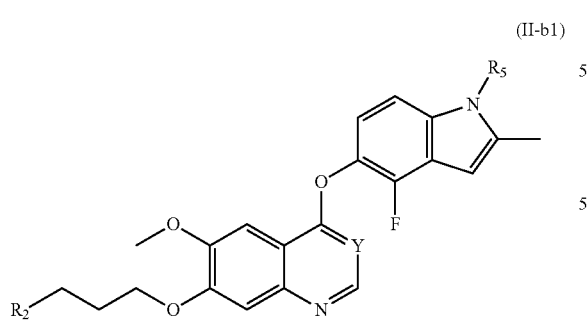

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (II-b2):

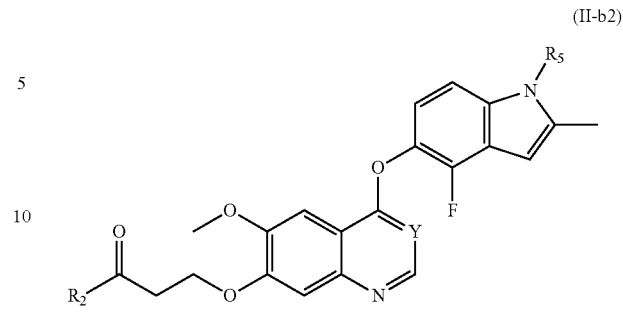

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (II-b3):

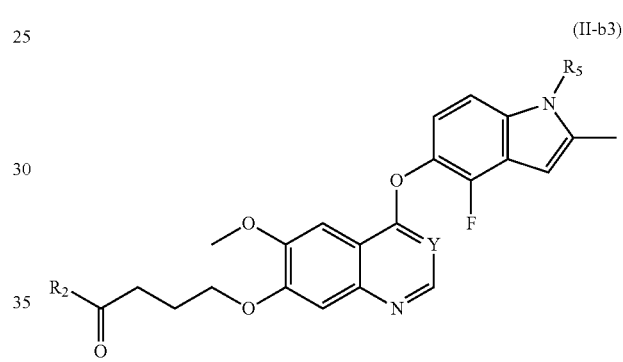

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (II-b4):

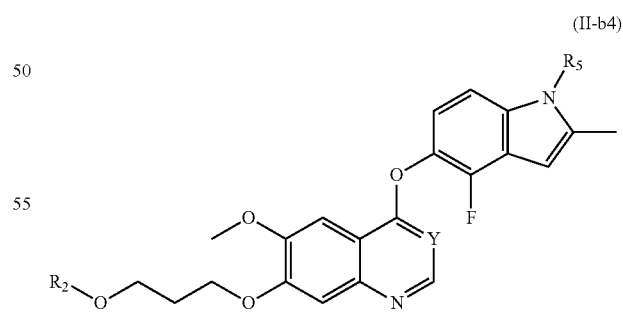

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (II-c):

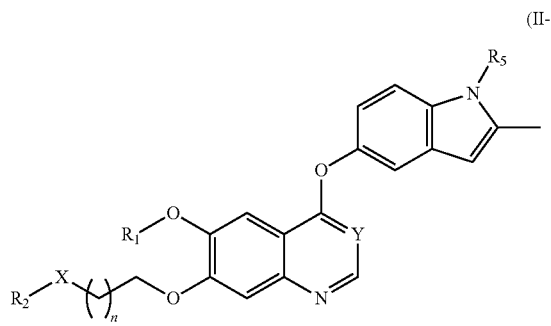

(II-c)

or a pharmaceutically acceptable salt, solvate, hydrate, polymorph, co-crystal, tautomer, stereoisomer, isotopically labeled derivative, or prodrug thereof, wherein $R_1$, $R_2$, $R_5$, X, Y, and n are as defined herein.

In certain embodiments, the compound of Formula (I) is of the Formula (II-d):

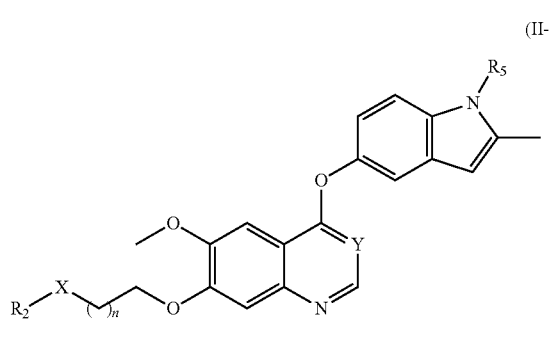

(II-d)

or a pharmaceutically acceptable salt, solvate, hydrate, polymorph, co-crystal, tautomer, stereoisomer, isotopically labeled derivative, or prodrug thereof, wherein $R_2$, $R_5$, X, Y, and n are as defined herein.

In certain embodiments, the compound of Formula (I) is of the Formula (II-d1):

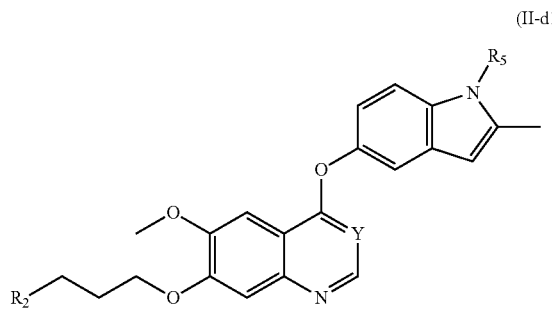

(II-d1)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (II-d2):

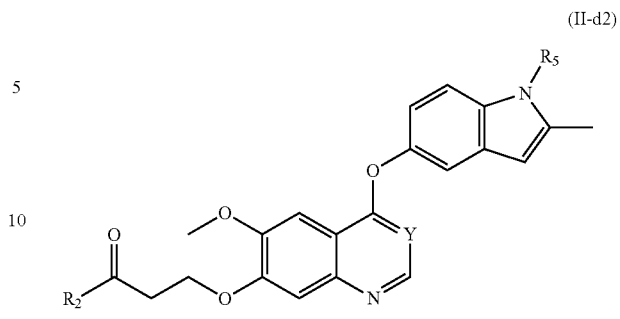

(II-d2)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (II-d3):

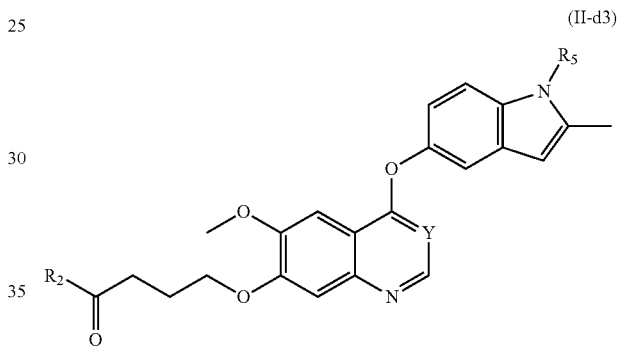

(II-d3)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (II-d4):

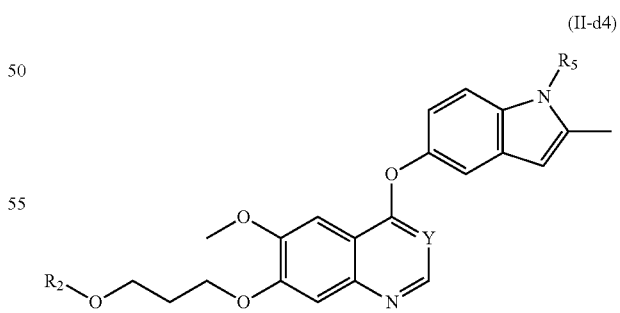

(II-d4)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (III):

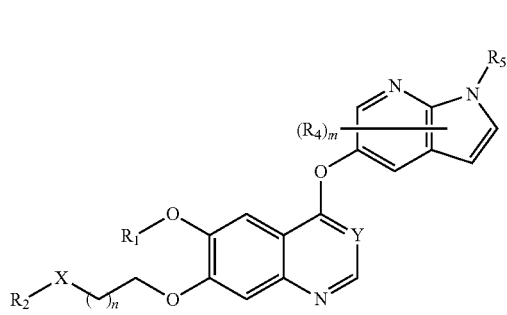

(III)

or a pharmaceutically acceptable salt thereof, wherein $R_1$, $R_2$, $R_4$, $R_5$, X, Y, m, and n are as defined herein.

In certain embodiments, the compound of Formula (I) is of the Formula (III-a):

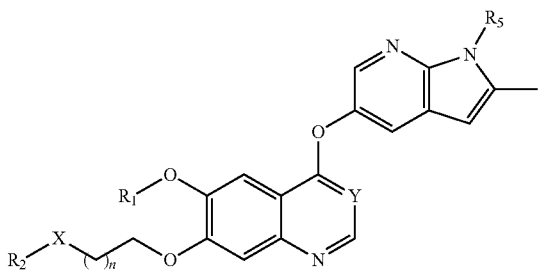

(III-a)

or a pharmaceutically acceptable salt, solvate, hydrate, polymorph, co-crystal, tautomer, stereoisomer, isotopically labeled derivative, or prodrug thereof, wherein $R_1$, $R_2$, $R_5$, X, Y, and n are as defined herein.

In certain embodiments, the compound of Formula (I) is of the Formula (III-b):

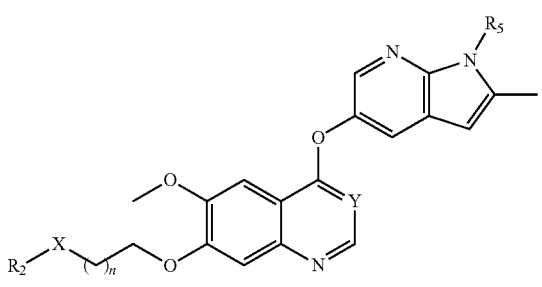

(III-b)

or a pharmaceutically acceptable salt, solvate, hydrate, polymorph, co-crystal, tautomer, stereoisomer, isotopically labeled derivative, or prodrug thereof, wherein $R_2$, $R_5$, X, Y, and n are as defined herein.

In certain embodiments, the compound of Formula (I) is of the Formula (III-b1):

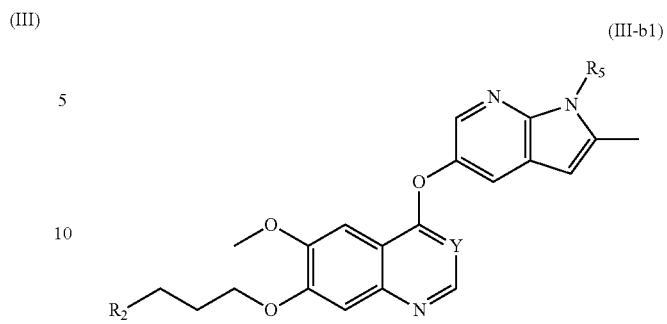

(III-b1)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (III-b2):

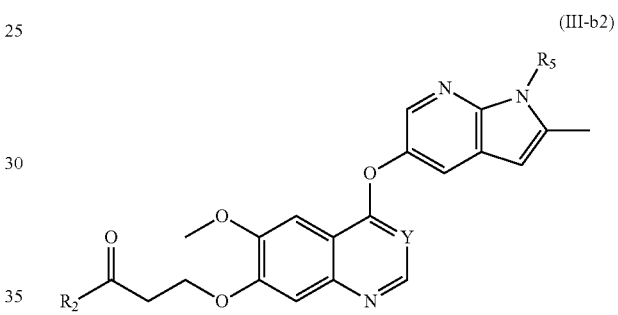

(III-b2)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as described herein.

In certain embodiments, the compound of Formula (I) is of the Formula (III-b3):

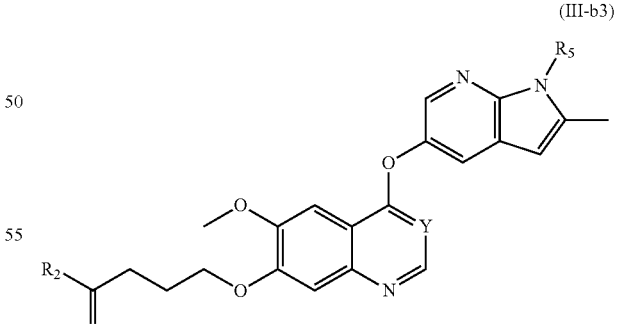

(III-b3)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as described herein.

In certain embodiments, the compound of Formula (I) is of the Formula (III-b4):

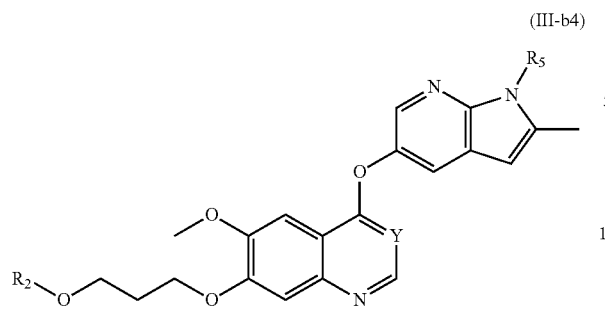

(III-b4)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as described herein.

In certain embodiments, the compound of Formula (I) is of the Formula (III-c):

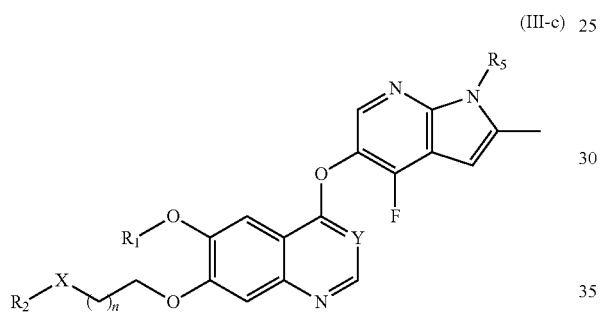

(III-c)

or a pharmaceutically acceptable salt, solvate, hydrate, polymorph, co-crystal, tautomer, stereoisomer, isotopically labeled derivative, or prodrug thereof, wherein $R_1$, $R_2$, $R_5$, X, Y, and n are as defined herein.

In certain embodiments, the compound of Formula (I) is of the Formula (III-d):

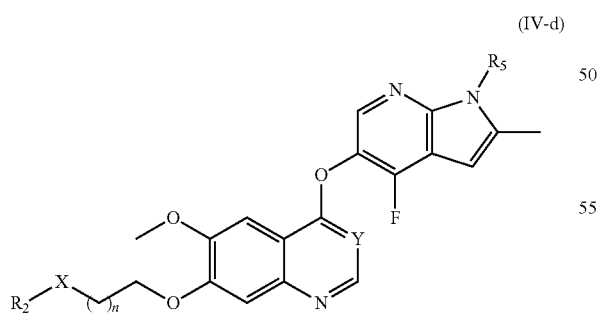

(IV-d)

or a pharmaceutically acceptable salt, solvate, hydrate, polymorph, co-crystal, tautomer, stereoisomer, isotopically labeled derivative, or prodrug thereof, wherein $R_2$, $R_5$, X, Y, and n are as defined herein.

In certain embodiments, the compound of Formula (I) is of the Formula (III-d1):

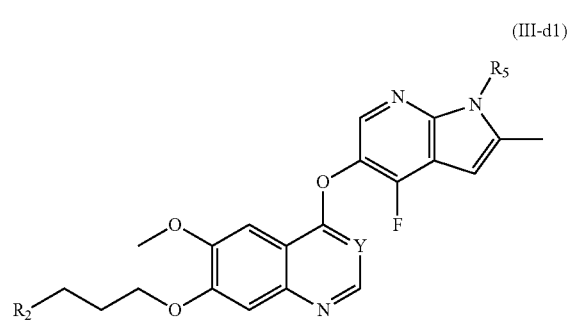

(III-d1)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (III-d2):

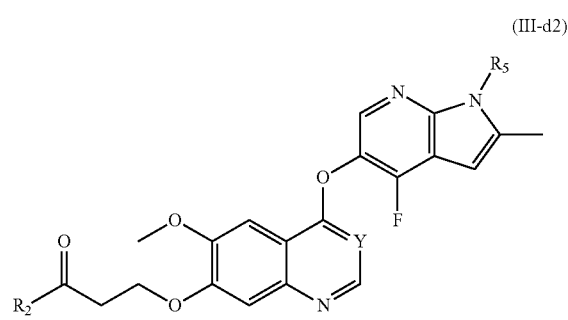

(III-d2)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (III-d3):

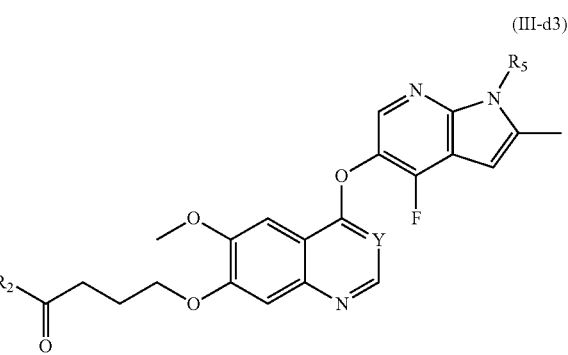

(III-d3)

or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.

In certain embodiments, the compound of Formula (I) is of the Formula (III-d4):

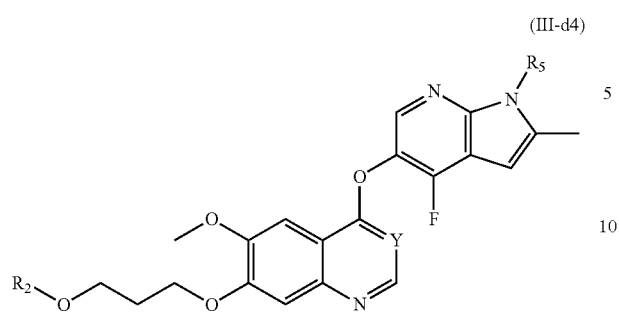
(III-d4)
or a pharmaceutically acceptable salt, solvate, hydrate, polymorph, co-crystal, tautomer, stereoisomer, isotopically labeled derivative, or prodrug thereof, wherein $R_2$, $R_5$, and Y are as defined herein.
Exemplary compounds of Formulae (I)-(III) include, but are not limited to:
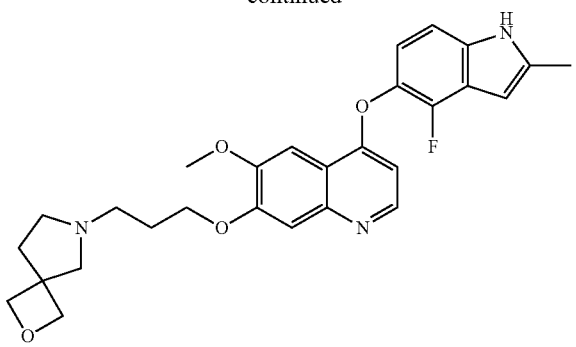
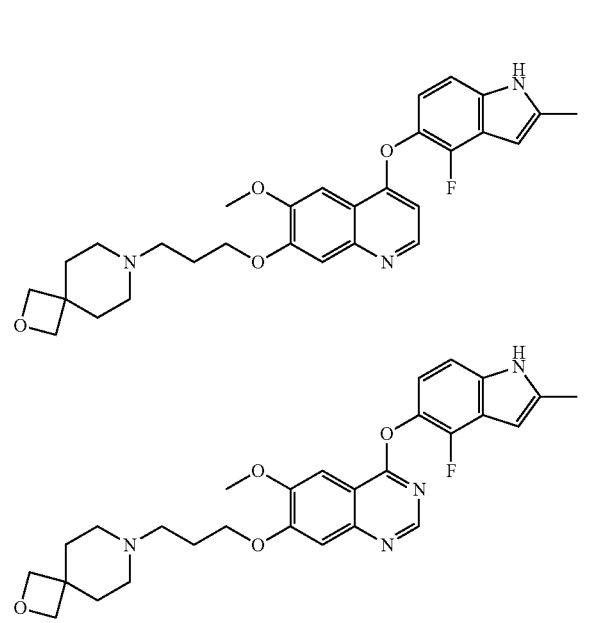
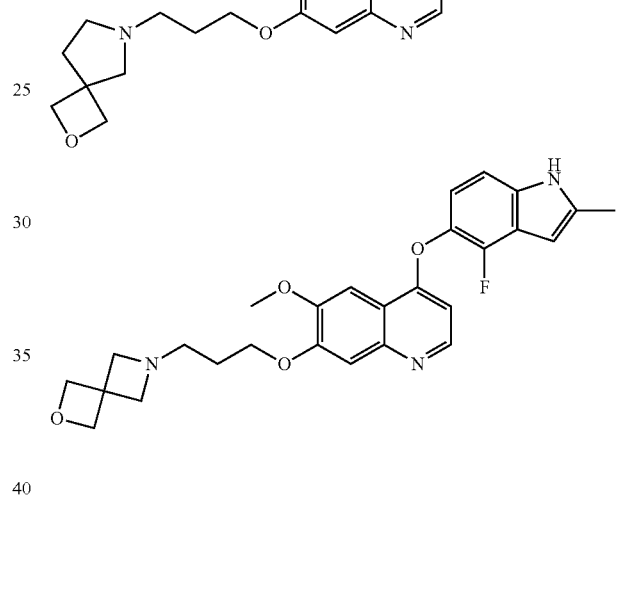
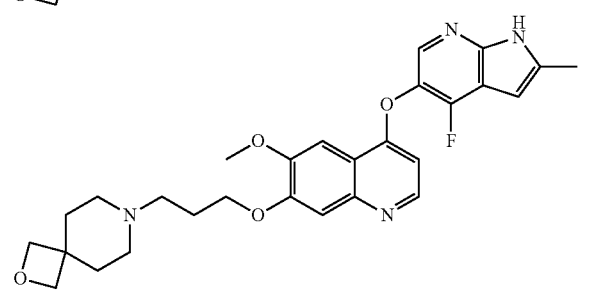
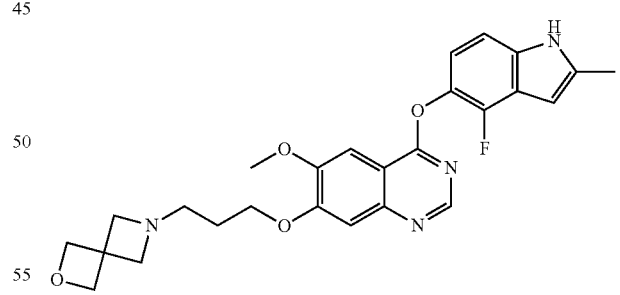
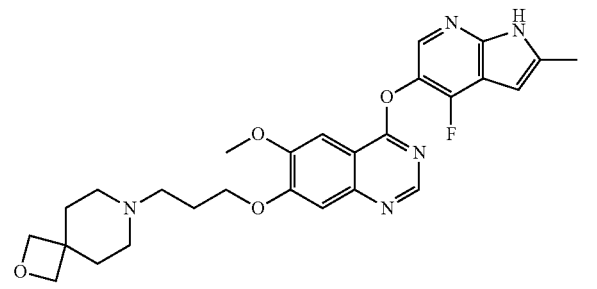
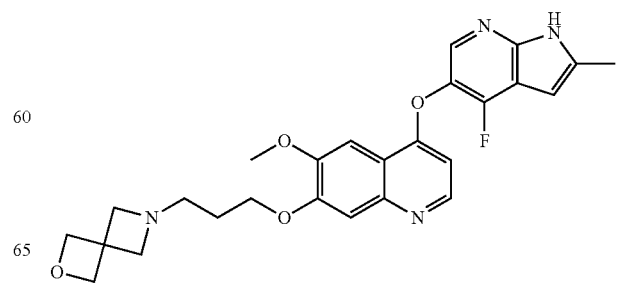

65
-continued
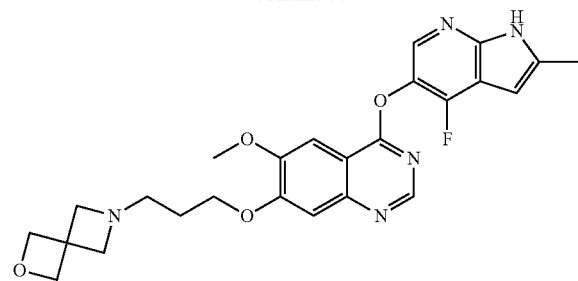
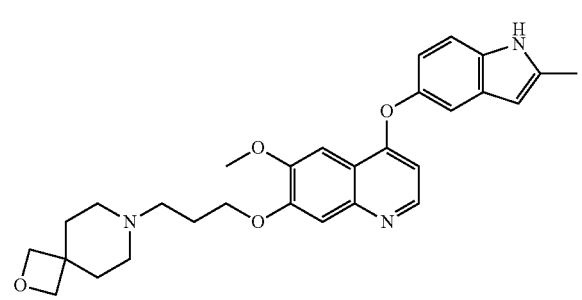
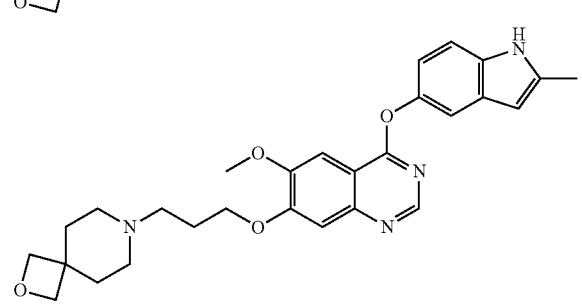
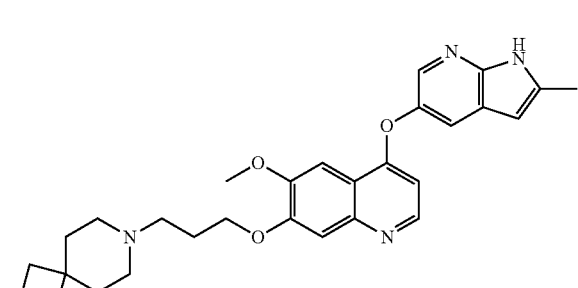
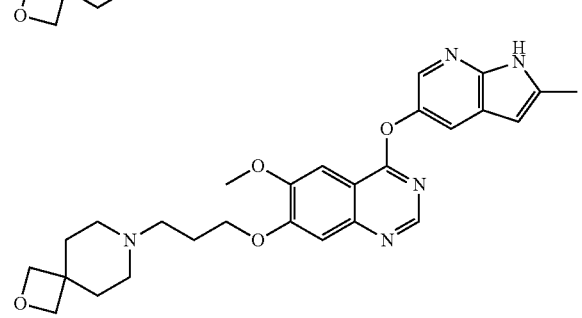
66
-continued
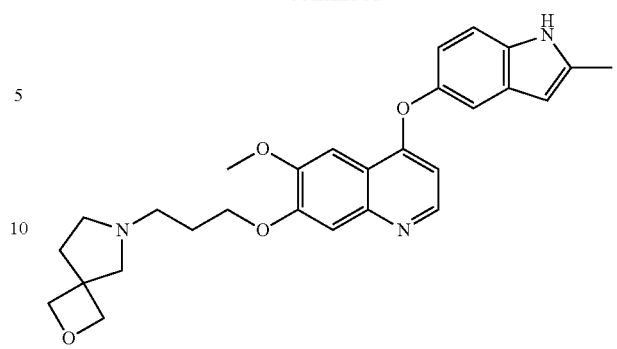
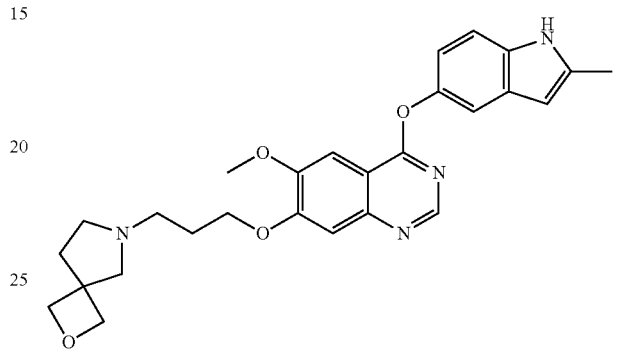
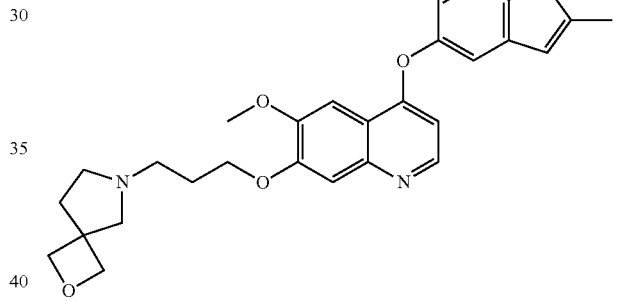
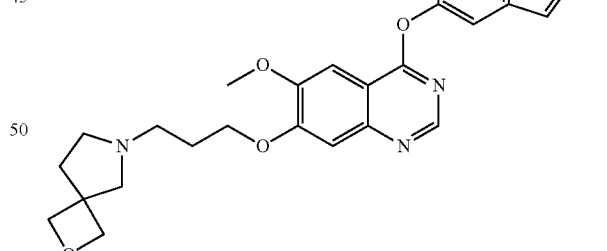
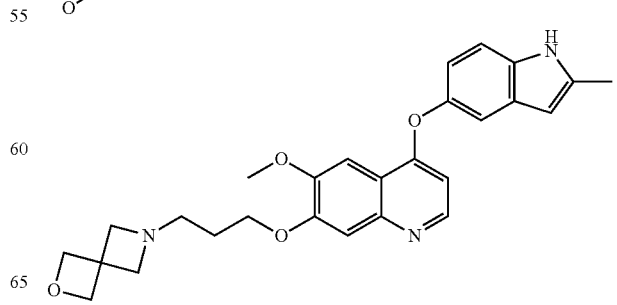

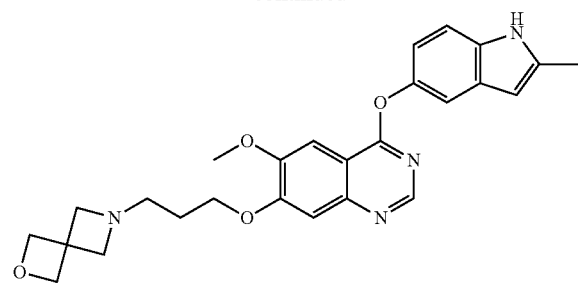
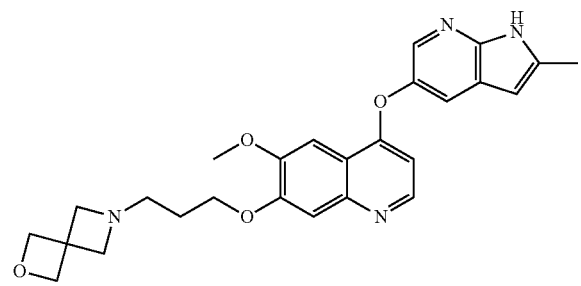
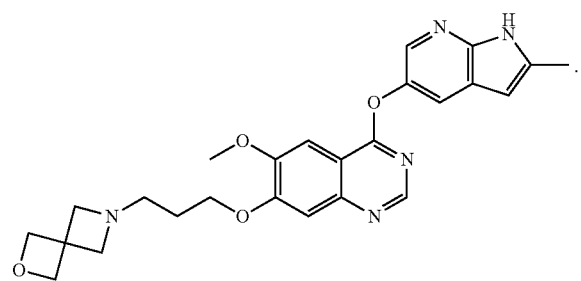
Other exemplary compounds of Formulae (I)-(III) include, but are not limited to:
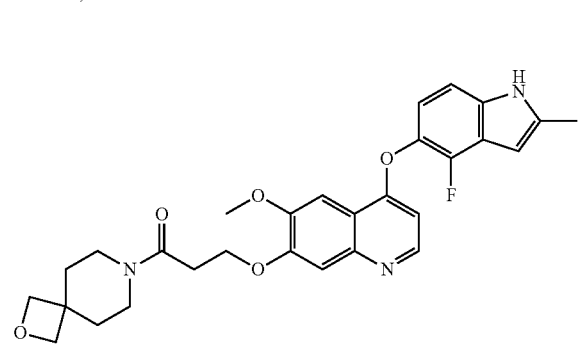
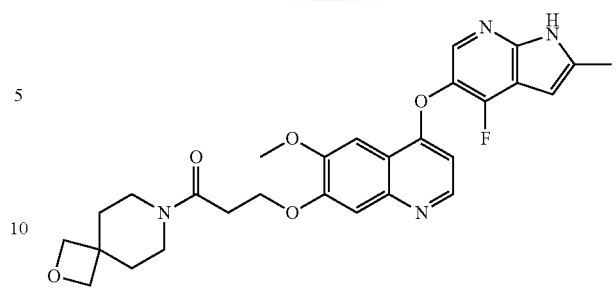
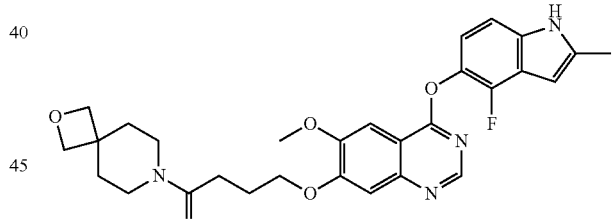
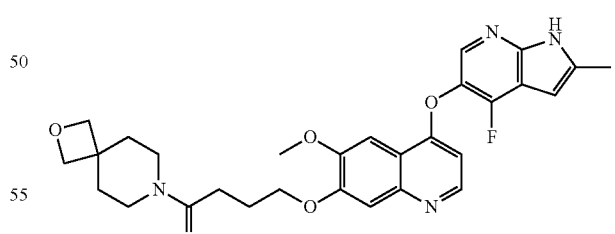
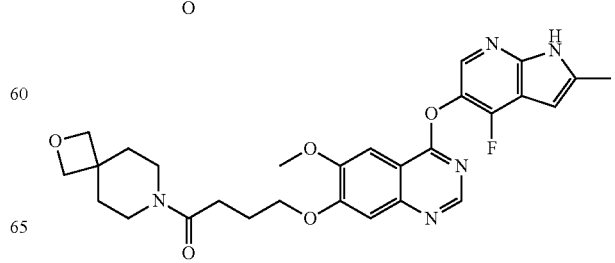

69
-continued
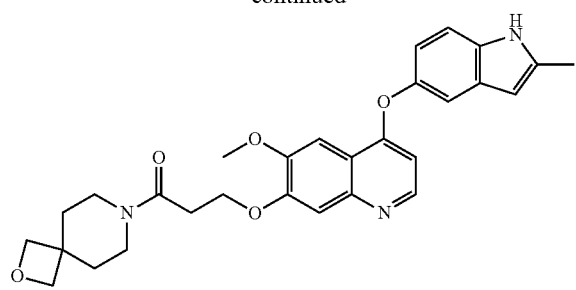
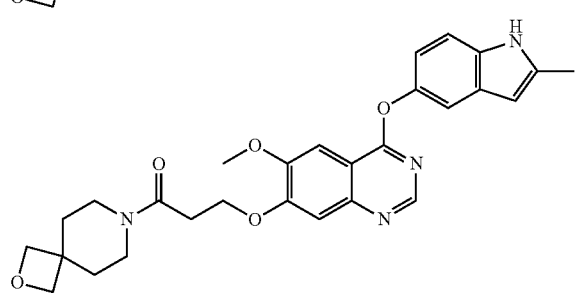
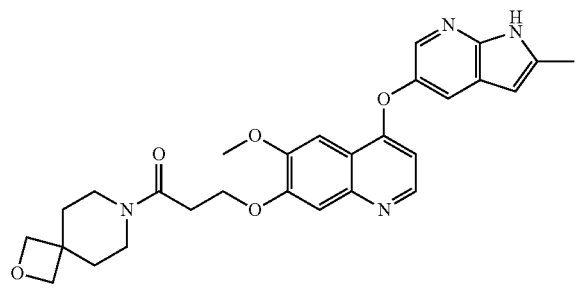
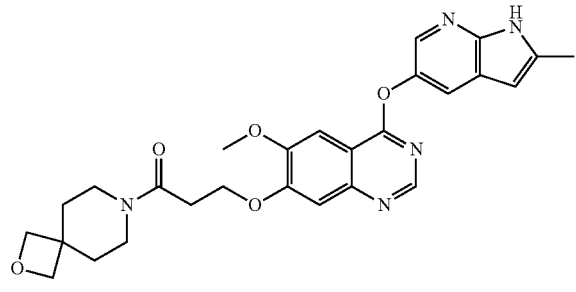
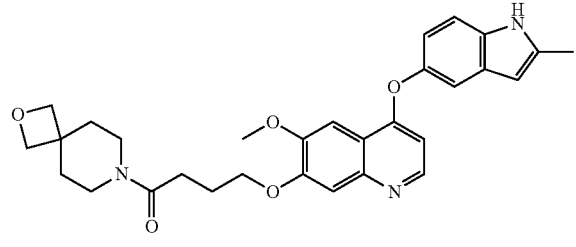
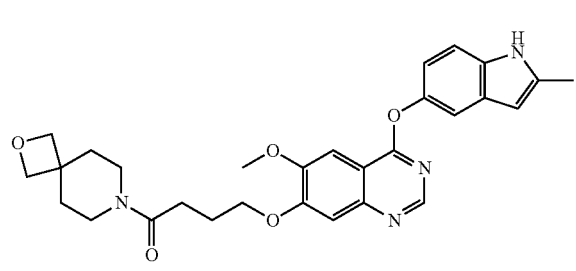
70
-continued
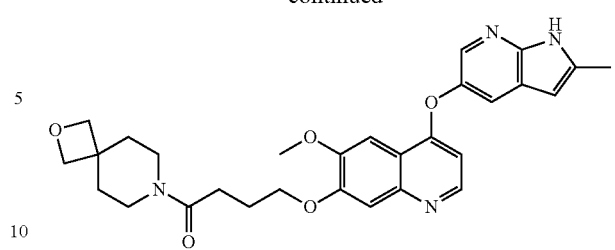
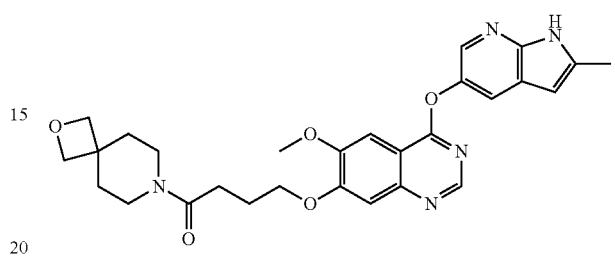
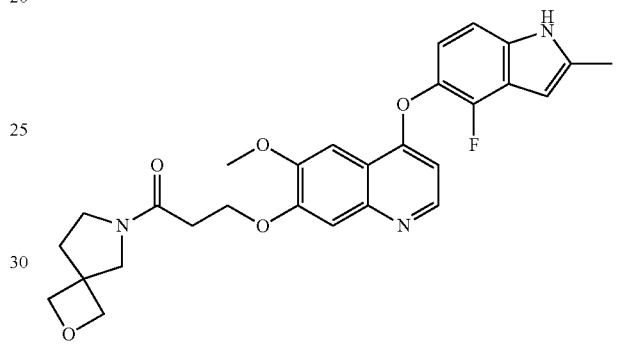
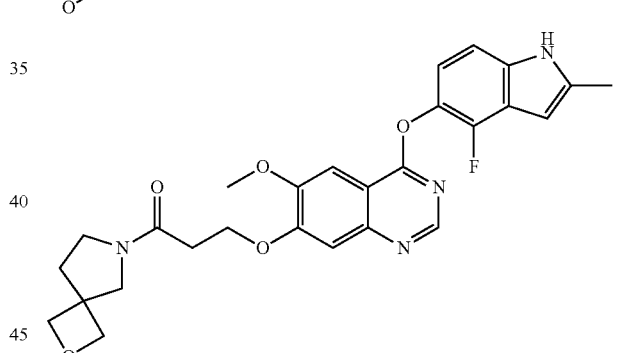
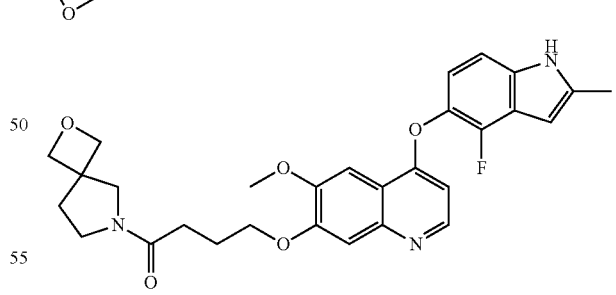
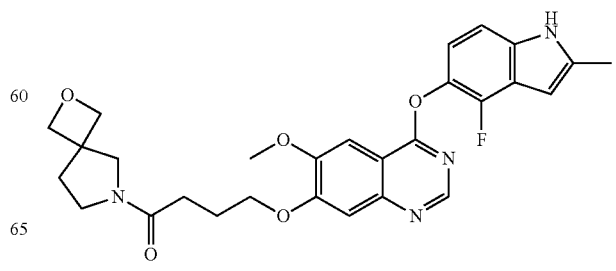

71
-continued
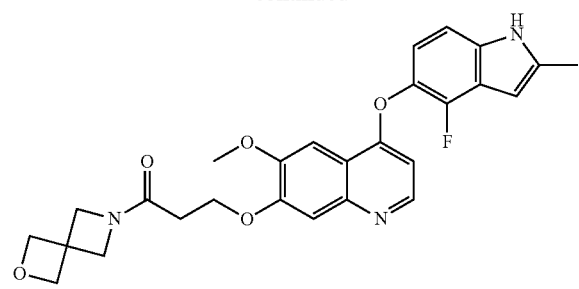
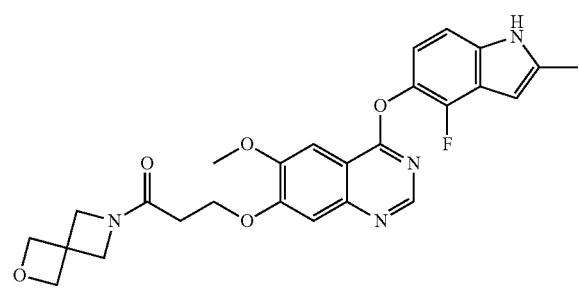
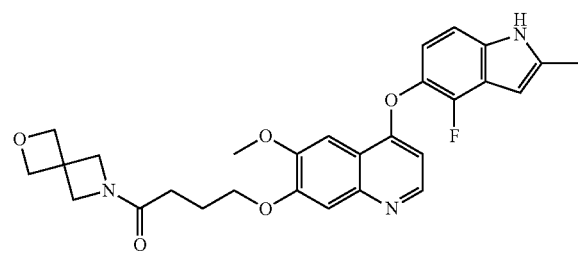
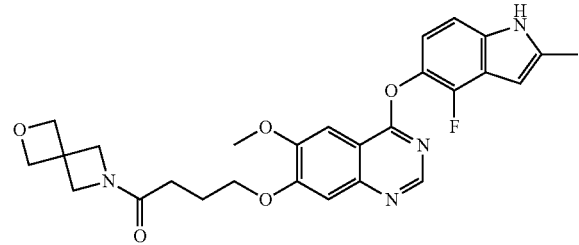
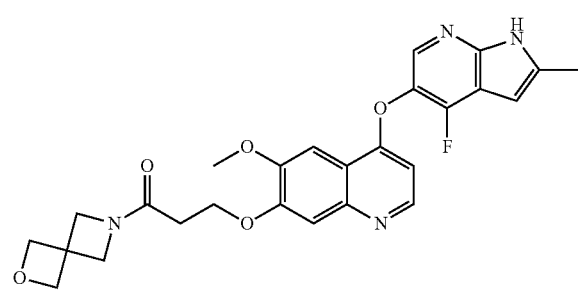
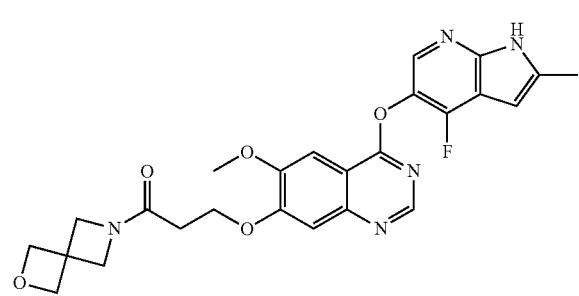
72
-continued
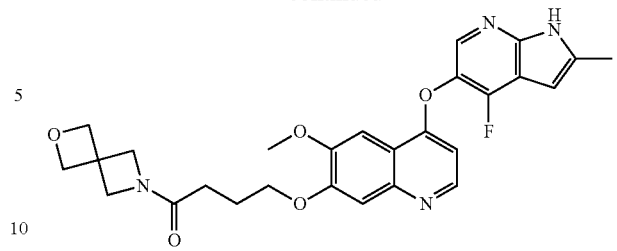
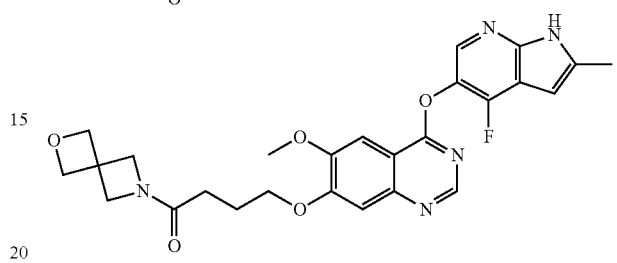
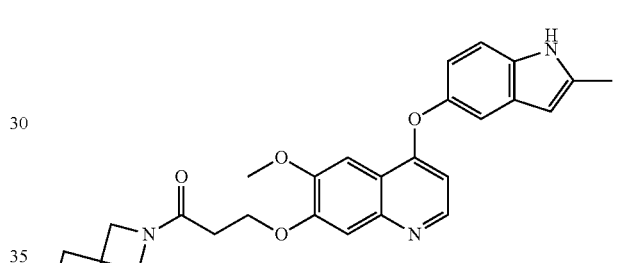
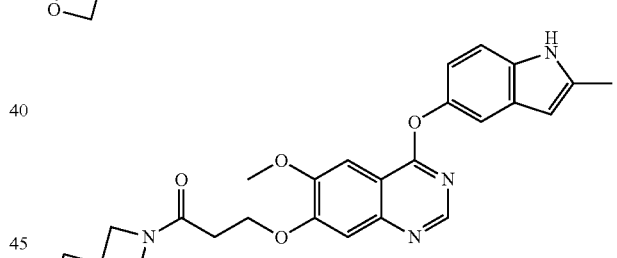
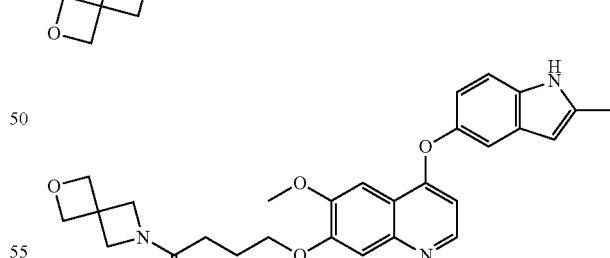
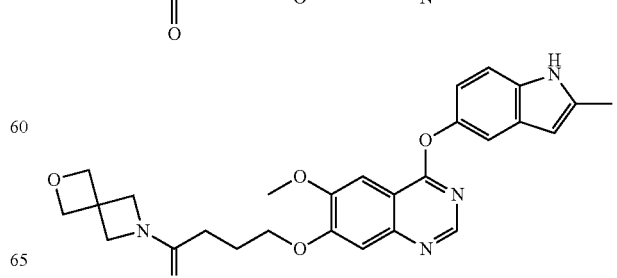

-continued

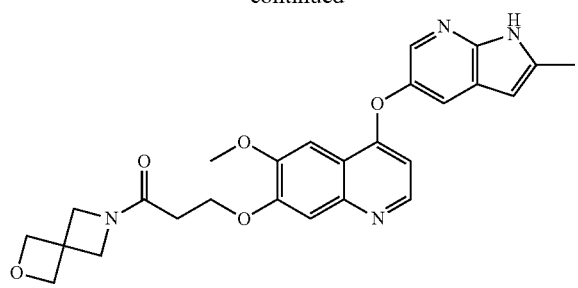

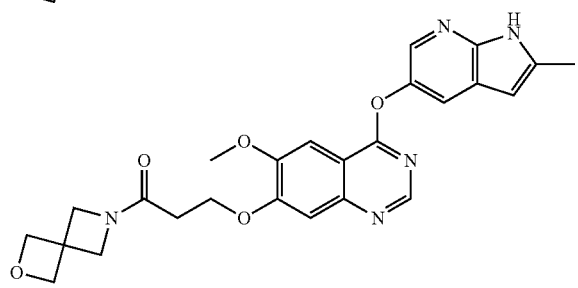

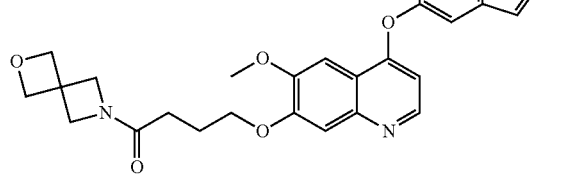

In certain embodiments, the compound of the invention is

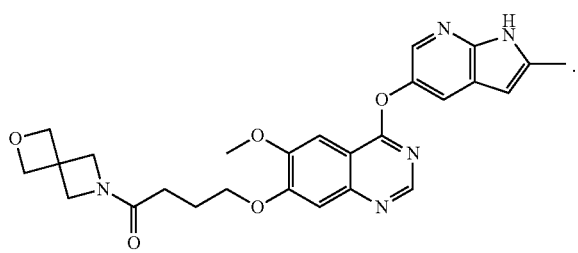

or a pharmaceutically acceptable salt, solvate, hydrate, polymorph, co-crystal, tautomer, stereoisomer, isotopically labeled derivative, or prodrug thereof.

In certain embodiments, the compound of the invention is

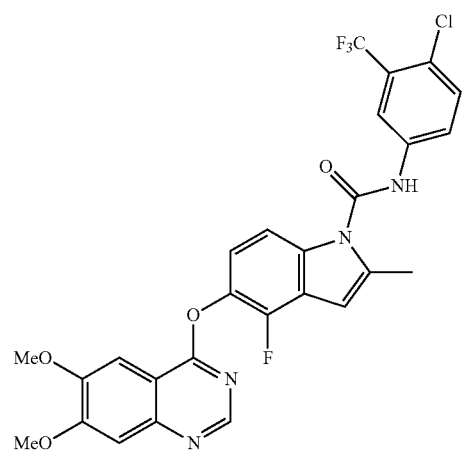 [SMILES: COc1cc2ncnc(Oc3ccc4c(cc(C)n4C(=O)Nc4ccc(Cl)c(C(F)(F)F)c4)c3F)c2cc1OC]

or a pharmaceutically acceptable salt, solvate, hydrate, polymorph, co-crystal, tautomer, stereoisomer, isotopically labeled derivative, or prodrug thereof.

Other exemplary compounds of the invention include, but are not limited to;

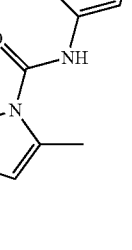

-continued

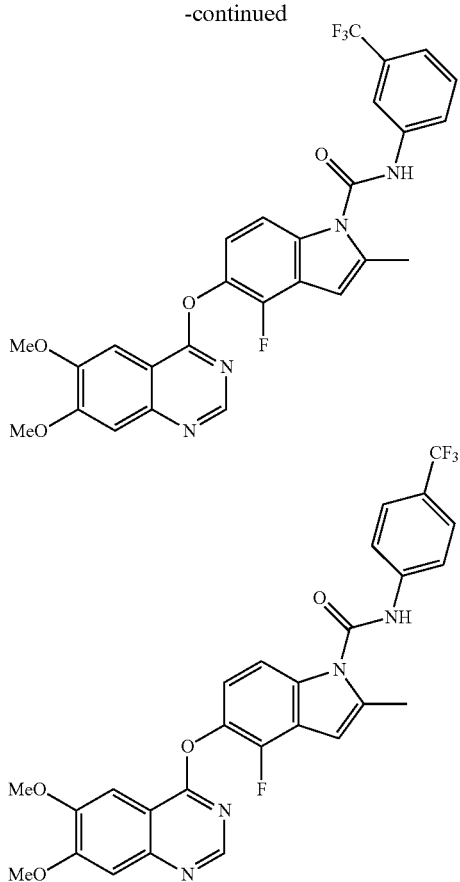

Compounds of the invention may be crystalline. In certain embodiments, the compounds of the invention are monocrystalline. In certain embodiments, the compounds of the invention are polycrystalline.

Compounds of the invention may also have a relatively low aqueous solubility (i.e., a solubility in water, optionally with one or more buffers). For example, compounds of the invention may have an aqueous solubility of less than about or equal to about 3 mg/mL, less than about 1 mg/mL, less than about 0.3 mg/mL, less than about 0.1 mg/mL, less than about 0.03 mg/mL, less than about 0.01 mg/mL, less than about 1 μg/mL, less than about 0.1 μg/mL, less than about 0.01 μg/mL, less than about 1 ng/mL, less than about 0.1 ng/mL, or less than about 0.01 ng/mL at 25° C. In some embodiments, the compounds of the invention have an aqueous solubility of at least about 1 μg/mL, at least about 10 μg/mL, at least about 0.1 ng/mL, at least about 1 ng/mL, at least about 10 ng/mL, at least about 0.1 μg/mL, at least about 1 μg/mL, at least about 3 μg/mL, at least about 0.01 mg/mL, at least about 0.03 mg/mL, at least about 0.1 mg/mL, at least about 0.3 mg/mL, at least about 1.0 mg/mL, or at least about 3 mg/mL at 25° C. Combinations of the above-noted ranges are possible (e.g., an aqueous solubility of at least about 10 pg/mL and less than about 1 mg/mL). Other ranges are also possible. The compounds of the invention may have these or other ranges of aqueous solubilities at any point throughout the pH range (e.g., at about pH 7 or from pH 1 to pH 14).

Compounds of the invention may be suitable for being processed into mucus penetrating pharmaceutical compositions (e.g., particles or crystals). In certain embodiments, the compounds of the invention are suitable for milling (e.g., nano-milling). In certain embodiments, the compounds of the invention are suitable for precipitation (e.g., microprecipitation, nanoprecipitation, crystallization, or controlled crystallization). In certain embodiments, the compounds of the invention are suitable for emulsification. In certain embodiments, the compounds of the invention are suitable for freeze-drying.

Synthetic Methods

In some embodiments, compounds described herein can be prepared using methods shown in Scheme 1:

Scheme 1

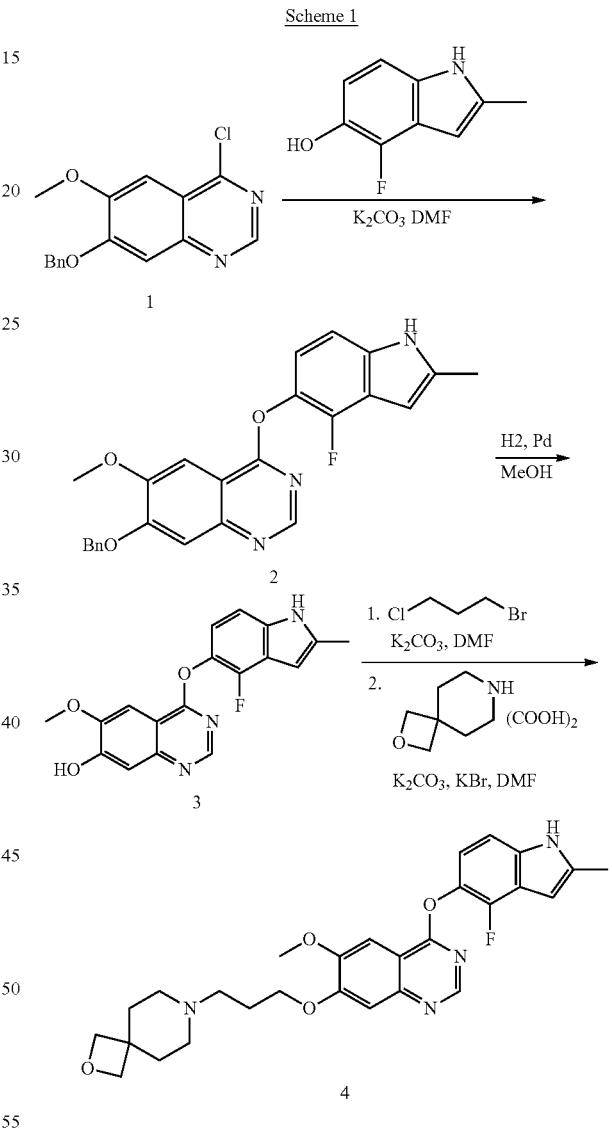

Pharmaceutical Compositions, Kits, and Methods of Use

The present invention provides pharmaceutical compositions comprising a compound described herein, e.g., a compound of Formula (I), (II), or (III), or pharmaceutically acceptable salts thereof, as described herein, and optionally a pharmaceutically acceptable excipient. It will be understood by one of ordinary skill in the art that the compounds described herein, or salts thereof, may be present as hydrates, solvates, or polymorphs. In certain embodiments, a provided composition comprises two or more compounds described herein. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for treating a disease. In certain embodiments, the effective amount is an amount effective for treating a growth factor-mediated disease. In certain embodiments, the effective amount is an amount effective for treating a VEGF-mediated disease. In certain embodiments, the effective amount is a prophylactically effective amount. In certain embodiments, the effective amount is an amount effective for treating a growth factor-mediated disease. In certain embodiments, the effective amount is an amount effective to prevent a VEGF-mediated disease. In certain embodiments, the effective amount is an amount effective to treat an abnormal angiogenesis-associated disease such as atherosclerosis, hypertension, tumor growth, inflammation, rheumatoid arthritis, wet-form macular degeneration, choroidal neovascularization, retinal neovascularization, and diabetic retinopathy. In certain embodiments, the effective amount is an amount effective to treat cancer. In certain embodiments, the effective amount is an amount effective to treat macular degeneration.

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, about 10 mg to about 100 mg, or about 100 mg to about 1000 mg of a compound per unit dosage form.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kit further includes instructions for use.

Also provided by the present invention are particles that may penetrate mucus, pharmaceutical compositions thereof, kits, and methods of using and preparing the particles, and pharmaceutical compositions thereof. The pharmaceutical compositions, kits, and methods may involve modifying the surface coatings of particles, such as particles of pharmaceutical agents that have a low aqueous solubility. Such pharmaceutical compositions, kits, and methods can be used to achieve efficient transport of particles comprising the inventive compounds through mucus barriers in a subject.

In certain embodiments, the compounds, particles, pharmaceutical compositions, kits, and methods of the invention are useful for applications in the eye, such as treating and/or preventing an ocular disease (e.g., macular degeneration, dry eye syndrome, uveitis, allergic conjunctivitis, glaucoma, and rosacea).

The particles (e.g., nanoparticles and microparticles) of the invention comprise a compound of the invention. The particles of the invention also include a surface-altering agent that modifies the surface of the particles to reduce the adhesion of the particles to mucus and/or to facilitate penetration of the particles through mucus.

The present invention also provides pharmaceutical compositions comprising the inventive particles. In certain embodiments, the pharmaceutical compositions of the invention can be topically administered to the eye of a subject. Topical pharmaceutical compositions are advantageous over pharmaceutical compositions that are administered by injection or orally.

Particles

The present invention also provides pharmaceutical compositions comprising a plurality of particles of the invention, which may be mucus-penetrating and may include a pharmaceutical agent (e.g., a compound of the invention). The inventive pharmaceutical compositions may be useful to deliver the pharmaceutical agent to the eye of a subject and to treat and/or prevent an ocular disease of the subject.

Without wishing to be bound by theory, it is believed that conventional particles (CPs, e.g., non-MPPs) are trapped in the mucus layer (e.g., eye mucin) and are readily cleared from the subject. Thus, the conventional particles may be cleared before the drugs contained in the particles can be transported to target tissue or site (e.g., by diffusion or other mechanisms). In contrast, the particles of compounds the invention formulated as mucus-penetrating particles or MPPs may avoid adhesion to secreted mucins, thereby prolonging particle retention and sustaining drug release.

In some embodiments, the particles of the invention have a core-shell type configuration. The core may comprise the solid pharmaceutical agent including but not limited to pharmaceuticals agents having a relatively low aqueous solubility, or may compromise a pharmaceutical agent and a polymeric carrier, a lipid, and/or a protein. The core may also comprise a gel or a liquid. The core may be coated with a coating or shell comprising a surface-altering agent that facilitates mobility of the particle in mucus. As described in more detail below, the surface-altering agent may comprise a polymer (e.g., a synthetic or a natural polymer) having pendant hydroxyl groups on the backbone of the polymer. The molecular weight and/or degree of hydrolysis of the polymer may be chosen to impart certain transport characteristics to the particles, such as increased transport through mucus. In certain embodiments, the surface-altering agent may comprise a triblock copolymer comprising a (hydrophilic block)-(hydrophobic block)-(hydrophilic block) configuration. The molecular weights of each one of the blocks may be chosen to impart certain transport characteristics to the particles, such as increased transport through mucus. In some embodiments, at least one particle of the invention includes a core and a coating surrounding the core. A particle including a core and a coating on the core is referred to as a "coated particle." In certain embodiments, at least one particle of the invention includes a core but not a coating on the core. A particle including a core but not a coating on the core is referred to as an "uncoated particle."

In some embodiments, a substantial portion of the core is formed of one or more solid pharmaceutical agents (e.g., a compound of the invention) that can lead to certain beneficial and/or therapeutic effects. The core may be, for example, a nanocrystal (i.e., a nanocrystalline particle) of a compound of Formula (I), (II), or (III). In certain embodiments, the core includes a polymeric carrier with a compound of Formula (I), (II), or (III), and optionally with one or more other pharmaceutical agents encapsulated or otherwise associated with the core. In certain embodiments, the core includes a lipid, protein, gel, liquid, and/or another suitable material to be delivered to a subject. The core includes a surface to which one or more surface-altering agents can be attached. In some embodiments, the core is surrounded by coating, which includes an inner surface and an outer surface. The coating may be formed, at least in part, of one or more surface-altering agents, such as a polymer (e.g., a block copolymer and/or a polymer having pendant hydroxyl groups), which may associate with the surface of the core. The surface-altering agent may be associated with the core particle by, for example, being covalently attached to the core particle, non-covalently attached to the core particle, adsorbed to the core, or attached to the core through ionic interactions, hydrophobic and/or hydrophilic interactions, electrostatic interactions, van der Waals interactions, or combinations thereof. In some embodiments, the surface-altering agents, or portions thereof, are chosen to facilitate transport of the particle through or into a mucosal barrier (e.g., mucus or a mucosal membrane). In certain embodiments described herein, one or more surface-altering agents are oriented in a particular configuration in the coating. In some embodiments, in which a surface-altering agent is a triblock copolymer, such as a triblock copolymer having a (hydrophilic block)-(hydrophobic block)-(hydrophilic block) configuration, a hydrophobic block may be oriented towards the surface of the core, and hydrophilic blocks may be oriented away from the core surface (e.g., towards the exterior of the particle). The hydrophilic blocks may have characteristics that facilitate transport of the particle through a mucosal barrier, as described in more detail below.

It should be understood that components and configurations other than those described herein may be suitable for certain particles and pharmaceutical compositions, and that not all of the components described are necessarily present in some embodiments.

In some embodiments, particles of the invention comprising a compound of Formula (I), (II), or (III), when introduced into a subject, may interact with one or more components in the subject such as mucus, cells, tissues, organs, particles, fluids (e.g., blood), microorganisms, and portions or combinations thereof. In some embodiments, the coating of the inventive particle can be designed to include surface-altering agents or other components with properties that allow favorable interactions (e.g., transport, binding, and adsorption) with one or more materials from the subject. For example, the coating may include surface-altering agents or other components having a certain hydrophilicity, hydrophobicity, surface charge, functional group, specificity for binding, and/or density to facilitate or reduce particular interactions in the subject. One example is choosing a hydrophilicity, hydrophobicity, surface charge, functional group, specificity for binding, and/or density of one or more surface-altering agents to reduce the physical and/or chemical interactions between the particle and mucus of the subject, so as to enhance the mobility of the particle through mucus. Other examples are described in more detail below.

In some embodiments, once a particle is successfully transported into and/or across a mucosal barrier (e.g., mucus or a mucosal membrane) in a subject, further interactions between the particle and the subject may take place. In some embodiments, in which the core comprises a pharmaceutical agent or compound of the invention, the conversion, breakdown, release, and/or transport of the pharmaceutical agent from the particle can lead to certain beneficial and/or therapeutic effects in the subject. Therefore, the particles of the invention can be used for the treatment and/or prevention of certain diseases.

Examples for the use of the particles of the invention are provided below in the context of being suitable for administration to a mucosal barrier (e.g., mucus or a mucosal membrane) in a subject. It should be appreciated that while many of the embodiments herein are described in this context, and in the context of providing a benefit for diseases that involve transport of materials across a mucosal barrier, the invention is not limited as such, and the particles, pharmaceutical compositions, and kits of the invention may be used to treat and/or prevent other diseases.

In some embodiments, the pharmaceutical compositions of the invention comprise MPPs that include a compound of the invention and optionally at least one additional pharmaceutical agent, each of which is associated with polymer carriers via encapsulation or other processes. In other embodiments, the pharmaceutical compositions of the invention comprise MPPs without any polymeric carriers or with minimal use of polymeric carriers. Polymer-based MPPs may have one or more inherent limitations in some embodiments. In particular, in light of drug delivery applications, these limitations may include one or more of the following. A) Low drug encapsulation efficiency and low drug loading: encapsulation of drugs into polymeric particles is often inefficient, as generally less than 10% of the total amount of drug used gets encapsulated into particles during manufacturing; additionally, drug loadings above 50% are rarely achieved. B) Convenience of usage: pharmaceutical compositions based on drug-loaded polymeric particles, in general, typically need to be stored as dry powder to avoid premature drug release and thus require either point-of-use re-constitution or a sophisticated dosing device. C) Biocompatibility: accumulation of slowly degrading polymer carriers following repeated dosing and their toxicity over the long term present a major concern for polymeric drug carriers. D) Chemical and physical stability: polymer degradation may compromise stability of encapsulated drugs. In many encapsulation processes, the drug undergoes a transition from a solution phase to a solid phase, which is not well-controlled in terms of physical form of the emerging solid phase (i.e., amorphous vs. crystalline vs. crystalline polymorphs); this is a concern for multiple aspects of pharmaceutical composition performance, including physical and chemical stability and release kinetics. E) Manufacturing complexity: manufacturing, especially scalability, of drug-loaded polymeric MPPs is a fairly complex process that may involve multiple steps and a considerable amount of toxic organic solvents. Therefore, by avoiding or minimizing the need to encapsulate pharmaceutical agents into polymeric carriers, certain limitations of polymeric MPPs with respect to drug loading, convenience of usage, biocompatibility, stability, and/or complexity of manufacturing, may be addressed.

It should be appreciated, however, that in other embodiments, pharmaceutical agents may be associated with polymer carriers via encapsulation or other processes. Thus, the description provided herein is not limited in this respect. For instance, despite the above-mentioned drawbacks of certain mucus-penetrating particles including a polymeric carrier, in certain embodiments such particles may be preferred. For example, it may be preferable to use polymer carriers for controlled release purposes and/or for encapsulating certain pharmaceutical agents that are difficult to formulate into particles. As such, in some embodiments described herein, particles that include a polymer carrier are described.

In some embodiments, the pharmaceutical compositions of the invention involve the use of poly(vinyl alcohols) (PVAs) to aid particle transport in mucus. The pharmaceutical compositions may involve making mucus-penetrating particles by, for example, an emulsification process in the presence of specific PVAs. In certain embodiments, the pharmaceutical compositions and methods involve making mucus-penetrating particles from pre-fabricated particles by non-covalent coating with specific PVAs. In some embodiments, the pharmaceutical compositions and methods involve making MPPs in the presence of specific PVAs without any polymeric carriers or with minimal use of polymeric carriers. It should be appreciated, however, that in other embodiments, polymeric carriers can be used.

PVA is a water-soluble non-ionic synthetic polymer. Due to its surface active properties, PVA is widely used in the food and drug industries as a stabilizing agent for emulsions and, in particular, to enable encapsulation of a wide variety of compounds by emulsification techniques. PVA has the "generally recognized as safe" (GRAS) status with the Food and Drug Administration (FDA), and has been used in auricular, intramuscular, intraocular, intravitreal, iontophoretic, ophthalmic, oral, topical, and transdermal drug products and/or drug delivery systems.

Mucus-penetrating particles can be prepared by tailoring the degree of hydrolysis and/or molecular weight of the PVA, which was previously unknown. This discovery significantly broadens the arsenal of techniques and ingredients applicable for manufacturing MPPs.

In other embodiments, the pharmaceutical compositions of the invention and the methods of making the particles and pharmaceutical compositions of the invention involve PVAs in conjunction with other polymers or do not involve PVAs at all. For example, PEG and/or PLURONICS® (poloxamers) may be included in the pharmaceutical compositions of the invention and methods of making the particles and pharmaceutical compositions of the invention, in addition to or in replace of PVAs. Other polymers, such as those described herein, may also be used.

Core of the Particles

Particles of compounds of the invention formulated to penetrate mucus include a core. The core of the inventive particles may be formed of any suitable material, such as an organic material, inorganic material, polymer, lipid, protein, or combinations thereof. In some embodiments, the core is a solid. The solid may be, for example, a crystalline, semi-crystalline, or amorphous solid, such as a crystalline, semi-crystalline, or amorphous solid of a compound of Formula (I), (II), or (III) the invention, or a salt thereof. In certain embodiments, the core is a gel or liquid (e.g., an oil-in-water or water-in-oil emulsion). In certain embodiments, the core is a nanocrystal of a compound of the invention.

The compound of the invention may be present in the core in any suitable amount, e.g., at least about 80 wt % and less than about 100 wt % of the core. Other ranges are also possible.

In certain embodiments, the core of the particles of the invention is hydrophobic. In certain embodiments, the core is substantially hydrophobic. In certain embodiments, the core is hydrophilic. In certain embodiments, the core is substantially hydrophilic.

In some embodiments, the core includes one or more organic materials, such as a synthetic polymer and/or natural polymer. Examples of synthetic polymers include non-degradable polymers (e.g., polymethacrylate) and degradable polymers (e.g., polylactic acid and polyglycolic acid), and copolymers thereof. Examples of natural polymers include hyaluronic acid, chitosan, and collagen. Other examples of polymers that may be suitable for portions of the core include those suitable for forming coatings on particles, as described herein. In some cases, the one or more polymers present in the core may be used to encapsulate or adsorb one or more pharmaceutical agents.

When a polymer is present in the core, the polymer may be present in the core in any suitable amount, e.g., less than about 100 wt %, less than about 80 wt %, less than about 60 wt %, less than about 50 wt %, less than about 40 wt %, less than about 30 wt %, less than about 20 wt %, less than about 10 wt %, less than about 5 wt %, or less than about 1 wt %. In some cases, the polymer may be present in an amount of at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt % in the core. Combinations of the above-referenced ranges are also possible (e.g., present in an amount of at least about 1 wt % and less than about 20 wt %). Other ranges are also possible. In some embodiments, the core is substantially free of a polymeric component.

The core may have any suitable shape and/or size. For instance, the core may be substantially spherical, non-spherical, oval, rod-shaped, pyramidal, cube-like, disk-shaped, wire-like, or irregularly shaped. The core may have a largest or smallest cross-sectional dimension of, for example, less than about 10 µm, less than about 3 µm, less than about 1 µm, less than about 500 nm, less than 400 nm, less than 300 nm, less than about 200 nm, less than about 100 nm, less than about 30 nm, or less than about 10 nm. In some cases, the core may have a largest or smallest cross-sectional dimension of, for example, at least about 10 nm, at least about 30 nm, at least about 100 nm, at least about 200 nm, at least about 300 nm, at least about 400 nm, at least about 500 nm, at least about 1 µm, or at least about 3 µm. Combinations of the above-referenced ranges are also possible (e.g., a largest or smallest cross-sectional dimension of at least about 30 nm and less than about 500 nm). Other ranges are also possible. In some embodiments, the sizes of the cores formed by a process described herein have a Gaussian-type distribution. Unless indicated otherwise, the measurements of the particle sizes or core sizes refer to the smallest cross-sectional dimension.

Techniques to determine sizes (e.g., smallest or largest cross-sectional dimensions) of particles are known in the art. Examples of suitable techniques include dynamic light scattering (DLS), transmission electron microscopy, scanning electron microscopy, electroresistance counting and laser diffraction. Although many methods for determining sizes of particles are known, the sizes described herein (e.g., average particle sizes and thicknesses) refer to ones measured by DLS.

Coating of the Particles

A particle of the invention may include a coating. An inventive particle comprising a compound of Formula (I), (II), or (III) including a coating may be referred to as a coated particle of the invention. An inventive particle not including a coating may be referred to as an uncoated particle of the invention. In some embodiments, the coating is formed of one or more surface-altering agents or other molecules disposed on the surface of the core. The particular chemical makeup and/or components of the coating and surface-altering agent(s) can be chosen so as to impart certain functionality to the particles, such as enhanced transport through mucosal barriers.

It should be understood that a coating which surrounds a core need not completely surround the core, although such embodiments may be possible. For example, the coating may surround at least about 10%, at least about 30%, at least about 50%, at least about 70%, at least about 90%, or at least about 99% of the surface area of a core. In some cases, the coating substantially surrounds a core. In other cases, the coating completely surrounds a core. In other embodiments, a coating surrounds less than about 100%, less than about 90%, less than about 70%, or less than about 50% of the surface area of a core. Combinations of the above-referenced ranges are also possible (e.g., surrounding at least 70% and less than 100% of the surface area of a core).

The material of the coating may be distributed evenly across a surface of the core in some cases, and unevenly in other cases. For example, the coating may include portions (e.g., holes) that do not include any material. If desired, the coating may be designed to allow penetration and/or transport of certain molecules and components into or out of the coating, but may prevent penetration and/or transport of other molecules and components into or out of the coating. The ability of certain molecules to penetrate and/or be transported into and/or across a coating may depend on, for example, the packing density of the surface-altering agents forming the coating and the chemical and physical properties of the components forming the coating. As described herein, the coating may include one layer of material (i.e., a monolayer) or multilayers of materials. A single type or multiple types of surface-altering agent may be present.

The coating of particles of the invention can have any suitable thickness. For example, the coating may have an average thickness of at least about 1 nm, at least about 3 nm, at least about 10 nm, at least about 30 nm, at least about 100 nm, at least about 300 nm, at least about 1 μm, or at least about 3 μm. In some cases, the average thickness of the coating is less than about 3 μm, less than about 1 μm, less than about 300 nm, less than about 100 nm, less than about 30 nm, less than about 10 nm, or less than about 3 nm. Combinations of the above-referenced ranges are also possible (e.g., an average thickness of at least about 1 nm and less than about 100 nm). Other ranges are also possible. For particles having multiple coatings, each coating may have one of the thicknesses described herein.

The pharmaceutical compositions of the invention may allow for the coating of the particles of the invention with hydrophilic surface-altering moieties without requiring covalent association of the surface-altering moieties to the surface of the core. In some embodiments, the core having a hydrophobic surface is coated with a polymer described herein, thereby causing a plurality of surface-altering moieties to be on the surface of the core without substantially altering the characteristics of the core itself. For example, the surface altering agent may be present on (e.g., adsorbed to) the outer surface of the core. In other embodiments, a surface-altering agent is covalently linked to the core.

In certain embodiments in which the surface-altering agent is adsorbed onto a surface of the core, the surface-altering agent may be in equilibrium with other molecules of the surface-altering agent in solution, optionally with other components (e.g., in a pharmaceutical composition). In some cases, the adsorbed surface-altering agent may be present on the surface of the core at a density described herein. The density may be an average density as the surface altering agent is in equilibrium with other components in solution.

The coating and/or surface-altering agent of the particles of the invention may comprise any suitable material, such as a hydrophobic material, a hydrophilic material, and/or an amphiphilic material. In some embodiments, the coating includes a polymer. In certain embodiments, the polymer is a synthetic polymer (i.e., a polymer not produced in nature). In other embodiments, the polymer is a natural polymer (e.g., a protein, polysaccharide, or rubber). In certain embodiments, the polymer is a surface active polymer. In certain embodiments, the polymer is a non-ionic polymer. In certain embodiments, the polymer is a linear synthetic non-ionic polymer. In certain embodiments, the polymer is a non-ionic block copolymer. The polymer may be a copolymer. In certain embodiments, one repeat unit of the copolymer is relatively hydrophobic and another repeat unit of the copolymer is relatively hydrophilic. The copolymer may be, for example, a diblock, triblock, alternating, or random copolymer. The polymer may be charged or uncharged.

In some embodiments, the coating of the particles of the invention comprises a synthetic polymer having pendant hydroxyl groups on the backbone of the polymer. Examples of the synthetic polymer are as described herein. Without wishing to be bound by theory, a particle including a coating comprising a synthetic polymer having pendant hydroxyl groups on the backbone of the polymer may have reduced mucoadhesion as compared to a control particle due to, at least in part, the display of a plurality of hydroxyl groups on the particle surface. One possible mechanism for the reduced mucoadhesion is that the hydroxyl groups alter the microenvironment of the particle, for example, by ordering water and other molecules in the particle/mucus environment. An additional or alternative possible mechanism is that the hydroxyl groups shield the adhesive domains of the mucin fibers, thereby reducing particle adhesion and speeding up particle transport.

Moreover, the ability of a particle coated with a synthetic polymer having pendant hydroxyl groups on the backbone of the polymer to be mucus penetrating may also depend, at least in part, on the degree of hydrolysis of the polymer. In some embodiments, the hydrophobic portions of the polymer (e.g., portions of the polymer that are not hydrolyzed) allow the polymer to be adhered to the surface of the core (e.g., in the case that the surface of the core is hydrophobic), thus allowing for a strong association between the core and polymer.

A synthetic polymer having pendant hydroxyl groups on the backbone of the polymer may have any suitable degree of hydrolysis (and, therefore, varying amounts of hydroxyl groups). The appropriate level of hydrolysis may depend on additional factors, such as the molecular weight of the polymer, the pharmaceutical composition of the core, and the hydrophobicity of the core. In some embodiments, the synthetic polymer is at least about 30% hydrolyzed, at least about 40% hydrolyzed, at least about 50% hydrolyzed, at least about 60% hydrolyzed, at least about 70% hydrolyzed, at least about 80% hydrolyzed, at least about 90% hydrolyzed, or at least about 95% hydrolyzed. In some embodiments, the synthetic polymer is less than about 100% hydrolyzed, less than about 95% hydrolyzed, less than about 90% hydrolyzed, less than about 80% hydrolyzed, less than about 70% hydrolyzed, or less than about 60% hydrolyzed. Combinations of the above-mentioned ranges are also possible (e.g., a synthetic polymer that is at least about 80% and less than about 95% hydrolyzed). Other ranges are also possible.

The molecular weight of the synthetic polymer described herein (e.g., one having pendant hydroxyl groups on the backbone of the polymer) may be selected so as to reduce the mucoadhesion of a core and to ensure sufficient association of the polymer with the core. In certain embodiments, the molecular weight of the synthetic polymer is at least about 1 kDa, at least about 2 kDa, at least about 5 kDa, at least about 8 kDa, at least about 9 kDa, at least about 10 kDa, at least about 12 kDa, at least about 15 kDa at least about 20 kDa, at least about 25 kDa, at least about 30 kDa, at least about 40 kDa, at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the molecular weight of the synthetic polymer is less than about 1000 kDa, less than about 500 kDa, less than about 200 kDa, less than about, less than about 150 kDa, less than about 130 kDa, less than about 120 kDa, less than about 100 kDa, less than about 85 kDa, less than about 70 kDa, less than about 65 kDa, less than about 60 kDa, less than about 50 kDa, or less than about 40 kDa, less than about 30 kDa, less than about 20 kDa, less than about 15 kDa, or less than about 10 kDa. Combinations of the above-mentioned ranges are also possible (e.g., a molecular weight of at least about 10 kDa and less than about 30 kDa). The above-mentioned molecular weight ranges can also be combined with the above-mentioned hydrolysis ranges to form suitable polymers.

In some embodiments, the synthetic polymer described herein is or comprises PVA. In some embodiments, the synthetic polymer described herein is or comprises partially hydrolyzed PVA. Partially hydrolyzed PVA includes two types of repeating units: vinyl alcohol units and residual vinyl acetate units. The vinyl alcohol units are relatively hydrophilic, and the vinyl acetate units are relatively hydrophobic. In some instances, the sequence distribution of vinyl alcohol units and vinyl acetate units is blocky. For example, a series of vinyl alcohol units may be followed by a series of vinyl acetate units, and followed by more vinyl alcohol units to form a polymer having a mixed block-copolymer type arrangement, with units distributed in a blocky manner. In certain embodiments, the repeat units form a copolymer, e.g., a diblock, triblock, alternating, or random copolymer. Polymers other than PVA may also have these configurations of hydrophilic units and hydrophobic units.

In some embodiments, the hydrophilic units of the synthetic polymer described herein are substantially present at the outer surface of the particles of the invention. For example, the hydrophilic units may form a majority of the outer surface of the coating and may help stabilize the particles in an aqueous solution containing the particles. The hydrophobic units may be substantially present in the interior of the coating and/or at the surface of the core, e.g., to facilitate attachment of the coating to the core.

The molar fraction of the relatively hydrophilic units and the relatively hydrophobic units of the synthetic polymer described herein may be selected so as to reduce the mucoadhesion of a core and to ensure sufficient association of the polymer with the core. As described herein, the molar fraction of the hydrophobic units of the polymer may be chosen such that adequate association of the polymer with the core occurs, thereby increasing the likelihood that the polymer remains adhered to the core. The molar fraction of the relatively hydrophilic units to the relatively hydrophobic units of the synthetic polymer may be, for example, at least 0.5:1, at least 1:1, at least 2:1, at least 3:1, at least 5:1, at least 10:1, at least 20:1, at least 30:1, at least 50:1, or at least 100:1. In some embodiments, the molar fraction of the relatively hydrophilic units to the relatively hydrophobic units of the synthetic polymer may be, for example, less than 100:1, less than 50:1, less than 30:1, less than 20:1, less than 10:1, less than 5:1, less than 3:1, less than 2:1, or less than 1:1. Combinations of the above-referenced ranges are also possible (e.g., a ratio of at least 1:1 and less than 50:1). Other ranges are also possible.

The molecular weight of the PVA polymer may also be tailored to increase the effectiveness of the polymer to render particles mucus penetrating. Examples of PVA polymers having various molecular weights and degree of hydrolysis are shown in Table 1.

TABLE 1

Molecular weight (MW) and degree of hydrolysis of various poly(vinyl alcohols) (PVAs).[a]

| PVA | MW (kDa) | Hydrolysis degree (%) |
|---|---|---|
| 2K75 | 2 | 75-79 |
| 9K80 | 9-10 | 80 |
| 13K87 | 13-23 | 87-89 |
| 13K98 | 13-23 | 98 |
| 31K87 | 31-50 | 87-89 |
| 31K98 | 31-50 | 98-99 |
| 57K86 | 57-60 | 86-89 |
| 85K87 | 85-124 | 87-89 |
| 85K99 | 85-124 | 99+ |
| 95K95 | 95 | 95 |
| 105K80 | 104 | 80 |
| 130K87 | 130 | 87-89 |

[a]The values of the molecular weight and hydrolysis degree of the PVAs were provided by the manufacturers of the PVAs.

In certain embodiments, the synthetic polymer is represented by the formula:

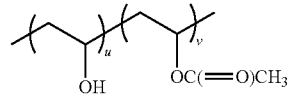

wherein:
u is an integer between 0 and 22730, inclusive; and
v is an integer between 0 and 11630, inclusive.

In some embodiments, the particles of the invention include a coating comprising a block copolymer having a relatively hydrophilic block and a relatively hydrophobic block. In some cases, the hydrophilic blocks may be substantially present at the outer surface of the particle. For example, the hydrophilic blocks may form a majority of the outer surface of the coating and may help stabilize the particle in an aqueous solution containing the particle. The hydrophobic block may be substantially present in the interior of the coating and/or at the surface of the core, e.g., to facilitate attachment of the coating to the core. In some embodiments, the coating comprises a surface-altering agent including a triblock copolymer, wherein the triblock copolymer comprises a (hydrophilic block)-(hydrophobic block)-(hydrophilic block) configuration. Diblock copolymers having a (hydrophilic block)-(hydrophobic block) configuration are also possible. Combinations of block copolymers with other polymers suitable for use as coatings are also possible. Non-linear block configurations are also possible such as in comb, brush, or star copolymers. In some embodiments, the relatively hydrophilic block includes a synthetic polymer having pendant hydroxyl groups on the backbone of the polymer (e.g., PVA).

The molecular weight of the hydrophilic blocks and the hydrophobic blocks of the block copolymers described herein may be selected so as to reduce the mucoadhesion of a core and to ensure sufficient association of the block copolymer with the core, respectively. The molecular weight of the hydrophobic block of the block copolymer may be chosen such that adequate association of the block copolymer with the core occurs, thereby increasing the likelihood that the block copolymer remains adhered to the core.

In certain embodiments, the molecular weight of each block of or combined blocks of the (one or more) relatively hydrophobic blocks of a block copolymer is at least about 0.5 kDa, at least about 1 kDa, at least about 1.8 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the molecular weight of each block of or combined blocks of the (one or more) relatively hydrophobic blocks is less than about 1000 kDa, less than about 500 kDa, less than about 200 kDa, less than about 150 kDa, less than about 140 kDa, less than about 130 kDa, less than about 120 kDa, less than about 110 kDa, less than about 100 kDa, less than about 90 kDa, less than about 80 kDa, less than about 50 kDa, less than about 20 kDa, less than about 15 kDa, less than about 13 kDa, less than about 12 kDa, less than about 10 kDa, less than about 8 kDa, or less than about 6 kDa. Combinations of the above-mentioned ranges are also possible (e.g., at least about 3 kDa and less than about 15 kDa). Other ranges are also possible.

In some embodiments, the combined relatively hydrophilic blocks (e.g., two hydrophilic blocks of a triblock copolymer) of a block copolymer (e.g., a triblock copolymer) constitute at least about 10 wt %, at least about 20 wt %, at least about 30 wt %, at least about 40 wt %, at least about 50 wt %, at least about 60 wt %, or at least about 70 wt % of the block copolymer. In some embodiments, the combined (one or more) relatively hydrophilic blocks of a block copolymer constitute less than about 90 wt %, less than about 80 wt %, less than about 60 wt %, less than about 50 wt %, or less than about 40 wt % of the block copolymer. Combinations of the above-referenced ranges are also possible (e.g., at least about 30 wt % and less than about 70 wt %). Other ranges are also possible.

In some embodiments, the molecular weight of each block of or combined blocks of the (one or more) relatively hydrophilic blocks of the block copolymer may be at least about 0.5 kDa, at least about 1 kDa, at least about 1.8 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In certain embodiments, the molecular weight of each block of or combined blocks of the (one or more) relatively hydrophilic blocks is less than about 1000 kDa, less than about 500 kDa, less than about 200 kDa, less than about 150 kDa, less than about 140 kDa, less than about 130 kDa, less than about 120 kDa, less than about 110 kDa, less than about 100 kDa, less than about 90 kDa, less than about 80 kDa, less than about 50 kDa, less than about 20 kDa, less than about 15 kDa, less than about 13 kDa, less than about 12 kDa, less than about 10 kDa, less than about 8 kDa, less than about 6 kDa, less than about 5 kDa, less than about 3 kDa, less than about 2 kDa, or less than about 1 kDa. Combinations of the above-mentioned ranges are also possible (e.g., at least about 0.5 kDa and less than about 3 kDa). Other ranges are also possible. In embodiments in which two hydrophilic blocks flank a hydrophobic block, the molecular weights of the two hydrophilic blocks may be substantially the same or different.

In certain embodiments, the polymer of the surface-altering agent includes a polyether portion. In certain embodiments, the polymer includes a polyalkylether portion. In certain embodiments, the polymer includes polyethylene glycol (PEG) tails. In certain embodiments, the polymer includes a polypropylene glycol as the central portion. In certain embodiments, the polymer includes polybutylene glycol as the central portion. In certain embodiments, the polymer includes polypentylene glycol as the central portion. In certain embodiments, the polymer includes polyhexylene glycol as the central portion. In certain embodiments, the polymer is a triblock copolymer of one of the polymers described herein. In some embodiments, a diblock or triblock copolymer comprises a synthetic polymer having pendant hydroxyl groups on the backbone of the polymer (e.g., PVA) as one or more of the blocks (with varying degrees of hydrolysis and varying molecular weights as described herein). The synthetic polymer blocks may form the central portion or end portions of the block copolymer.

In certain embodiments, the polymer is a triblock copolymer of a polyalkyl ether (e.g., polyethylene glycol, polypropylene glycol) and another polymer (e.g., a synthetic polymer having pendant hydroxyl groups on the backbone of the polymer (e.g., PVA). In certain embodiments, the polymer is a triblock copolymer of a polyalkyl ether and another polyalkyl ether. In certain embodiments, the polymer is a triblock copolymer of polyethylene glycol and another polyalkyl ether. In certain embodiments, the polymer is a triblock copolymer of polypropylene glycol and another polyalkyl ether. In certain embodiments, the polymer is a triblock copolymer with at least one unit of polyalkyl ether. In certain embodiments, the polymer is a triblock copolymer of two different polyalkyl ethers. In certain embodiments, the polymer is a triblock copolymer including a polyethylene glycol unit. In certain embodiments, the polymer is a triblock copolymer including a polypropylene glycol unit. In certain embodiments, the polymer is a triblock copolymer of a more hydrophobic unit flanked by two more hydrophilic units. In certain embodiments, the hydrophilic units are the same type of polymer. In some embodiments, the hydrophilic units include a synthetic polymer having pendant hydroxyl groups on the backbone of the polymer (e.g., PVA). In certain embodiments, the polymer includes a polypropylene glycol unit flanked by two more hydrophilic units. In certain embodiments, the polymer includes two polyethylene glycol units flanking a more hydrophobic unit. In certain embodiments, the polymer is a triblock copolymer with a polypropylene glycol unit flanked by two polyethylene glycol units. The molecular weights of the two blocks flanking the central block may be substantially the same or different.

In certain embodiments, the polymer is of the formula:

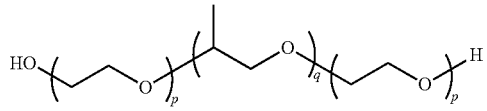

wherein each instance of p is independently an integer between 2 and 1140, inclusive; and q is an integer between 2 and 1730, inclusive. In certain embodiments, each instance of p is independently an integer between 10 and 170, inclusive. In certain embodiments, q is an integer between 5 and 70 inclusive. In certain embodiments, each instance of p is independently at least 2 times of q, 3 times of q, or 4 times of q.

In certain embodiments, the surface-altering agent comprises a (poly(ethylene glycol))-(poly(propylene oxide))-(poly(ethylene glycol)) triblock copolymer (PEG-PPO-PEG triblock copolymer), present in the coating alone or in combination with another polymer such as a synthetic polymer having pendant hydroxyl groups on the backbone of the polymer (e.g., PVA). The molecular weights of the PEG and PPO segments of the PEG-PPO-PEG triblock copolymer may be selected so as to reduce the mucoadhesion of the particles, as described herein. Without wishing to be bound by any theory, the particles of the invention having a coating comprising a PEG-PPO-PEG triblock copolymer may have reduced mucoadhesion as compared to control particles due to, at least in part, the PEG segments on the surface of the particles of the invention. The PPO segment may be adhered to the surface of the core (e.g., in the case of the surface of the core being hydrophobic), thus allowing for a strong association between the core and the triblock copolymer. In some embodiments, the PEG-PPO-PEG triblock copolymer is associated with the core through non-covalent interactions. For purposes of comparison, the control particle may be, for example, a carboxylate-modified polystyrene particle of similar size as the particle of the invention.

In certain embodiments, the surface-altering agent includes a polymer comprising a poloxamer, having the trade name PLURONIC®. PLURONIC® polymers that may be useful in the embodiments described herein include, but are not limited to, F127, F38, F108, F68, F77, F87, F88, F98, L101, L121, L31, L35, L43, L44, L61, L62, L64, L81, L92, N3, P103, P104, P105, P123, P65, P84, and P85. Examples of molecular weights of certain PLURONIC® polymers are shown in Table 2.

TABLE 2

Molecular weight (MW) of PLURONIC ® polymers

| PLURONIC ® | Average MW (Da) | MW of the PPO portion (Da) | PEG wt % | MW of the PEG portion (Da) |
|---|---|---|---|---|
| F127 | 12000 | 3600 | 70 | 8400 |
| L44 | 2000 | 1200 | 40 | 800 |
| L81 | 2667 | 2400 | 10 | 267 |
| L101 | 3333 | 3000 | 10 | 333 |
| P65 | 3600 | 1800 | 50 | 1800 |
| L121 | 4000 | 3600 | 10 | 400 |
| P103 | 4286 | 3000 | 30 | 1286 |

TABLE 2-continued

Molecular weight (MW) of PLURONIC ® polymers

| PLURONIC ® | Average MW (Da) | MW of the PPO portion (Da) | PEG wt % | MW of the PEG portion (Da) |
|---|---|---|---|---|
| F38 | 4500 | 900 | 80 | 3600 |
| P123 | 5143 | 3600 | 30 | 1543 |
| P105 | 6000 | 3000 | 50 | 3000 |
| F87 | 8000 | 2400 | 70 | 5600 |
| F68 | 9000 | 1800 | 80 | 7200 |
| P123 | 5750 | 4030 | 30 | 1730 |

Although other ranges may be possible, in some embodiments, the hydrophobic block of the PEG-PPO-PEG triblock copolymer has one of the molecular weights described above (e.g., at least about 3 kDa and less than about 15 kDa), and the combined hydrophilic blocks have a weight percentage with respect to the polymer in one of the ranges described above (e.g., at least about 15 wt %, at least about 20 wt %, at least about 25 wt %, or at least about 30 wt %, and less than about 80 wt %). Certain PLURONIC® polymers that fall within these criteria include, for example, F127 (poloxamer 407), F108 (poloxamer 338), P105, and P103. In certain embodiments, the particles of the invention including PLURONIC® polymers that fall within these criteria are more mucus penetrating than particles including PLURONIC® polymers that did not fall within these criteria. Materials that do not render the particles mucus penetrating also include certain polymers such as polyvinylpyrrolidones (PVP/KOLLIDON), polyvinyl alcohol-polyethylene glycol graft-copolymer (KOLLICOAT IR), and hydroxypropyl methylcellulose (METHOCEL); oligomers such as TWEEN 20, TWEEN 80, SOLUTOL HS 15, TRITON X100, tyloxapol, and CREMOPHOR RH 40; and small molecules such as SPAN 20, SPAN 80, octyl glucoside, cetytrimethylammonium bromide (CTAB), and sodium dodecyl sulfate (SDS).

Although much of the description herein may involve coatings comprising a (hydrophilic block)-(hydrophobic block)-(hydrophilic block) configuration (e.g., a PEG-PPO-PEG triblock copolymer) or coatings comprising a synthetic polymer having pendant hydroxyl groups, it should be appreciated that the coatings are not limited to these configurations and materials and that other configurations and materials are possible.

Furthermore, although many of the embodiments described herein involve a single coating, in other embodiments, a particle may include more than one coating (e.g., at least two, three, four, five, or more coatings), and each coating need not be formed of or comprise a mucus penetrating material. In some embodiments, an intermediate coating (i.e., a coating between the core surface and an outer coating) may include a polymer that facilitates attachment of an outer coating to the core surface. In some embodiments, an outer coating of a particle includes a polymer comprising a material that facilitates the transport of the particle through mucus.

The coating (e.g., an inner coating, intermediate coating, and/or outer coating) of the particles of the invention may include any suitable polymer. In some embodiments, the polymer of the coating is biocompatible and/or biodegradable. In some embodiments, the polymer of the coating comprises more than one type of polymer (e.g., at least two, three, four, five, or more types of polymers). In some embodiments, the polymer of the coating is a random copolymer or a block copolymer (e.g., a diblock or triblock copolymer) as described herein.

Non-limiting examples of suitable polymers of the coating may include polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate.

The molecular weight of the polymer of the coating may vary. In some embodiments, the molecular weight of the polymer of the coating is at least about 0.5 kDa, at least about 1 kDa, at least about 1.8 kDa, at least about 2 kDa, at least about 3 kDa, at least about 4 kDa, at least about 5 kDa, at least about 6 kDa, at least about 8 kDa, at least about 10 kDa, at least about 12 kDa, at least about 15 kDa, at least about 20 kDa, at least about 30 kDa, at least about 40 kDa, or at least about 50 kDa. In some embodiments, the molecular weight of the polymer of the coating is less than about 50 kDa, less than about 40 kDa, less than about 30 kDa, less than about 20 kDa, less than about 12 kDa, less than about 10 kDa, less than about 8 kDa, less than about 6 kDa, less than about 5 kDa, or less than about 4 kDa. Combinations of the above-referenced ranges are possible (e.g., a molecular weight of at least about 2 kDa and less than about 15 kDa). Other ranges are also possible. The molecular weight of the polymer of the coating may be determined using any known technique such as light-scattering and gel permeation chromatography. Other methods are known in the art.

In certain embodiments, the molecular weight of the hydrophobic block of the triblock copolymer of the (hydrophilic block)-(hydrophobic block)-(hydrophilic block) configuration is at least about 2 kDa, and the two hydrophilic blocks constitute at least about 15 wt % of the triblock copolymer.

In certain embodiments, the polymer of the coating is biocompatible. In certain embodiments, the polymer of the coating is biodegradable. All biocompatible polymers and biodegrade polymers are contemplated to be within the scope of the invention. In certain embodiments, a polymer degrades in vivo within a period that is acceptable for the desired application. For example, in an in vivo therapy, the polymer degrades in a period less than about five years, about one year, about six months, about three months, about one month, about two weeks, about one week, about three days, about one day, about six hours, or about one hour upon exposure to a physiological environment with a pH between about 6 and about 8 having a temperature of between about 25 and about 37° C. In some embodiments, the polymer of the coating degrades in a period of between about one hour and several weeks, depending on the desired application.

Although the particles of the invention, and the coating thereof, may each include polymers, in some embodiments, the particles of the invention comprise a hydrophobic material that is not a polymer or pharmaceutical agent. Non-limiting examples of non-polymeric hydrophobic materials include, for example, metals, waxes, and organic materials (e.g., organic silanes and perfluorinated or fluorinated organic materials).

Particles with Reduced Mucoadhesion

Coated particles of the invention may have reduced mucoadhesiveness. A material in need of increased diffusivity through mucus may be hydrophobic, may include many hydrogen bond donors or acceptors, and/or may be highly charged. In some cases, the material may include a crystalline or amorphous solid material. The material, which may serve as a core, may be coated with a suitable polymer described herein, thereby forming a particle with a plurality of surface-altering moieties on the surface, resulting in reduced mucoadhesion. Particles of the invention as having reduced mucoadhesion may alternatively be characterized as having increased transport through mucus, being mobile in mucus, or mucus-penetrating (i.e., mucus-penetrating particles), meaning that the particles are transported through mucus faster than a negative control particle. The negative control particle may be a particle that is known to be mucoadhesive, e.g., an unmodified particle or core that is not coated with a coating described herein, such as a 200 nm carboxylated polystyrene particle.

Coated particles of the invention may be adapted for delivery (e.g., ocular delivery) to mucus or a mucosal surface of a subject. The particles with surface-altering moieties may be delivered to the mucosal surface of a subject, may pass through the mucosal barrier in the subject, and/or prolonged retention and/or increased uniform distribution of the particles at mucosal surfaces, e.g., due to reduced mucoadhesion.

Furthermore, in some embodiments, the coated particles of the invention having reduced mucoadhesion facilitate better distribution of the particles at the surface of a tissue of a subject and/or have a prolonged presence at the surface of the tissue, compared to particles that are more mucoadhesive. For example, a luminal space such as the gastrointestinal tract is surrounded by a mucus-coated surface. Mucoadhesive particles delivered to such a space are typically removed from the luminal space and from the mucus-coated surface by the subject's natural clearance mechanisms. The particles of the invention with reduced mucoadhesion may remain in the luminal space for relatively longer periods compared to the mucoadhesive particles. This prolonged presence may prevent or reduce clearance of the particles and/or may allow for better distribution of the particles on the surface of the tissue. The prolonged presence may also affect the particle transport through the luminal space, e.g., the particles may distribute into the mucus layer and may reach the underlying epithelium.

In certain embodiments, the core of the particles of the invention coated with the polymer of the coating may pass through mucus or a mucosal barrier in a subject, exhibit prolonged retention, and/or increase uniform distribution of the particles at mucosal surfaces, e.g., such substances are cleared more slowly (e.g., at least about 2 times, about 5 times, about 10 times, or even at least about 20 times more slowly) from a subject's body as compared to a negative control particle of the invention.

The mobility of the particles of the invention in mucus may be characterized in, e.g., the relative velocity and/or diffusivity of the particles. In certain embodiments, the particles of the invention have certain relative velocity, $\langle V_{mean}\rangle_{rel}$, which is defined as follows:

$$\langle V_{mean}\rangle_{rel} = \frac{\langle V_{mean}\rangle_{Sample} - \langle V_{mean}\rangle_{Negative\ control}}{\langle V_{mean}\rangle_{Positive\ control} - \langle V_{mean}\rangle_{Negative\ control}} \quad \text{(Equation 1)}$$

wherein:

$\langle V_{mean}\rangle$ is the ensemble average trajectory-mean velocity;

$V_{mean}$ is the velocity of an individual particle averaged over its trajectory;

the sample is the particle of interest;

the negative control is a 200 nm carboxylated polystyrene particle; and the positive control is a 200 nm polystyrene particle densely PEGylated with 2-5 kDa PEG.

The relative velocity can be measured by a multiple particle tracking technique. For instance, a fluorescent microscope equipped with a CCD camera can be used to capture 15 s movies at a temporal resolution of 66.7 ms (15 frames/s) under 100× magnification from several areas within each sample for each type of particles: sample, negative control, and positive control. The sample, negative control, and positive control may be fluorescent particles to observe tracking. Alternatively non-fluorescent particles may be coated with a fluorescent molecule, a fluorescently tagged surface agent, or a fluorescently tagged polymer. An advanced image processing software (e.g., IMAGE PRO or METAMORPH) can be used to measure individual trajectories of multiple particles over a time-scale of at least 3.335 s (50 frames).

In some embodiments, the particles of the invention have a relative velocity of greater than or equal to about 0.3, greater than or equal to about 0.5, greater than or equal to about 0.7, greater than or equal to about 1.0, greater than or equal to about 1.5, or greater than or equal to about 2.0 in mucus. In some embodiments, particles of the invention have a relative velocity of less than about 10.0, less than about 6.0, less than about 2.0, less than about 1.5, less than about 1.0, or less than about 0.7 in mucus. Combinations of the above-noted ranges are possible (e.g., a relative velocity of greater than or equal to about 0.5 and less than about 6.0). Other ranges are also possible.

In certain embodiments, the particles of the invention diffuse through mucus or a mucosal barrier at a greater rate or diffusivity than negative control particles or corresponding particles (e.g., particles that are unmodified and/or not coated with a coating described herein). In some embodiments, the particles of the invention pass through mucus or a mucosal barrier at a rate of diffusivity that is at least about 10 times, about 30 times, about 100 times, about 300 times, about 1000 times, about 3000 times, about 10000 times higher than a control particle or a corresponding particle. In some embodiments, the particles of the invention pass through mucus or a mucosal barrier at a rate of diffusivity that is less than about 10000 times higher, less than about 3000 times higher, less than about 1000 times higher, less than about 300 times higher, less than about 100 times higher, less than about 30 times higher, or less than about 10 times higher than negative control particles or corresponding particles. Combinations of the above-referenced ranges are also possible (e.g., at least about 10 times and less than about 1000 times higher than negative control particles or corresponding particles). Other ranges are also possible.

For the purposes of the comparisons described herein, the corresponding particles may be approximately the same size, shape, and/or density as the particles of the invention but lack the coating that makes the particles of the invention mobile in mucus. In some embodiments, the measurement of the geometric mean square displacement and rate of diffusivity of the particles (e.g., the corresponding particles and particles of the invention) is based on a time scale of about 1 second, about 3 seconds, or about 10 seconds. Methods for determining the geometric mean square displacement and rate of diffusivity are known in the art. The particles of the invention may pass through mucus or a mucosal barrier with a geometric mean squared displacement that is at least about 10 times, about 30 times, about 100 times, about 300 times, about 1000 times, about 3000 times, about 10000 times higher than corresponding particles or negative control particles. In some embodiments, the particles of the invention pass through mucus or a mucosal barrier with a geometric mean squared displacement that is less than about 10000 times higher, less than about 3000 times higher, less than about 1000 times higher, less than about 300 times higher, less than about 100 times higher, less than about 30 times higher, or less than about 10 times higher than negative control particles or corresponding particles. Combinations of the above-referenced ranges are also possible (e.g., at least about 10 times and less than about 1000 times higher than negative control particles or corresponding particles). Other ranges are also possible.

In some embodiments, coated particles of the invention diffuse through a mucosal barrier at a rate approaching the rate or diffusivity at which the particles can diffuse through water. In some embodiments, the particles of the invention pass through a mucosal barrier at a rate or diffusivity that is less than about 1/100, less than about 1/300, less than about 1/1000, less than about 1/3000, less than about 1/10,000 of the diffusivity that the particles diffuse through water under similar conditions. In some embodiments, coated particles of the invention pass through a mucosal barrier at a rate or diffusivity that is greater than or equal to about 1/10,000, greater than or equal to about 1/3000, greater than or equal to about 1/1000, greater than or equal to about 1/300, or greater than or equal to about 1/100 of the diffusivity that the particles diffuse through water under similar conditions. Combinations of the above-referenced ranges are also possible (e.g., greater than or equal to about 1/3000 and less than 1/300 the diffusivity that the particles diffuse through water under similar conditions). Other ranges are also possible. The measurement of diffusivity may be based on a time scale of about 1 second, or about 0.5 second, or about 2 seconds, or about 5 seconds, or about 10 seconds.

In some embodiments, the coated particles of the invention diffuse through human cervicovaginal mucus at a diffusivity that is less than about 1/500 of the diffusivity that the particles diffuse through water. In some embodiments, the measurement of diffusivity is based on a time scale of about 1 second, or about 0.5 second, or about 2 seconds, or about 5 seconds, or about 10 seconds.

In certain embodiments, the coated particles of the invention travel through mucus, such as human cervicovaginal mucus, at certain absolute diffusivities. For example, the coated particles of the invention may travel at diffusivities of at least about $1 \times 10^{-4}$ µm/s, about $3 \times 10^{-4}$ µm/s, about $1 \times 10^{-3}$ µm/s, about $3 \times 10^{-3}$ µm/s, about $1 \times 10^{-2}$ µm/s, about $3 \times 10^{-2}$ µm/s, about $1 \times 10^{-1}$ µm/s, about $3 \times 10^{-1}$ µm/s, about 1 µm/s, or about 3 µm/s. In some embodiments, the coated particles may travel at diffusivities of less than about 3 µm/s, less than about 1 µm/s, less than about $3 \times 10^{-1}$ µm/s, less than about $1 \times 10^{-1}$ µm/s, less than about $3 \times 10^{-2}$ µm/s, less than about $1 \times 10^{-2}$ µm/s, less than about $3 \times 10^{-3}$ µm/s, less than about $1 \times 10^{-3}$ µm/s, less than about $3 \times 10^{-4}$ µm/s, or less than about $1 \times 10^{-4}$ µm/s. Combinations of the above-referenced ranges are also possible (e.g., greater than or equal to about $3 \times 10^{-4}$ µm/s and less than about $1 \times 10^{-1}$ µm/s). Other ranges are also possible. In some cases, the measurement of diffusivity is based on a time scale of about 1 second, or about 0.5 second, or about 2 seconds, or about 5 seconds, or about 10 seconds.

It should be appreciated that while the mobility (e.g., relative velocity and diffusivity) of the coated particles of the invention may be measured in human cervicovaginal mucus, the mobility may be measured in other types of mucus as well.

In certain embodiments, the coated particles of the invention comprise surface-altering moieties at a given density. The surface-altering moieties may be the portions of a surface-altering agent that are, for example, exposed to the solvent containing the particles. In one example, the hydrolyzed units/blocks of PVA may be surface-altering moieties of the surface-altering agent PVA. In another example, the PEG segments may be surface-altering moieties of the surface-altering agent PEG-PPO-PEG. In some embodiments, the surface-altering moieties and/or surface-altering agents are present at a density of at least about 0.001 units or molecules per $nm^2$, at least about 0.003, at least about 0.01, at least about 0.03, at least about 0.1, at least about 0.3, at least about 1, at least about 3, at least about 10, at least about 30, at least about 100 units or molecules per $nm^2$, or more units or molecules per $nm^2$. In some cases, the surface-altering moieties and/or surface-altering agents are present at a density of less than about 100 units or molecules per $nm^2$, less than about 30, less than about 10, less than about 3, less than about 1, less than about 0.3, less than about 0.1, less than about 0.03, or less than about 0.01 units or molecules per $nm^2$. Combinations of the above-referenced ranges are possible (e.g., a density of at least about 0.01 and less than about 1 units or molecules per $nm^2$). Other ranges are also possible. In some embodiments, the density values described herein are an average density as the surface altering agent is in equilibrium with other components in solution.

Those skilled in the art would be aware of methods to estimate the average density of surface-altering moieties (see, for example, Budijono et al., *Colloids and Surfaces A: Physicochem. Eng. Aspects* 2010, 360, 105-110; Joshi et al., *Anal. Chim. Acta* 1979, 104, 153-160). For example, as described herein, the average density of surface-altering moieties can be determined using HPLC quantitation and DLS analysis. A suspension of particles for which surface density determination is of interest is first sized using DLS: a small volume is diluted to an appropriate concentration (e.g., about 100 µg/mL), and the z-average diameter is taken as a representative measurement of particle size. The remaining suspension is then divided into two aliquots. Using HPLC, the first aliquot is assayed for the total concentration of core material and for the total concentration of the surface-altering moiety. Again using HPLC, the second aliquot is assayed for the concentration of free or unbound surface-altering moiety. In order to get only the free or unbound surface-altering moiety from the second aliquot, the particles, and therefore any bound surface-altering moiety, are removed by ultracentrifugation. By subtracting the concentration of the unbound surface-altering moiety from the total concentration of surface-altering moiety, the concentration of bound surface-altering moiety can be determined. Since the total concentration of core material was also determined from the first aliquot, the mass ratio between the core material and the surface-altering moiety can be determined. Using the molecular weight of the surface-altering moiety the number of surface-altering moiety to mass of core material can be calculated. To turn this number into a surface density measurement, the surface area per mass of core material needs to be calculated. The volume of the particle is approximated as that of a sphere with the diameter obtained from DLS allowing for the calculation of the surface area per mass of core material. In this way the number of surface-altering moieties per surface area can be determined.

In certain embodiments, the coated particles of the invention comprise surface-altering moieties and/or agents that affect the zeta-potential of the particle. The zeta potential of the particle may be, for example, at least about −100 mV, at least about −30 mV, at least about −10 mV, at least about −3 mV, at least about 3 mV, at least about 10 mV, at least about 30 mV, or at least about 100 mV. The zeta potential of the particle may also be, for example, less than about 100 mV, less than about 30 mV, less than about 10 mV, less than about 3 mV, less than about −3 mV, less than about −10 mV, less than about −30 mV, or less than about −100 mV. Combinations of the above-referenced ranges are possible (e.g., a zeta-potential of at least about −30 mV and less than about 30 mV). Other ranges are also possible.

The particles of the invention may have any suitable shape and/or size. In some embodiments, the particle has a shape substantially similar to the shape of the core. In some embodiments, the particle is a nanoparticle. In some embodiments, the particle is a microparticle. A plurality of particles, in some embodiments, may also be characterized by an average size (e.g., an average largest cross-sectional dimension or average smallest cross-sectional dimension for a plurality of particles). A plurality of particles may have an average size of, for example, less than about 10 µm, less than about 3 µm, less than about 1 µm, less than about 500 nm, less than 400 nm, less than about 300 nm, less than about 200 nm, less than about 100 nm, less than about 50 nm, less than about 30 nm, or less than about 10 nm. In some cases, a plurality of particles may have an average size of, for example, at least about 10 nm, at least about 30 nm, at least about 50 nm, at least about 100 nm, at least about 200 nm, at least about 300 nm, at least about 400 nm, at least about 500 nm, at least about 1 µm, at least or at least about 3 µm. Combinations of the above-referenced ranges are also possible (e.g., an average size of at least about 30 nm and less than about 500 nm). Other ranges are also possible. In some embodiments, the sizes of the cores of the particles of the invention have a Gaussian-type distribution. In some embodiments, the sizes of the particles of the invention have a Gaussian-type distribution.

Pharmaceutical Agents

A particle or pharmaceutical composition of the invention may comprise at least one pharmaceutical agent of Formula (I), (II), or (III). In certain embodiments, the pharmaceutical agent described herein is a pharmaceutically acceptable salt, solvate, hydrate, polymorph, tautomer, stereoisomer, isotopically labeled derivative, or prodrug of another pharmaceutical agent. In certain embodiments, the pharmaceutical agent is a co-crystal with another substance (e.g., a solvent, protein, or another pharmaceutical agent). The pharmaceutical agent may be present in the core and/or one or more coatings of the particle (e.g., dispersed throughout the core and/or coating). In some embodiments, the pharmaceutical agent may be disposed on the surface of the particle (e.g., on the outer or inner surface of the one or more coatings or on the surface of the core). The pharmaceutical agent may be contained within the particle and/or disposed in a portion of the particle using commonly known techniques (e.g., coating, adsorption, covalent linkage, and encapsulation). In some embodiments, the pharmaceutical agent is present during the formation of the core. In other embodiments, the pharmaceutical agent is not present during the formation of the core. In certain embodiments, the pharmaceutical agent is present during the coating of the core. In certain embodiments, the pharmaceutical agent is the core of the particle.

In some embodiments, the pharmaceutical agent contained in a particle or pharmaceutical composition of the invention has a therapeutic and/or prophylactic effect in a mucosal tissue to be targeted. Non-limiting examples of mucosal tissues include ophthalmic, respiratory (e.g., including nasal, pharyngeal, tracheal, and bronchial membranes), oral (e.g., including the buccal and esophagal membranes and tonsil surface), gastrointestinal (e.g., including stomach, small intestine, large intestine, colon, rectum), nasal, and genital (e.g., including vaginal, cervical and urethral membranes) tissues.

Any suitable number of pharmaceutical agents may be present in a particle or pharmaceutical composition of the invention. For example, at least 1, at least 2, at least 3, at least 4, at least 5, or more pharmaceutical agents may be present in the particle or pharmaceutical composition of the invention. In certain embodiments, less than 10 pharmaceutical agents are present in the particle or pharmaceutical composition of the invention.

In certain embodiments, the pharmaceutical agent in the particles or pharmaceutical compositions of the invention is a compound of the invention. The pharmaceutical agent described herein (e.g., a compound of the invention) may be encapsulated in a polymer, a lipid, a protein, or a combination thereof.

Pharmaceutical Compositions

In another aspect, the present invention provides pharmaceutical compositions comprising the plurality of particles of a compound of Formula (I), a compound of Formula (II), or a compound of Formula (III) of the invention.

In certain embodiments, the pharmaceutical compositions are useful for the delivery of a pharmaceutical agent described herein (e.g., a compound of the invention) through or to mucus or a mucosal surface in a subject. The pharmaceutical compositions may be delivered to the mucosal surface in the subject and may pass through a mucosal barrier in the subject (e.g., mucus), and/or may show prolonged retention and/or increased uniform distribution of the particles of the invention at the mucosal surface, e.g., due to reduced mucoadhesion. In certain embodiments, the pharmaceutical compositions are useful in increasing the bioavailability of the pharmaceutical agent in the subject. In certain embodiments, the pharmaceutical compositions are useful in increasing the concentration of the pharmaceutical agent in the subject. In certain embodiments, the pharmaceutical compositions are useful in increasing the exposure of the pharmaceutical agent in the subject. Moreover, the pharmaceutical compositions may be useful in treating and/or preventing a disease (e.g., ocular disease) in a subject.

Moreover, the pharmaceutical compositions may be administered parenterally as injections (intravenous, intramuscular, or subcutaneous), drop infusion preparations, or suppositories. For ophthalmic applications, the pharmaceutical compositions may be administered by injection (e.g., intraocular, intrastromal, intravitreal, or intracameral), or by the ophthalmic mucous membrane route, the pharmaceutical compositions may be administered topically, such as suspensions (e.g., eye drops) or ointments.

The pharmaceutical composition of the invention may include one or more pharmaceutical agents described herein, such as a compound of the invention. In certain embodiments, the pharmaceutical composition includes a plurality of particles of the invention that comprise one or more pharmaceutical agents in the core and/or coating of the particles. In some embodiments, the ratio of the weight of each one of the pharmaceutical agents to the weight of each one of the one or more surface-altering agents (e.g., PLURONIC® F127) present in the pharmaceutical composition is greater than or equal to about 1:100, greater than or equal to about 1:30, greater than or equal to about 1:10, greater than or equal to about 1:3, greater than or equal to about 1:1, greater than or equal to about 3:1, greater than or equal to about 10:1, greater than or equal to about 30:1, or greater than or equal to about 100:1. In some embodiments, the ratio of the weight of each one of the pharmaceutical agents to the weight of each one of the one or more surface-altering agents in a pharmaceutical composition is less than about 100:1, less than about 30:1, less than about 10:1, less than about 3:1, less than about 1:1, less than about 1:3: less than about 1:10, less than about 1:30, or less than about 1:100. Combinations of the above-noted ranges are possible (e.g., a ratio of greater than or equal to about 1:1 and less than about 10:1). Other ranges are also possible. In certain embodiments, the ratio is about 1:1, about 2:1, or about 10:1. In some embodiments, the pharmaceutical composition of the invention includes the above-noted ranges for the ratio of the weight of each one of the pharmaceutical agents to the weight of each one of the one or more surface-altering agents during a formation process and/or a dilution process described herein. In certain embodiments, the pharmaceutical composition includes the above-noted ranges for the ratio of the weight of each one of the pharmaceutical agents to the weight of each one of the one or more surface-altering agents immediately prior to the pharmaceutical composition being administered to a subject or contacted with a biological sample. The pharmaceutical agent may be present in the pharmaceutical composition of the invention in any suitable amount, e.g., at least about 0.01 wt %, at least about 0.1 wt %, at least about 1 wt %, at least about 5 wt %, at least about 10 wt %, at least about 30 wt % of the pharmaceutical composition. In some cases, the pharmaceutical agent may be present in the pharmaceutical composition at less than about 30 wt %, less than about 10 wt %, less than about 5 wt %, less than about 2 wt %, or less than about 1 wt % of the pharmaceutical composition.

Combinations of the above-referenced ranges are also possible (e.g., present in an amount of at least about 0.1 wt % and less than about 10 wt % of the pharmaceutical composition). Other ranges are also possible. In certain embodiments, the pharmaceutical agent is about 0.1-2 wt % of the pharmaceutical composition. In certain embodiments, the pharmaceutical agent is about 2-20 wt % of the pharmaceutical composition. In certain embodiments, the pharmaceutical agent is about 0.2 wt %, about 0.4 wt %, about 1 wt %, about 2 wt %, about 5 wt %, or about 10 wt % of the pharmaceutical composition.

In certain embodiments, the pharmaceutical composition includes a plurality of particles of the invention that comprise the chelating agent in the core and/or coating of the particles.

In certain embodiments, the pharmaceutical composition includes a plurality of particles of the invention that comprise a tonicity agent in the core and/or coating of the particles.

It is appreciated in the art that the ionic strength of an inventive pharmaceutical composition that comprises a plurality of particles of the invention may affect the polydispersity of the plurality of the particles. The ionic strength may also affect the colloidal stability of the plurality of the particles. For example, a relatively high ionic strength of the pharmaceutical composition may cause the plurality of particles to coagulate and therefore may destabilize the pharmaceutical composition. In some embodiments, the pharmaceutical composition is stabilized by repulsive inter-particle forces. For example, the plurality of particles may be electrically or electrostatically charged. Two charged particles may repel each other, preventing collision and aggregation. When the repulsive inter-particle forces weaken or become attractive, the plurality of particles may start to aggregate. For instance, when the ionic strength of the pharmaceutical composition is increased to a certain level, the charges (e.g., negative charges) of the plurality of particles may be neutralized by the oppositely charged ions present in the pharmaceutical composition (e.g., $Na^+$ ions in solution). As a result, the plurality of particles may collide and bond to each other to form aggregates (e.g., clusters or flocs) of larger sizes. The formed aggregates of particles may also differ in size, and thus the polydispersity of the pharmaceutical composition may also increase. For example, an inventive pharmaceutical composition comprising similarly-sized particles may become a pharmaceutical composition comprising particles having various sizes (e.g., due to aggregation) when the ionic strength of the pharmaceutical composition is increased beyond a certain level. In the course of aggregation, the aggregates may grow in size and eventually settle to the bottom of the container, and the pharmaceutical composition is considered colloidally unstable. Once the plurality of particles in a pharmaceutical composition form aggregates, it is usually difficult to disrupt the aggregates into individual particles.

Certain pharmaceutical compositions of the invention show unexpected properties in that, among other things, the presence of one or more ionic tonicity agents (e.g., a salt, such as NaCl) in the pharmaceutical compositions at certain concentrations actually decreases or maintains the degree of aggregation of the particles present in the pharmaceutical compositions, and/or does not significantly increase aggregation. In certain embodiments, the polydispersity of the pharmaceutical composition decreases, is relatively constant, or does not change by an appreciable amount upon addition of one or more ionic tonicity agents into the pharmaceutical composition. For example, in some embodiments, the polydispersity of a pharmaceutical composition is relatively constant in the presence of added ionic strength and/or when the added ionic strength of the pharmaceutical composition is kept relatively constant or increased (e.g., during a formation and/or dilution process described herein). In certain embodiments, when the ionic strength increases by at least 50%, the polydispersity increases by less than about 300%, less than about 100%, less than about 30%, less than about 10%, less than about 3%, or less than about 1%. In certain embodiments, when the ionic strength is increased by at least 50%, the polydispersity increases by greater than or equal to about 1%, greater than or equal to about 3%, greater than or equal to about 10%, greater than or equal to about 30%, or greater than or equal to about 100%. Combinations of the above-noted ranges are possible (e.g., an increase in polydispersity of less than 30% and greater than or equal to 3%). Other ranges are also possible.

The ionic strength of a pharmaceutical composition of the invention may be controlled (e.g., increased, decreased, or maintained) through a variety of means, such as the addition of one or more ionic tonicity agents (e.g., a salt, such as NaCl) to the pharmaceutical composition. In certain embodiments, the ionic strength of a pharmaceutical composition of the invention is greater than or equal to about 0.0003 M, greater than or equal to about 0.001 M, greater than or equal to about 0.003 M, greater than or equal to about 0.01 M, greater than or equal to about 0.03 M, greater than or equal to about 0.1 M, greater than or equal to about 0.3 M, greater than or equal to about 1 M, greater than or equal to about 3 M, or greater than or equal to about 10 M. In certain embodiments, the ionic strength of a pharmaceutical composition of the invention is less than about 10 M, less than about 3 M, less than about 1 M, less than about 0.3 M, less than about 0.1 M, less than about 0.03 M, less than about 0.01 M, less than about 0.003 M, less than about 0.001 M, or less than about 0.0003 M. Combinations of the above-noted ranges are possible (e.g., an ionic strength of greater than or equal to about 0.01 M and less than about 1 M). Other ranges are also possible. In certain embodiments, the ionic strength of a pharmaceutical composition of the invention is about 0.1 M, about 0.15 M, or about 0.3 M.

In certain embodiments, the polydispersity of a pharmaceutical composition does not change upon addition of one or more ionic tonicity agents into the pharmaceutical composition. In certain embodiments, the polydispersity does not significantly increase upon addition of one or more ionic tonicity agents into the pharmaceutical composition. In certain embodiments, the polydispersity increases to a level described herein upon addition of one or more ionic tonicity agents into the pharmaceutical composition.

The polydispersity of an inventive pharmaceutical composition that comprises a plurality of particles of the invention may be measured by the polydispersity index (PDI). In certain embodiments, the PDI of the pharmaceutical composition is less than about 1, less than about 0.8, less than about 0.6, less than about 0.4, less than about 0.3, less than about 0.2, less than about 0.15, less than about 0.1, less than about 0.05, less than about 0.01, or less than about 0.005. In certain embodiments, the PDI of the pharmaceutical composition is greater than or equal to about 0.005, greater than or equal to about 0.01, greater than or equal to about 0.05, greater than or equal to about 0.1, greater than or equal to about 0.15, greater than or equal to about 0.2, greater than or equal to about 0.3, greater than or equal to about 0.4, greater than or equal to about 0.6, greater than or equal to about 0.8, or greater than or equal to about 1. Combinations of the above-noted ranges are possible (e.g., a PDI of greater than or equal to about 0.1 and less than about 0.5). Other ranges are also possible. In certain embodiments, the PDI of the pharmaceutical composition is about 0.1, about 0.15, or about 0.2. In certain embodiments, the pharmaceutical composition is highly dispersible and does not tend to form aggregates. Even when the particles do form aggregates, the aggregates may be easily broken up into individual particles without rigorously agitating the pharmaceutical composition.

Methods of Preparing Particles and Pharmaceutical Compositions thereof

In one aspect, the present invention provides methods of preparing the particles of the invention. Methods of preparing similar particles have been described in U.S. patent application Ser. No. 13/886,493, filed May 3, 2013, and U.S. Ser. No. 13/886,602, filed May 3, 2013, and U.S. Ser. No. 13/886,658, filed May 3, 2013, each of which is incorporated by reference herein in its entirety.

The core of the particle may be formed by any suitable method. Suitable methods may include, for example, top-down techniques, i.e. techniques based on size reduction of relatively large particles into smaller particles (e.g., milling or homogenization) or bottom-up techniques, i.e. techniques based on the growth of particles from smaller particles or individual molecules (e.g., precipitation or spray-freezing into liquid).

In some embodiments, the core of the particle may be coated with a coating. For example, the core may be provided or formed in a first step, and then the core may be coated in a second step. In some embodiments, the core particle is formed and coated substantially simultaneously (e.g., in a single step).

In some embodiments, the particle is formed by a method that involves using a formulation process, a milling process, and/or a dilution process. In certain embodiments, a method of forming the particle includes a milling process, optionally with a formulation process and/or a dilution process. A formulation process may be used to form a suspension comprising a core material, one or more surface-altering agents, and other components, such as solvents, tonicity agents, chelating agents, salts, and/or buffers (e.g., a sodium citrate and citric acid buffer), each of which is as described herein. The formulation process may be performed using a formulation vessel. The core material and other components may be added into the formulation vessel at the same time or different times. A mixture of the core material and/or one or more other components may be stirred and/or shaken, or otherwise agitated in the vessel to facilitate suspending the components to form the suspension. The temperature and/or pressure of the core material, other components, and/or mixture may also be individually increased or decreased to facilitate the suspending process. In some embodiments, the core material and other components are processed as described herein in the formulation vessel under an inert atmosphere (e.g., nitrogen or argon) and/or protected from light. The suspension obtained from the formulation vessel may be subsequently subject to a milling process which may be followed by a dilution process.

In some embodiments involving a core comprising a solid material (e.g., crystalline compound of the invention) a milling process may be used to reduce the size of the solid material to form particles in a micrometer to nanometer size range. The milling process may be performed using a mill or other suitable apparatus. Dry and wet milling processes such as jet milling, cryo-milling, ball milling, media milling, sonication, and homogenization are known and can be used in methods of the invention. For example, in a wet milling process, a suspension of the solid material to be used to form the core ("core material") is agitated with or without excipients to reduce the size of the core to be formed. Dry milling is a process wherein the core material is mixed with milling media with or without excipients to reduce the size of the core to be formed. In a cyro-milling process, a suspension of the core material is mixed with milling media with or without excipients under cooled temperatures. In certain embodiments, when surface-altering agents are employed, a suspension comprising coated particles is obtained from the milling process. In certain embodiments, when surface-altering agents are not employed, a suspension comprising uncoated particles is obtained from the milling process.

The suspension of particles (coated or uncoated) of the invention obtained from a milling process may be further processed with a dilution process. A dilution process may be used to achieve a target dosing concentration by diluting a suspension of particles that were formed during a milling process, with or without surface-altering agents and/or other components. In certain embodiments, when a suspension of coated particles that comprise a first surface-altering agent is processed with a dilution process involving a second surface-altering agent, a suspension of coated particles that comprise the second surface-altering agent is obtained from the dilution process. In certain embodiments, when a suspension of coated particles that comprise a surface-altering agent is processed with a dilution process involving no or the same surface-altering agent, a suspension of coated particles that comprise the surface-altering agent is obtained from the dilution process. In certain embodiments, when a suspension of uncoated particles is processed with a dilution process involving a surface-altering agent, a suspension of coated particles comprising the surface-altering agent is obtained from the dilution process. The dilution process may be performed using a product vessel or any other suitable apparatus. In certain embodiments, the suspension of the particles is diluted, i.e., mixed or otherwise processed with a diluent, in the product vessel. The diluent may contain solvents, surface-altering agents, tonicity agents, chelating agents, salts, or a combination thereof, as described herein. The suspension and the diluent may be added into the product vessel at the same time or different times. In certain embodiments when the suspension is obtained from a milling process involving milling media, the milling media may be separated from the suspension before the suspension is added into the product vessel. The suspension, the diluent, or the mixture of the suspension and the diluent may be stirred and/or shaken, or otherwise agitated, to form the particles and/or pharmaceutical compositions of the invention. The temperature and/or pressure of the suspension, the diluent, or the mixture may also be individually increased or decreased to form the coated particles. In some embodiments, the suspension and the diluent are processed in the product vessel under an inert atmosphere (e.g., nitrogen or argon) and/or protected from light.

In some embodiments, the core and/or coated particles may be produced by milling of a solid material (e.g., a pharmaceutical agent) in the presence of one or more surface-altering agents. Small particles of a solid material may require the presence of one or more surface-altering agents, which may function as a stabilizer in some embodiments, in order to stabilize a suspension of particles without agglomeration or aggregation in a liquid solution. In some such embodiments, the stabilizer may act as a surface-altering agent, forming the coated particles of the invention.

As described herein, a method of forming the core and/or the coated particles, may involve choosing a surface-altering agent that is suitable for both milling and forming a coating on the core, wherein the coating renders the particle mucus penetrating.

In a wet milling process, milling may be performed in a dispersion (e.g., an aqueous dispersion) containing at least one surface-altering agent, a grinding medium, a solid to be milled (e.g., a solid pharmaceutical agent), and a solvent. The solvent described herein includes a single solvent or a mixture of different solvents. Any suitable amount of a surface-altering agent can be included in the solvent. In some embodiments, the surface-altering agent may be present in the solvent in an amount of at least about 0.001% (wt % or % weight to volume (w:v)), at least about 0.01%, at least about 0.1%, at least about 1%, at least about 3%, at least about 10%, at least about 30%, or at least about 60% of the solvent. In some cases, the surface-altering agent may be present in the solvent in an amount of about 100% (e.g., in an instance where the surface-altering agent is the solvent). In other embodiments, the surface-altering agent may be present in the solvent in an amount of less than about 100%, less than about 60%, less than about 30%, less than about 10%, less than about 3%, or less than about 1% of the solvent. Combinations of the above-referenced ranges are also possible (e.g., an amount of less than about 3% and at least about 1% of the solvent). Other ranges are also possible. In certain embodiments, the surface-altering agent is present in the solvent in an amount of about 0.01-2%, about 0.2-20%, about 0.1%, about 0.4%, about 1%, about 2%, about 5%, or about 10% of the solvent.

The particular range chosen may influence factors that may affect the ability of the particles to penetrate mucus such as the stability of the coating of the surface-altering agent on the particle surface, the average thickness of the coating of the surface-altering agent on the particles, the orientation of the surface-altering agent on the particles, the density of the surface altering agent on the particles, the ratio of the surface-altering agent to pharmaceutical agent, the concentration of the pharmaceutical agent, the size, dispersibility, and polydispersity of the particles formed, and the morphology of the particles formed.

The pharmaceutical agent may be present in the solvent in any suitable amount. In some embodiments, the pharmaceutical agent is present in an amount of at least about 0.001% (wt % or % weight to volume (w:v)), at least about 0.01%, at least about 0.1%, at least about 1%, at least about 3%, at least about 10%, at least about 30%, or at least about 60% of the solvent. In some cases, the pharmaceutical agent may be present in the solvent in an amount of less than about 100%, less than about 60%, less than about 30%, less than about 10%, less than about 3%, or less than about 1% of the solvent. Combinations of the above-referenced ranges are also possible (e.g., an amount of less than about 30% and at least about 1% of the solvent).

The ratio of surface-altering agent to pharmaceutical agent in a solvent may also vary. In some embodiments, the ratio of the surface-altering agent to pharmaceutical agent is at least about 0.001:1 (weight ratio, molar ratio, or w:v), at least about 0.01:1, at least about 0.01:1, at least about 1:1, at least about 2:1, at least about 3:1, at least about 5:1, at least about 10:1, at least about 30:1, at least about 100:1, or at least about 1000:1. In some embodiments, the ratio of the surface-altering agent to pharmaceutical agent is less than 1000:1 (weight ratio, molar ratio, or w:v), less than about 100:1, less than about 30:1, less than about 10:1, less than about 5:1, less than about 3:1, less than about 2:1, less than about 1:1, or less than about 0.1:1. Combinations of the above-referenced ranges are possible (e.g., a ratio of at least about 5:1 and less than about 30:1). Other ranges are also possible.

The surface-altering agents described herein that may act as stabilizers may be, for example, polymers or surfactants. Examples of polymers include those suitable for use in the coating of the particles of the invention, such as poly(vinyl alcohol) and PLURONICS®. Examples of surfactants include L-α-phosphatidylcholine (PC), 1,2-dipalmitoyl-phosphatidycholine (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol, cetyl pyridinium chloride, benzalkonium chloride, olive oil, glyceryl monolaurate, corn oil, cotton seed oil, and sunflower seed oil.

A stabilizer used for milling may form the coating of a particle of the invention, wherein the coating renders the particle mucus penetrating. The stabilizer may also be exchanged with one or more other surface-altering agents after the particle has been formed. For example, a first stabilizer/surface-altering agent may be used during a milling process and may form a first coating of the particle of the invention, and all or part of the first stabilizer/surface-altering agent may then be exchanged with a second stabilizer/surface-altering agent to form a second coating of the particle. In some embodiments, the second stabilizer/surface-altering agent may render the particle mucus penetrating more than the first stabilizer/surface-altering agent. In some embodiments, a particle comprising multiple coatings that include multiple surface-altering agents is formed by a method of the invention.

Any suitable grinding medium can be used for milling. In some embodiments, a ceramic and/or polymeric material and/or a metal can be used. Examples of suitable materials include zirconium oxide, silicon carbide, silicon oxide, silicon nitride, zirconium silicate, yttrium oxide, glass, alumina, alpha-alumina, aluminum oxide, polystyrene, poly (methyl methacrylate), titanium, and steel. A grinding medium may have any suitable size. For example, the grinding medium may have an average diameter of at least about 0.1 mm, at least about 0.2 mm, at least about 0.5 mm, at least about 0.8 mm, at least about 1 mm, at least about 2 mm, or at least about 5 mm. In some cases, the grinding medium may have an average diameter of less than about 5 mm, less than about 2 mm, less than about 1 mm, less than about 0.8, less than about 0.5 mm, or less than about 0.2 mm. Combinations of the above-referenced ranges are also possible (e.g., an average diameter of at least about 0.5 millimeters and less than about 1 mm). Other ranges are also possible.

A solvent may be used for milling. The choice of the solvent suitable for milling may depend on factors like the solid material (e.g., a solid pharmaceutical agent) being milled, the particular type of stabilizer/surface-altering agent (e.g., one that may render the particle mucus penetrating), and the grinding material. The solvent suitable for milling may be one of those solvents that do not substantially dissolve the solid material or the grinding material, but dissolve the stabilizer/surface-altering agent to a suitable degree. Examples of the solvents suitable for milling include water, aqueous solutions, buffered solutions, alcohols (e.g., ethanol, methanol, and butanol), and mixtures thereof, each of which may optionally include other components, such as one or more pharmaceutical excipients, polymers, pharmaceutical agents, salts, preservative agents, viscosity modifiers, tonicity modifiers, taste masking agents, antioxidants, and pH modifiers. In some embodiments, the solvent suitable for milling is an organic solvent.

A pharmaceutical agent described herein (e.g., a compound of the invention) may have a suitable solubility in a solvent suitable for milling, such as a solubility in one or more ranges described herein for aqueous solubility or for solubility in a coating solution. A pharmaceutical agent having a relatively low solubility in a solvent (e.g., water or a coating solution) may be preferred because a milling process described herein typically requires a material (e.g., a pharmaceutical agent) to be in a solid form in order for the material to be milled. In some cases, if the material to be milled has a relatively high soluble in a solvent (e.g., water or a coating solution) used in the milling process, milling may not be conducted because significant or complete dissolution of the material to be milled in the solvent will occur. In certain embodiments, a relatively high solubility of a solid material (e.g., a solid pharmaceutical agent) in a solvent is at least about 1 mg/mL, at least about 3 mg/mL, or at least about 10 mg/mL at 25° C. In certain embodiments, a relatively low solubility of a substance (e.g., a pharmaceutical agent) in a solvent is less than about 1 mg/mL, less than about 0.3 mg/mL, less than about 0.1 mg/mL, less than about 0.03 mg/mL, less than about 0.01 mg/mL, less than about 0.003 mg/mL, or less than about 0.001 mg/mL at 25° C. The solid material may have these or other ranges of solubilities at any point throughout the pH range (e.g., from pH 1 to pH 14). A pharmaceutical agent that has a relatively high solubility in the solvent used in the milling process may be modified to form a prodrug of the pharmaceutical agent. The prodrug may have a relatively low solubility and thus may be suitable for the milling process. Upon or after the particles or pharmaceutical compositions comprising the prodrug are administered to a subject, the prodrug may be converted and form or, in other words, "release," the pharmaceutical agent.

In other embodiments, the core and/or coated particles may be formed by an emulsification process or technique (emulsification) known in the art. See, e.g., U.S. patent application Ser. No. 13/886,602. The core and/or coated particles may also be formed by a precipitation process or technique (precipitation). Precipitation techniques (e.g., microprecipitation, nanoprecipitation, crystallization, and controlled crystallization) may involve forming a first solution comprising the material that is to form the core (e.g., a pharmaceutical agent) and a first solvent, wherein the material has a relatively high solubility in the first solvent. The first solution may be added to a second solution comprising a second solvent that is an anti-solvent, in which the material has a relatively low solubility, thereby forming a plurality of particles comprising the material. In certain embodiments, the second solvent is miscible with the first solvent. In some embodiments, one or more surface-altering agents and/or surfactants may be present in the first and/or second solutions. A coating may be formed during the process of precipitating the core (e.g., the coating of the particles may be formed substantially simultaneously when the precipitation is performed) to form the coated particles of the invention.

In other embodiments, the core of the particles of the invention is first formed using a precipitation technique, following by coating of the core with a surface-altering agent to form the coated particles of the invention.

In some embodiments, a precipitation technique may be used to form polymeric core of the particles of the invention with or without a pharmaceutical agent. Generally, a precipitation technique involves dissolving a polymer that is to form the core in a first solvent, in the presence or absence of a pharmaceutical agent, to form a solution. The solution is then added to a second solvent that is an anti-solvent and is miscible with the first solvent, in the presence or absence of one or more excipients, to form the core of the particles. In some embodiments, precipitation is useful for preparing a polymeric core comprising one or more pharmaceutical agents having a relatively low aqueous solubility.

The precipitation described herein involves the use of a first solvent. Examples of suitable first solvents for precipitation include organic solvents (e.g., acetone, acetonitrile, dimethylformamide, dimethysulfoxide, N-methyl-2-pyrrolidone, 2-pyrrolidone, and tetrahydrofuran) and inorganic solvents.

The precipitation described herein also involves the use of a second solvent. In certain embodiments, the second solvent suitable for precipitation is an anti-solvent. Examples of second solvents suitable for precipitation include the solvents described herein that may be used for milling. In some embodiments, the second solvents suitable for precipitation is water, an aqueous solution (e.g., a buffered solution), an alcohol (e.g., methanol, ethanol, propanol, or butanol), or a mixture thereof, optionally including one or more other components, such as pharmaceutical excipients, polymers, and pharmaceutical agents.

Surface-altering agents for the emulsification and precipitation described herein may be polymers or surfactants, including the surface-altering agents described herein that may be used for milling.

Examples of polymers suitable for forming all or part of the core of the particles of the invention by the emulsification or precipitation include the polymers (including copolymers) described herein.

In some embodiments, a precipitation technique may be used to form particles comprised predominantly of a pharmaceutical agent (e.g., a compound of the invention). In certain embodiments, the particles of the invention formed by the precipitation technique comprise predominantly of a pharmaceutical agent that is a nanocrystal. Generally, such a precipitation technique involves dissolving the pharmaceutical agent that is to form the core in a first solvent, which is then added to a second solvent that is an anti-solvent, in which the pharmaceutical agent has a relatively low solubility, in the presence or absence of one or more pharmaceutical excipients, to form the core or uncoated particle. In some embodiments, this technique may be useful for preparing, for example, particles of pharmaceutical agents that are slightly soluble (1-10 mg/mL), very slightly soluble (0.1-1 mg/mL) or practically insoluble (<0.1 mg/mL) in aqueous solutions (e.g., agents having a relatively low aqueous solubility).

A pharmaceutical agent described herein (e.g., a compound of the invention) may have a suitable solubility in the first and second solvents suitable for precipitation, such as a solubility in one or more ranges described herein for aqueous solubility or for solubility in a coating solution. A pharmaceutical agent having a relatively high solubility in the first solvent (e.g., an organic solvent) may be preferred. In certain embodiments, the pharmaceutical agent substantially or completely dissolves in the first solvent. A pharmaceutical agent having a relatively low solubility in the second solvent (e.g., water or a coating solution) may also be preferred. In certain embodiments, the solubility of the pharmaceutical agent in a mixture of the first and second solvents is lower than the solubility of the pharmaceutical agent in the first solvent. The relatively high solubility and relatively low solubility are as described herein. A pharmaceutical agent that has a relatively high solubility in the second solvent may be modified to form a prodrug of the pharmaceutical agent. The prodrug may have a relatively low solubility in the second solvent and still have a relatively high solubility in the first solvent and thus may be suitable for precipitation. Upon or after the particles or pharmaceutical compositions comprising the prodrug are administered to a subject, the prodrug may be converted and form or, in other words, "release," the pharmaceutical agent.

Precipitation by formation of a salt or complex may also be used to form particles comprised predominantly of a salt or complex of a pharmaceutical agent. In certain embodiments, the particles formed by this specific precipitation technique comprise predominantly of a pharmaceutical agent that is a nanocrystal. Generally, precipitation by formation of a salt or complex involves dissolving a pharmaceutical agent that is to form the core in a solvent, in the presence or absence of one or more excipients, followed by the addition of a counterion or a complexing agent, which forms a salt or a complex with the pharmaceutical agent to form the core. All counterions described herein are contemplated to be within the scope of the invention. This technique may be useful for preparing particles comprising pharmaceutical agents that have a relatively high solubility in the second solvent (e.g., water or a coating solution). In certain embodiments, the pharmaceutical agent has a relatively high solubility in the second solvent, and the salt or complex of the pharmaceutical agent has a relatively low solubility in the second solvent. The relatively high solubility and relatively low solubility are as described herein. In some embodiments, pharmaceutical agents having one or more charged or ionizable groups interact with a counterion (e.g., a cation or an anion) to form a salt or complex.

A variety of different acids may be used in a precipitation process involving formation of a salt or complex. Examples of acids suitable for precipitation include deconoic acid, hexanoic acid, mucic acid, octanoic acid. In other embodiments, a suitable acid may include acetic acid, adipic acid, L-ascorbic acid, L-aspartic acid, capric acid (decanoic acid), carbonic acid, citric acid, fumaric acid, galactaric acid, D-glucoheptonic acid, D-gluconic acid, D-glucuronic acid, glutamic acid, glutaric acid, glycerophosphoric acid, glycolic acid, hippuric acid, hydrochloric acid, DL-lactic acid, lauric acid, maleic acid, (−)-L-malic acid, palmitic acid, phosphoric acid, sebacic acid, stearic acid, succinic acid, sulfuric acid, (+)-L-tartaric acid, or thiocyanic acid. In other embodiments, a suitable acid may include alginic acid, benzenesulfonic acid, benzoic acid, (+)-camphoric acid, caprylic acid (octanoic acid), cyclamic acid, dodecylsulfuric acid, ethane-1,2-disulfonic acid, ethanesulfonic acid, ethanesulfonic acid, 2-hydroxy-, gentisic acid, glutaric acid, 2-oxo-, isobutyric acid, lactobionic acid, malonic acid, methanesulfonic acid, naphthalene-1,5-disulfonic acid, naphthalene-2-sulfonic acid, 2-naphthoic acid, 1-hydroxy-, nicotinic acid, oleic acid, orotic acid, oxalic acid, pamoic acid, (embonic acid), propionic acid, (−)-L-pyroglutamic acid, or p-toluenesulfonic acid. In yet other embodiments, a suitable acid may include acetic acid, 2,2-dichloro-, benzoic acid, 4-acetamido-, (+)-camphor-10-sulfonic acid, caproic acid (hexanoic acid), cinnamic acid, formic acid, hydrobromic acid, DL-mandelic acid, nitric acid, salicylic acid, salicylic acid, 4-amino-, and undecylenic acid (undec-10-enoic acid). Mixtures of two or more acids can also be used.

A variety of different bases may also be used in a precipitation process involving formation of a salt or complex. Examples of bases suitable for precipitation include ammonia, L-arginine, calcium hydroxide, choline, glucamine, N-methyl-, lysine, magnesium hydroxide, potassium hydroxide, or sodium hydroxide. In other embodiments, a suitable base may include benethamine, benzathine, betaine, deanol, diethylamine, ethanol, 2-(diethylamino)-, hydrabamine, morpholine, 4-(2-hydroxyethyl)-, pyrrolidine, 1-(2-hyroxyethyl)-, or tromethamine. In other embodiments, a suitable base may include diethanolamine (2,2'-iminobis (ethanol)), ethanolamine (2-aminoethanol), ethylenediamine, IH-imidazole, piperazine, triethanolamine (2,2',2"-nitrilotris(ethanol)), and zinc hydroxide. Mixtures of two or more bases can also be used.

Examples of solvents suitable for precipitation involving formation of a salt or complex include the solvents described herein that may be used for milling. In some embodiments, the first or second solvent suitable for precipitation involving formation of a salt or complex is water, an aqueous solution (e.g., a buffered solution), an alcohol (e.g., methanol, ethanol, propanol, or butanol), or a mixture thereof, optionally including one or more other components, such as pharmaceutical excipients, polymers, and pharmaceutical agents.

The first or second solvent suitable for precipitation may include one or more surface-altering agents as described herein, and therefore, a coating comprising the one or more surface-altering agents may be formed around the core to provide the coated particles of the invention as they precipitate out of solution. The one or more surface-altering agents may be present in the first or second solvent at any suitable concentration, such as a concentration of at least about 0.001% (w/v), at least about 0.003% (w/v), at least about 0.01% (w/v), at least about 0.03% (w/v), at least about 0.1% (w/v), at least about 0.3% (w/v), at least about 1% (w/v), or at least about 3% (w/v). In some embodiments, the one or more surface-altering agents are present in the first or second solvent at a concentration of less than about 3% (w/v), less than about 1% (w/v), less than about 0.3% (w/v), less than about 0.1% (w/v), less than about 0.05% (w/v), less than about 0.01% (w/v), or less than about 0.003% (w/v). Combinations of the above-referenced ranges are also possible (e.g., a concentration of at least about 0.01 (w/v) and less than about 1% (w/v). Other ranges are also possible. In certain embodiments, the one or more surface-altering agents are present in the first solvent but absent in the second solvent. In certain embodiments, the one or more surface-altering agents are present in the second solvent but absent in the first solvent. In certain embodiments, the one or more surface-altering agents are present in both the first and second solvents.

Another exemplary method of forming the core and/or coated particle is a freeze-drying process or technique known in the art. See, e.g., U.S. patent application Ser. No. 13/886,602.

Other methods of forming core particles are also possible. For example, additional techniques of forming the core and/or coated particles include coacervation-phase separation, melt dispersion, interfacial deposition, in situ polymerization, self-assembly of macromolecules (e.g., formation of polyelectrolyte complexes or polyelectrolyte-surfactant complexes), spray-drying and spray-congealing, electrospray, air suspension coating, pan and spray coating, freeze-drying, air drying, vacuum drying, fluidized-bed drying, precipitation (e.g., nanoprecipitation, microprecipitation), critical fluid extraction, and lithographic approaches (e.g., soft lithography, step and flash imprint lithography, interference lithography, and photolithography). Combinations of the methods described herein are also possible. In some embodiments, a core of a pharmaceutical agent is first formed by precipitation, and then the size of the core is reduced by a milling process, optionally a coating is form on the core by the milling process.

Following the formation of the core of the particles including a pharmaceutical agent, the core may be optionally exposed to a solution comprising a (second) surface-altering agent that may associate with and/or coat the core. In embodiments in which the pharmaceutical agent already includes a coating of a first surface-altering agent, all or part of the first surface-altering agent may be exchanged with a second surface-altering agent. In some embodiments, the second surface-altering agent renders the particle mucus penetrating more than the first surface-altering agent does. In some embodiments, a particle having a coating including multiple surface-altering agents is formed (e.g., in a single layer or in multiple layers). In some embodiments, a particle having multiple coatings (e.g., each coating optionally comprising different surface-altering agents) may be formed. In some embodiments, the coating is in the form of a monolayer of a surface-altering agent. Other configurations are also possible.

In any of the methods described herein, a coating comprising a surface-altering agent may be formed on a core of the particles of the invention by incubating the core in a solution including the surface-altering agent for a period of at least about 1 minute, at least about 3 minutes, at least about 10 minutes, at least about 20 minutes, at least about 30 minutes, at least about 60 minutes, or more. In some cases, incubation may take place for a period of less than about 10 hours, less than about 3 hours, or less than about 60 minutes. Combinations of the above referenced ranges are also possible (e.g., an incubation period of less than 60 minutes and at least about 1 minute).

Methods of Treating/Uses

The present invention provides compounds, particles, coated particles, and compositions thereof for treating a disease. In some embodiments, methods of treating a disease in a subject are provided which comprise administering an effective amount of a compound of Formula (I), (II), or (III), to a subject in need of treatment. In certain embodiments, the effective amount is a therapeutically effective amount. In certain embodiments, the effective amount is a prophylactically effective amount. In certain embodiments, the subject is suffering from a growth factor-associated disease. In certain embodiments, the subject is susceptible to a growth factor-associated disease. In certain embodiments, the subject is at risk of developing macular degeneration.

The present invention further provides methods of inhibiting VEGF activity or signaling in a cell. In some embodiments, such methods comprise contacting a cell with an effective amount of a compound of Formula (I), (II), or (III). In some embodiments, the cell is in vitro. In some embodiments, the cell is in vivo.

As used herein, the term "growth factor-associated disease" means any disease where growth factors are known to play a role. Accordingly, in some embodiments, the present disclosure relates to treating diseases in which growth factors are known to play a role. Such diseases include proliferative diseases, eye diseases, dermatological diseases, inflammation diseases, and metabolic diseases.

In some embodiments, the present disclosure provides methods of treating a disease comprising contacting a biological sample with an effective amount of a compound of Formula (I). In some embodiments, the present disclosure provides methods of treating a disease comprising contacting a biological sample with an effective amount of a compound of Formula (II). In certain embodiments, the present disclosure provides methods of treating a disease comprising contacting a biological sample with an effective amount of a compound of Formula (III). In certain embodiments, the biological sample includes a cell or tissue. In some embodiments, the methods comprise inhibiting growth factor signaling in a cell, tissue, or subject. In some embodiments, the biological sample is an ocular tissue. In certain embodiments, the method is an in vitro method. In certain embodiments, the method is an in vivo method. It will be understood by one of ordinary skill in the art that levels of inhibition are not necessary to be 100%. The levels of inhibition can be at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, or greater than 90% inhibition.

In some embodiments, the present disclosure provides methods to treat or prevent an ocular disease, i.e., a disease, ailment, or condition that affects or involves the eye or one or more of the parts or regions of the eye.

In some embodiments, the present disclosure provides a method to treat or prevent an ocular disease at the front of the eye of a subject. A front of the eye ocular disease includes post-surgical inflammation, uveitis, infections, aphakia, pseudophakia, astigmatism, blepharospasm, cataract, conjunctival diseases, conjunctivitis, corneal diseases, corneal ulcer, dry eye syndromes, eyelid diseases, lacrimal apparatus diseases, lacrimal duct obstruction, myopia, presbyopia, pupil disorders, corneal neovascularization, refractive disorders and strabismus. Glaucoma can be considered to be a front of the eye ocular condition in some embodiments because a clinical goal of glaucoma treatment can be to reduce a hypertension of aqueous fluid in the anterior chamber of the eye (i.e., reduce intraocular pressure).

In some embodiments, the present disclosure provides a method to target and/or treat portions within the posterior portion or back of the eye, such as the retina, the choroid, and/or the sclera, of a subject. In general, a back of the eye or posterior ocular disease is a disease, ailment, or condition which primarily affects or involves a tissue or fluid at the back of the eye, as described herein. A posterior ocular disease can include a disease, ailment, or condition, such as intraocular melanoma, acute macular neuroretinopathy, Behcet's disease, choroidal neovascularization, uveitis, diabetic uveitis, histoplasmosis, infections, such as fungal or viral-caused infections, macular degeneration, such as acute macular degeneration, non-exudative age-related macular degeneration and exudative age related macular degeneration, edema, such as macular edema, cystoid macular edema and diabetic macular edema, multifocal choroiditis, ocular trauma which affects a posterior ocular site or location, ocular tumors, retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease, sympathetic opthalmia, Vogt Koyanagi-Harada (VKH) syndrome, uveal diffusion, a posterior ocular condition caused by or influenced by an ocular laser treatment, posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, retinoblastoma, and glaucoma. Glaucoma can be considered a posterior ocular condition in some embodiments because the therapeutic goal is to prevent the loss of or reduce the occurrence of loss of vision due to damage to or loss of retinal cells or optic nerve cells (i.e., neuroprotection). In some embodiments, the present disclosure provides a method to treat, or prevent glaucoma in a subject. In some embodiments, the present disclosure provides a method to treat, or prevent uveitis in a subject.

In some embodiments, the present disclosure provides a method to treat or prevent dry eye in a subject. In some embodiments, the compositions described herein may address these issues by facilitating effective delivery of pharmaceutical agents to the appropriate tissues, promoting more even and/or wide-spread coverage across the eye surface, and/or avoiding or minimizing clearance of the pharmaceutical agent.

In some embodiments, the present disclosure provides a method to treat or prevent inflammation in the eye of a subject. Inflammation is associated with a variety of ocular diseases. Inflammation may also result from a number of ophthalmic surgical procedures, including cataract surgery.

In some embodiments, the present disclosure provides a method to treat or prevent age-related macular degeneration (AMD) in a subject. AMD is a medical condition that typically affects older adults and results in a loss of vision in the center of the visual field (the macula) because of damage to the retina. It occurs in "dry" and "wet" forms. It is a major cause of blindness and visual impairment in older adults (>50 years). In the dry (nonexudative) form, cellular debris called drusen accumulate between the retina and the choroid, and the retina can become detached. In the wet (exudative) form, which is more severe, blood vessels grow up from the choroid behind the retina, and the retina can also become detached.

In certain embodiments, the compounds, particles, compositions, and/or formulations described herein are packaged as a ready to use shelf stable suspension. Eye drop formulations are traditionally liquid formulations (solutions or suspensions) which can be packaged in dropper bottles (which dispense a standard drop volume of liquid) or in individual use droppers (typically used for preservative free drops, used once and disposed). These formulations are ready to use and can be self-administered. In some cases the bottle should be shaken before use to ensure homogeneity of the formulation, but no other preparation may be necessary. This may be the simplest and most convenient method of ocular delivery. The compositions and/or formulations described herein can be packaged in the same way as traditional eye drop formulations.

In some embodiments, compounds described here are useful in treating proliferative diseases, ocular diseases, dermatological diseases, inflammatory diseases, autoimmune diseases, autoinflammatory diseases, and metabolic diseases.

In some embodiments, a provided compound is useful in treating a cancer. In some embodiments, the present invention comprises a method to treat cancer. In some embodiments, a provided compound is useful to delay the onset of, slow the progression of, or ameliorate the symptoms of cancer. In some embodiments, a provided compound is administered in combination with other compounds, drugs, or therapeutics to treat cancer.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, a provided compound is useful in treating a metabolic disease, such as diabetes or obesity. In some embodiments, a provided compound is useful to delay the onset of, slow the progression of, or ameliorate the symptoms of, diabetes. In some embodiments, the diabetes is Type 1 diabetes. In some embodiments, the diabetes is Type 2 diabetes. In some embodiments, a provided compound is useful to delay the onset of, slow the progression of, or ameliorate the symptoms of, obesity. In some embodiments, a provided compound could be used in combination with other compounds, drugs, or therapeutics, such as metformin and insulin, to treat diabetes and/or obesity.

EXAMPLES

In order that the invention described herein may be more fully understood, the following examples are set forth. It should be understood that these examples are for illustrative purposes only and are not to be construed as limiting this invention in any manner.

Example 1

Synthesis of Compound 4 of Scheme 1

Compound 1: 4-(4-fluoro-2-methyl-1H-indol-5-yloxy)-7-(benzyloxy)-6-methoxyquinazoline

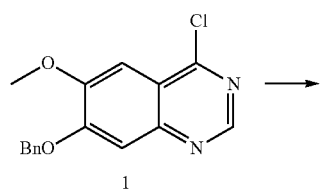

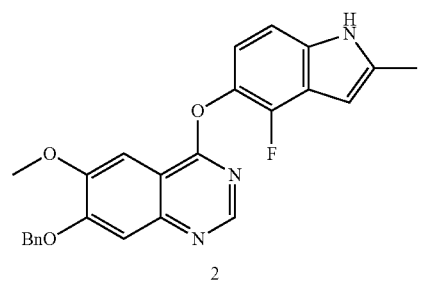

4-Fluoro-2-methyl-1H-indol-5-ol (0.53 g, 3.2 mmol) and was dissolved in N,N-dimethylfomamide (25 mL). The suspension was purged with nitrogen and potassium carbonate (0.92 g, 6.7 mmol) was added. 7-(Benzyloxy)-4-chloro-6-methoxyquinazoline (Compound 1, 1.0 g, 3.3 mmol) was added and the suspension was purged with nitrogen again. The suspension was heated overnight at 85° C. in an oil bath. The solvent was evaporated. The residue was treated with water (100 mL) and sonicated. The solid was filtered off, washed with water and hexanes, and dried in high vacuum overnight leaving Compound 2 as a gray solid (1.4 g, 100%). m/z: 430 (M+H, 100%) (positive ionization mode).

Compound 3: 4-(4-fluoro-2-methyl-1H-indol-5-yloxy)-6-methoxyquinazolin-7-ol

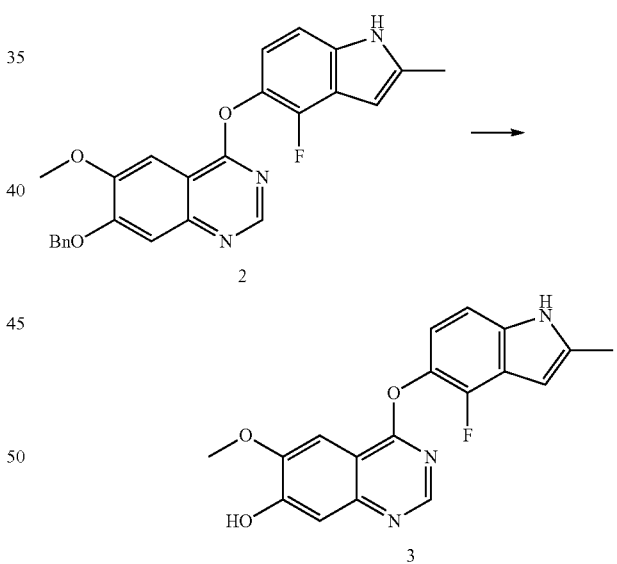

4-(4-fuoro-2-methyl-1H-indol-5-yloxy)-7-(benzyloxy)-6-methoxyquinazoline (Compound 2, 0.46 g, 1.1 mmol) was dissolved in N,N-dimethylformamide (10 mL). Palladium hydroxide catalyst (250 mg, 10% on carbon) was added, followed by ammonium formate (0.67 g, 10.6 mmol). The reaction solution was stirred for 2 hours at room temperature. The catalyst was filtered through a CELITE pad, then the solution was evaporated, then dried in high vacuum overnight to generate Compound 3 as a brown solid (0.36 g, 100%) m/z: 340 (M+H, 100%) (positive ionization mode).

115

Compound 4: 7-(3-(4-(4-fluoro-2-methyl-1H-indol-5-yloxy)-6-methoxyquinazolin-7-yloxy)propyl)-2-oxa-7-azaspiro[3.5]nonane

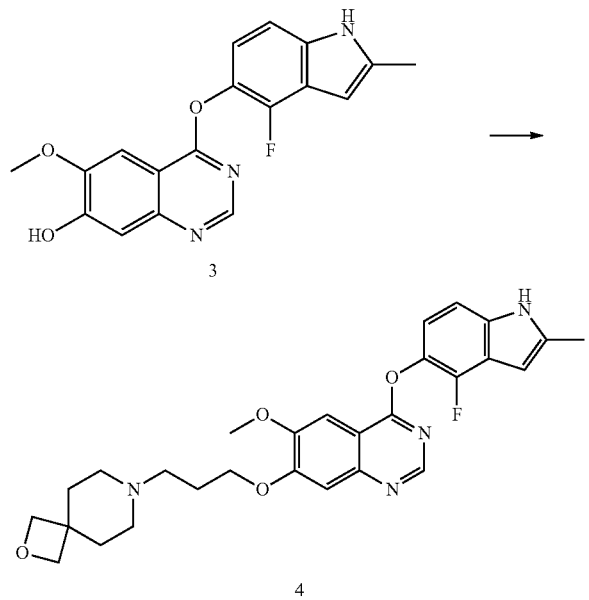

4-(4-fluoro-2-methyl-1H-indol-5-yloxy)-6-methoxyquinazolin-7-ol (Compound 3, 0.36 g, 1.1 mmol) was dissolved in N,N-dimethylformamide (10 mL). Potassium carbonate (0.90 g, 6.5 mmol) was added followed by 1-bromo-3-chloropropane (0.34 g, 2.2 mmol). The suspension was heated at 45° C. for 2 hours. The solvent was evaporated and the residue was suspended in dichloromethane (20 mL). The suspension was applied on a pad of silica gel. The impurities were eluted with dichloromethane and the compound was eluted with ethyl acetate (Rf=0.7 in ethyl acetate). The solvent was evaporated and the residue was dried in high vacuum leaving a yellow foam (0.35 g, 80%) m/z: 416 (M+H, 100%) (positive ionization mode), which was dissolved in N, N-dimethylformamide (5 mL). Potassium bromide (0.12 g, 1.0 mmol) was added followed by potassium carbonate (0.90 g, 7.8 mmol) and 2-oxa-7-azaspiro[3.5]nonane oxalate (0.35 g, 1.9 mmol). The suspension was heated at 85° C. for 4 hours. The solvent was evaporated and the residue was suspended in aqueous sodium bicarbonate (50 mL) and sonicated. The precipitate was filtered off. Drying in high vacuum gave a brown solid (0.34 g). Purification by reverse phase HPLC provided Compound 4 as an off-white solid (20 mg). m/z: 507 (M+H, 100%)(positive ionization mode). 1H NMR: (Chloroform-d): δ 8.60 (s, 1H), 8.10 (s, 1H), 7.65 (s, 1H); 7.35 (s, 1H), 7.10 (d, J=9.0 Hz 1H), 7.00 (dd, J=8.0; J=9.0 Hz, 1H), 6.35 (s, 1H), 4.45 (s, 4H), 4.35 (t, J=7.0 Hz, 2H), 4.15 (s, 3H), 2.55 (t, J=7.0 Hz, 2H), 2.46 (s, 3H), 2.40-2.35 (m, 4H), 2.15-2.10 (m, 2H), 1.90-1.85 (m, 4H).

116

Example 2

Synthesis of Compound 9

Compound 6: Ethyl 4-(4-chloro-6-methoxyquinazolin-7-yloxy)butanoate

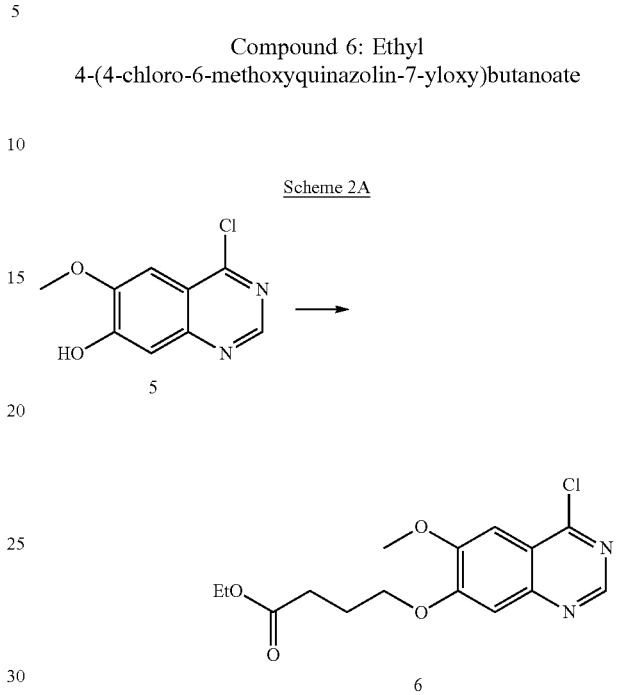

To a solution of 4-chloro-6-methoxyquinazolin-7-ol (compound 5, 3.0 g, 14.25 mmol) and ethyl 4-bromobutanoate (4.53 g, 28.49 mmol) in tetrahydrofuran (30 mL) was added potassium carbonate (5.90 g, 42.74 mmol) and the mixture was stirred overnight at room temperature. The reaction mixture was diluted with water (60 mL) and extracted with ethyl acetate (100 mL×2). The combined organic phases were concentrated to give the crude product as a yellow solid. The crude product was purified by silica gel column (gradient of hexane:ethyl acetate 10:1 to 2:1) to give Compound 6 (3.7 g) as a yellow solid.

Compound 7: Ethyl 4-(4-(4-fluoro-2-methyl-1H-indol-5-yloxy)-6-methoxyquinazolin-7-yloxy)butanoate Scheme 2B

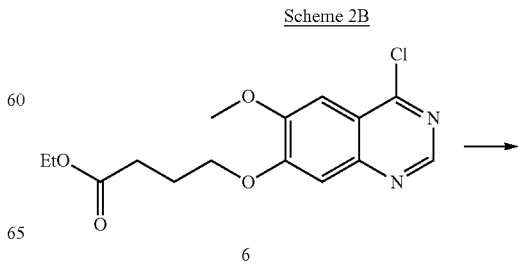

-continued

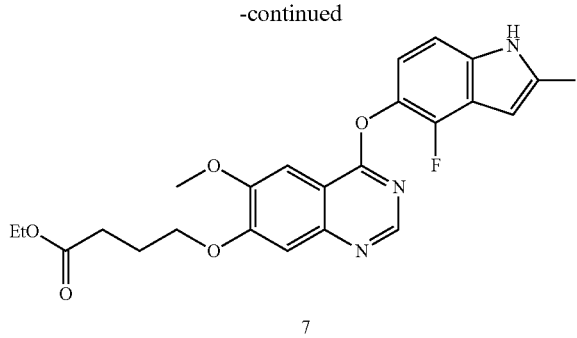

7

To a solution of Compound 6 (5.0 g, 15.39 mmol) and 4-fluoro-2-methyl-1H-indol-5-ol (3.56 g, 21.55 mmol) in acetonitrile (50 mL) was added cesium carbonate (15.05 g, 46.18 mmol). The reaction mixture was stirred at 50° C. for 2 h. TLC showed that no starting material remained. The inorganic material was removed by filtration and the filtrate was concentrated to give a brown solid. The solid was dissolved in ethyl acetate (100 mL) and washed with water (100 mL×2). The organic phase was concentrated and the residue was purified by silica column (gradient of hexane: ethyl acetate 5:1 to 1:2) to give Compound 7 (5.90 g) as a purple solid.

Compound 8: 4-(4-(4-Fluoro-2-methyl-1H-indol-5-yloxy)-6-methoxyquinazolin-7-yloxy)butanoic acid Scheme 2C

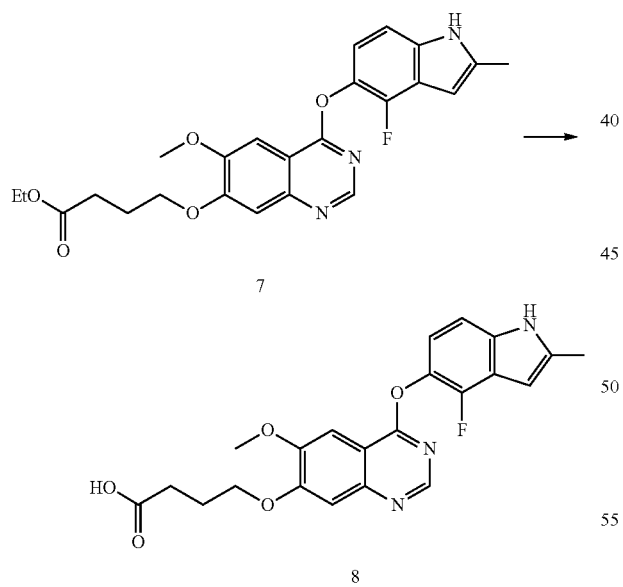

To a solution of Compound 7 (5.90 g, 10.12 mmol) in tetrahydrofuran (250 mL) was added aqueous lithium hydroxide solution (1N, 50.60 mL) dropwise. The reaction mixture was stirred overnight at room temperature. The reaction mixture was neutralized with hydrochloride acid (1N, aqueous solution) and concentrated to dryness to give crude Compound 8 (8.0 g) as a brown solid. The crude product was used in the next step without purification.

Compound 9: 4-(4-(4-Fluoro-2-methyl-1H-indol-5-yloxy)-6-methoxyquinazolin-7-yloxy)-1-(2-oxa-7-azaspiro[3.5]nonanyl)butan-1-one Scheme 2D

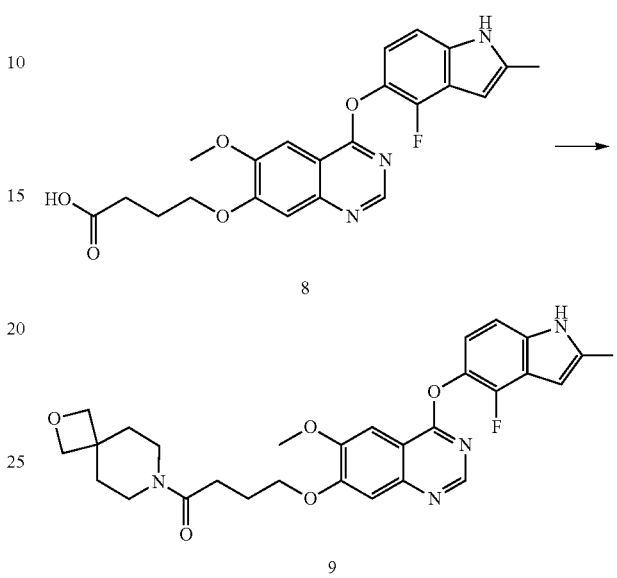

To a solution of Compound 8 (9.8 g, crude, containing lithium chloride) in N,N-dimethylformamide (100 mL) was added hydroxybenzotriazole (6.22 g, 46.07 mmol), 2-oxa-7-azaspiro[3.5]nonan hemioxalate (4.39 g, 34.56 mmol), N,N-diisopropylethylamine (8.93 g, 69.11 mmol) and 1-ethyl-3-(3-dimethylaminopropyl)carbodiimide hydrochloride (8.83 g, 46.07 mmol) sequentially. The reaction mixture was stirred overnight at room temperature and then poured into water (800 mL). Gray solid formed was collected by filtration. This solid was purified by flash chromatography (gradient from dichloromethane to dichloromethane:methanol 10:1) to give Compound 9 (5.20 g) as an off-white solid. m/z 535.3 (M+H, 100%) (positive ionization mode). $^1$H-NMR (CDCl$_3$, 400 MHz): δ 1.83 (4H, m); 2.27 (2H, m); 2.30 (3H, s); 2.46 (2H, t); 3.41 (2H, t); 3.42 (2H, t); 4.05 (3H, s); 4.27 (2H, t); 4.46 (4H, q); 6.34 (1H, q); 7.0 (1H, dd); 7.10 (1H, d); 7.34 (1H, s); 7.63 (1H, s); 8.17 (1H, s); 8.60 (1H, s).

Example 3

Synthesis of Compound 13

Scheme 3

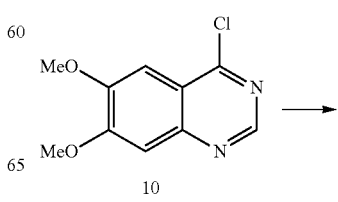

119

-continued

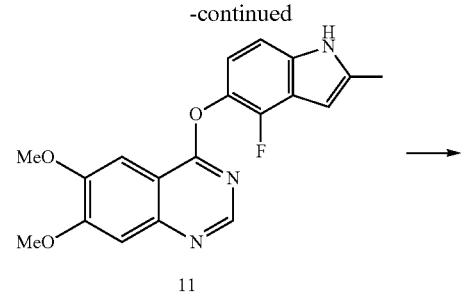

11

12

13

Compound 1: 4-(4-Fluoro-2-methyl-1H-indol-5-yloxy)-6,7-dimethoxyquinazoline

A solution of Compound 10 (739 mg, 3.3 mmol), 4-Fluoro-2-methyl-1H-indol-5-ol (530 mg, 3.3 mmol), and potassium carbonate (920 mg, 6.7 mmol) in dry dimethyl formamide (10 mL) was heated to 100° C. and stirred for 24 hours. The solution was cooled to room temperature and the solvent evaporated by rotary evaporator. Remaining residue was co-evaporated with methanol (20 mL) and dichloromethane/methanol (50 mL). The product residue was precipitated from water (20 mL) and filtered. Solids were washed with water (20 mL), hexanes (20 mL), and diethyl ether (20 mL). Product was dried under high vacuum to give 910 mg of Compound 11 (yield=78%) as a brown powder.

120

Compound 12: 4-Nitrophenyl 5-(6,7-dimethoxyquinazolin-4-yloxy)-4-fluoro-2-methyl-1H-indole-1-carboxylate A solution of Compound 11 (300 mg, 0.85 mmol) in dry THF was sparged with $N_2$, then NaH (68 mg of 60% dispersion, 1.7 mmol) was added in a single portion. While still sparging with $N_2$, 4-nitrophenyl chloroformate (341 mg, 1.7 mmol) was added and the reaction stirred at room temperature for 1 hour. Solvent was evaporated by rotary evaporator and the product precipitated from ethyl acetate/diethyl ether and filtered. The crude solid was washed with methanol (20 mL) to yield Compound 12 as crude yellow solid, which was taken directly to the next reaction.

Compound 13: 5-(6,7-Dimethoxyquinazolin-4-yloxy)-4-fluoro-2-methyl-N-propyl-1H-indole-1-carboxamide n-Propylamine (210 µL, 2.55 mmol) was added to a solution of Compound 12 in dry N,N-dimethylformamide and the reaction stirred for 40 minutes. The solvent was removed by rotary evaporator and the crude residue suspended in saturated aqueous $NaHCO_3$. Precipitate was filtered and washed with additional $NaHCO_3$ (20 mL×2) and diethyl ether (20 mL). Solids were dissolved in a minimal amount of methylene chloride and precipitated from diethyl ether. Precipitate was filtered and purified by reverse phase HPLC to give 27 mg of Compound 13 (two-step yield=7%) as a tan solid. m/z 439.2 (M+H, 100%) (positive ionization mode). $^1$H-NMR (CDCl$_3$, 400 MHz): δ 1.06 (3H, t); 1.74 (2H, m); 2.60 (3H, s); 4.08 (6H, d); 5.69 (1H, t); 6.47 (1H, s); 7.12 (1H, dd); 7.35 (1H, s); 7.48 (1H, d); 7.63 (1H, s); 8.61 (1H, s).

Example 4

Synthesis of Compounds 14-18

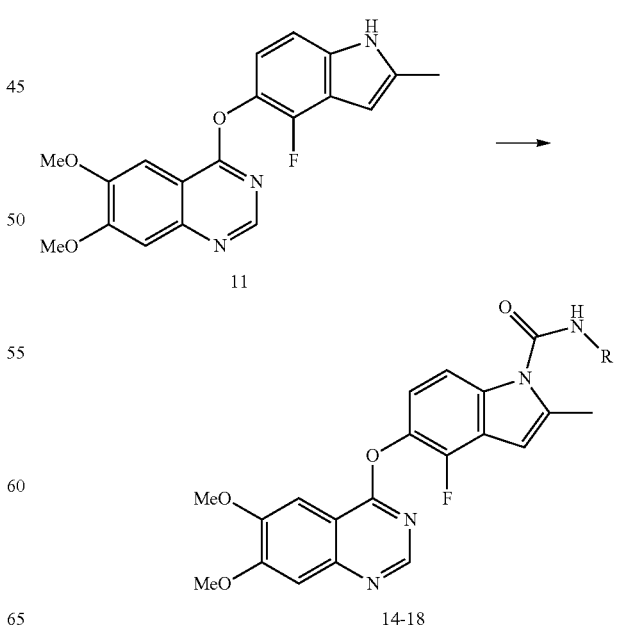

11

14-18

General Procedure: Compound 11 (300 mg, 0.85 mmol) was dissolved in dry N,N-dimethylformamide (5 mL) and sparged with $N_2$. NaH (60% dispersion in mineral oil, 68 mg, 1.7 mmol) was added, followed by isocyanate (1.7 mmol). Reaction was heated to 50° C. and stirred overnight. Solvent was evaporated by rotary evaporator and co-evaporated with dichloromethane (20 mL). Crude product was precipitated from diethyl ether or hexane/dicholormethane and filtered. The crude material was purified by preparative HPLC using VARIAN PREPSTAR with water-acetonitrile solvent system each containing 0.1% formic acid as modifier and "LOAD & LOCK" 50×250 mm column with C18 reverse phase silica gel. The obtained solution of the product was converted to free base using dichloromethane with 10% methanol and aqueous sodium bicarbonate, dried with sodium sulfate, and concentrated.

Compound 15

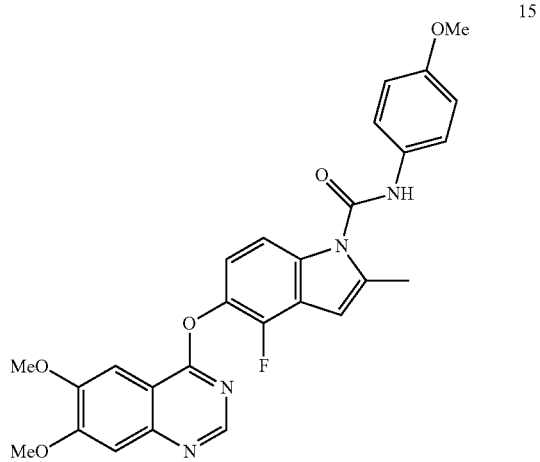

5-(6,7-Dimethoxyquinazolin-4-yloxy)-4-fluoro-N-(4-methoxyphenyl)-2-methyl-1H-indole-1-carboxamide. 52 mg (0.1 mmol, yield=12%) tan solid. MS: m/z 503.2 [M+H]$^+$. $^1$H-NMR (DMSO-d6, 400 MHz): δ 2.54 (3H, s); 3.67 (3H, s); 3.97 (6H, s); 6.81 (2H, d); 7.13 (1H, m); 7.24 (1H, d); 7.38 (1H, s); 7.56 (3H, m); 8.49 (1H, s); 9.71 (1H, s).

Compound 14

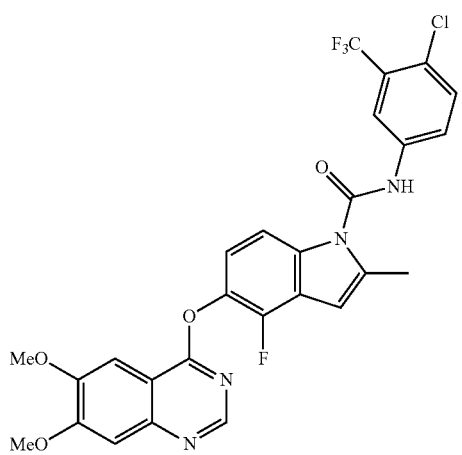

Compound 16

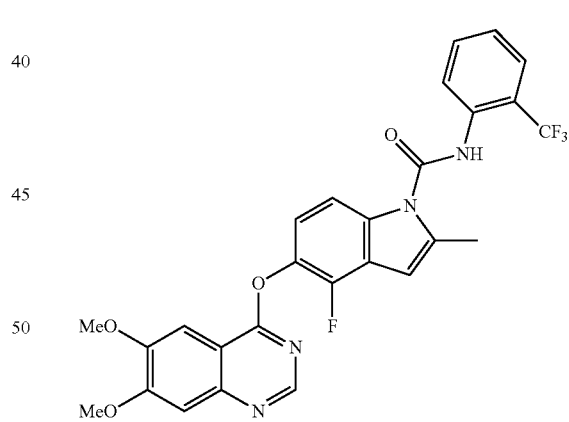

5-(6,7-Dimethoxyquinazolin-4-yloxy)-N-(4-chloro-3-(trifluoromethyl)phenyl)-4-fluoro-2-methyl-1H-indole-1-carboxamide. 69 mg (0.12 mmol, yield=14%) tan solid. MS: m/z 575.1 [M+H]$^+$. $^1$H-NMR (DMSO-d6, 400 MHz): δ 2.56 (3H, s); 3.96 (6H, s); 7.15 (1H, t); 7.27 (1H, d); 7.37 (1H, s); 7.55 (1H, s); 7.59 (1H, d); 7.88 (1H, dd); 8.28 (1H, m); 8.48 (1H, s); 10.31 (1H, s).

5-(6,7-Dimethoxyquinazolin-4-yloxy)-4-fluoro-N-(2-(trifluoromethyl)phenyl)-2-methyl-1H-indole-1-carboxamide. 31 mg (0.06 mmol, yield=7%) off-white powder. MS: m/z 541.1 [M+H]$^+$. $^1$H-NMR (DMSO-d6, 400 MHz): δ 2.62 (3H, s); 3.99 (6H, d); 7.18 (1H, t); 7.29 (1H, d); 7.41 (2H, s); 7.60 (1H, s); 7.67 (2H, d); 7.71 (1H, d); 8.53 (1H, s); 9.27 (1H, d).

Compound 17

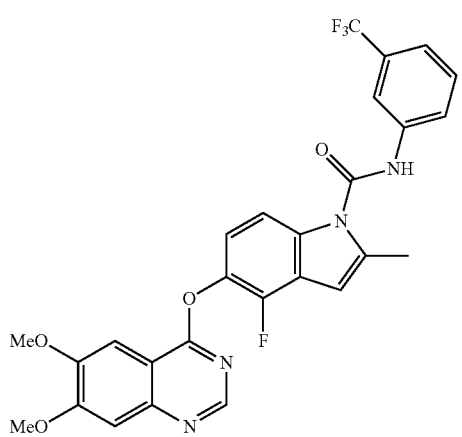

5-(6,7-Dimethoxyquinazolin-4-yloxy)-4-fluoro-N-(3-(trifluoromethyl)phenyl)-2-methyl-1H-indole-1-carboxamide. 93 mg (0.17 mmol, yield=20%) tan powder. MS: m/z 541.2 [M+H]$^+$. $^1$H-NMR (DMSO-d6, 400 MHz): δ 2.59 (3H, s); 3.99 (6H, s); 7.18 (1H, t); 7.29 (1H, d); 7.35 (1H, d); 7.40 (1H, s); 7.51 (1H, t); 7.58 (1H, s); 7.85 (1H, d); 8.21 (1H, s); 8.51 (1H, s); 10.24 (1H, s).

Compound 18

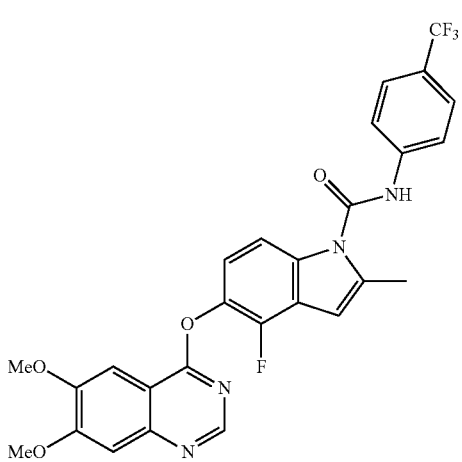

5-(6,7-Dimethoxyquinazolin-4-yloxy)-4-fluoro-N-(4-(trifluoromethyl)phenyl)-2-methyl-1H-indole-1-carboxamide. 62 mg (0.11 mmol, Y=14%) tan powder. MS: m/z 541.2 [M+H]$^+$. $^1$H-NMR (DMSO-d6, 400 MHz): δ 2.59 (3H, s); 3.99 (6H, s); 7.18 (1H, t); 7.30 (1H, d); 7.40 (1H, s); 7.58 (1H, s); 7.63 (1H, d); 7.88 (2H, d); 8.51 (1H, s); 10.27 (1H, s).

Example 5

VEGFR2 Binding Assay

A competition binding assay (DISCOVERX KINOMES-CAN™) was used to measure the ability of a compound to compete for binding of an immobilized adenosine triphosphate (ATP) site directed ligand using a DNA-tagged vascular endothelial growth receptor 2 (VEGFR2) as the target. The ability of the test compound to compete with the immobilized ligand was measured using quantitative polymerase chain reaction (qPCR) of the DNA tag (Fabian, M. A. et al., 23 Nature Biotechnology 329-336 (2005); Karaman, M. W. et al., 26 Nature Biotechnology 127-132 (2008)).

A VEGFR2 tagged T7 phage strain was prepared in an Escherichia coli (E. coli) derived from the BL21 strain. The E. coli were grown to log-phase, infected with VEGFR2 tagged T7 phage and then incubated with shaking at 32° C. until lysis. The lysate containing the kinase was then centrifuged and filtered to remove cell debris. Affinity resin for the VEGFR2 assay was prepared by treating Streptavidin-coated magnetic beads with a biotinylated small molecule ligand for 30 minutes at room temperature. The beads were blocked with excess biotin and then washed with blocking buffer (SEABLOCK (PIERCE), 1% bovine serum albumin, 0.17% phosphate buffered saline, 0.05% TWEEN 20, 6 mM dithiothreitol). The binding reaction was initiated by combining in a well of a polystyrene 96-well plate, DNA tagged VEGFR2, liganded affinity beads and the serial diluted test compound in 1× binding buffer (20% SEABLOCK, 0.17× phosphate buffered saline, 0.05% TWEEN 20, 6 mM dithiothreitol) in a final volume of 0.135 ml. The assay plates were incubated at room temperature with shaking for 1 hour and then the beads were washed with wash buffer (1× phosphate buffered saline, 0.05% TWEEN 20). The beads were re-suspended in elution buffer (1× phosphate buffered saline, 0.05% TWEEN 20, 0.05 µM non-biotinylated affinity ligand) and incubated at room temperature with shaking for 30 minutes. The VEGFR2 concentration in the eluate was measured using qPCR.

An 11-point dose response curve of 3-fold serial diluted test compound starting at 1 µM was used to determine the VEGFR2 binding constant ($K_d$). The compounds were prepared in 100% DMSO at 100× the final test concentration and the diluted to 1× in the assay for final DMSO concentration of 1%. Binding constants were calculated with standard dose-response curve using the Hill equation with Hill slope set to −1. Curves were fit using a non-linear least square fit with the Levenberg-Marquardt algorithm.

TABLE 3

$K_d$ values of selected compounds.

| Compound ID | $K_d$ |
| --- | --- |
| 4 | 0.33 |
| 9 | 0.73 |
| 14 | >1000 |
| 15 | 380 |
| 16 | 56 |
| 17 | >1000 |
| 18 | >1000 |

Example 6

Novel Compounds Formulated as Mucus Penetrating Particles (MPP)

The compounds of the present invention synthesized in accordance with the preceding Examples were formulated as mucus penetrating particles (MPP). Specifically, Compound 4 of Example 1, Compound 9 of Example 2, and Compound 13 of Example 3 were each milled in the presence of PLURONIC F127 (F127) to determine whether F127 1) aids particle size reduction to several hundreds of nanometers and 2) physically (non-covalently) coats the surface of generated nanoparticles with a mucoinert coating that would minimize particle interactions with mucus constituents and prevent mucus adhesion.

A milling procedure was employed in which an aqueous dispersion containing coarse drug particles and PLURONIC F127 (F127) was milled with grinding medium until particle size was reduced below 400 nm as measured by dynamic light scattering. Table 4 lists the size of particles and polydispersity index (a measure of the width of the particle size distribution) generated using this technique. In this example suspensions were buffered using DPBS (Dulbecco's Phosphate-Buffered Saline) which yields a suspension that is both isotonic and has a physiologically relevant pH.

TABLE 4

Particle size for compounds formulated as MPP

| Compound ID | Particle Size (nm) | Polydispersity Index (PDI) |
|---|---|---|
| Compound 4 | 270 | 0.142 |
| Compound 9 | 195 | 0.176 |
| Compound 13 | 165 | 0.227 |

In order to determine whether the generated nanoparticles have reduced interactions with mucins and are therefore able to move within mucus without becoming trapped, particles were incubated with human cervicovaginal mucus (CVM) and observed via dark field microscopy. In a typical experiment, ≤1 µL of the nanoparticle suspension was added to 20 µl of CVM. Observations were made in a minimum of three distinct and randomly selected areas of the CVM sample. Control particles with known behavior were used to qualify the CVM sample as appropriate for the assay. For all compounds listed in Table 4, mobility in mucus was observed and therefore the nanoparticles were deemed to be effective MPP.

Example 7

Back of the Eye Drug Exposure from Topical Installation of Novel Compound MPP

A pharmacokinetic (PK) study of Compound 4 formulated as MPP in accordance with Example 6 was performed in order to demonstrate that topical installation of MPP formulations of these compounds results in drug exposure at the back of the eye. The study design is shown in Table 5. Dutch-belted rabbits were used in these studies.

TABLE 5

Study design for PK evaluation of novel compound MPP

| Group | Test Article | Number of Animals (n/time point) | Dose Volume | Frequency/ Duration | Terminal Timepoints (hours) |
|---|---|---|---|---|---|
| 1 | MPP, 0.5% | 4 | 50 µL | BID 5 days | 0.5 |
| 2 | MPP, 0.5% | 4 | 50 µL | BID 5 days | 1 |
| 3 | MPP, 0.5% | 4 | 50 µL | BID 5 days | 2 |
| 4 | MPP, 0.5% | 4 | 50 µL | BID 5 days | 4 |
| 5 | MPP, 0.5% | 6 | 50 µL | BID 5 days | 8 |
| 6 | MPP, 0.5% | 6 | 50 µL | BID 5 days | 12 |

BID = twice a day

The resulting drug exposure in the back of the eye is shown in Table 5.

TABLE 6

$C_{max}$ and $AUC_{0-last}$ drug concentrations for compounds tested in PK

| Compound ID | $C_{max}$ Retina (nM) | $C_{max}$ Choroid (nM) | $AUC_{0-last}$ Retina (nM * h) | $AUC_{0-last}$ Choroid (nM * h) |
|---|---|---|---|---|
| Compound 4 | 193 | 3900 | 1150 | 37200 |

The portion of the retina and choroid collected and analyzed was an 8 mm round punch where the macula is located in humans. These results demonstrate that topical installation of novel compound MPP result in drug exposure in the retina and choroid in vivo.

Draize-Ocular Irritation assessments were also performed during this study and no irritation was seen.

Example 8

Formulation of Compound 4

In this example, Compound 4 was formulated as a solution for topical ocular administration. Solutions of Compound 4 were formulated at a range of concentrations. Briefly, Compound 4 was first completely solubilized using an acidic solution (0.1N HCl) at a high concentration of ~5% (w/v). The final formulation was diluted to 0.5, 0.1, or 0.05% (w/v) Compound 4 into 20 mM Citrate buffered solution containing TWEEN 80 as described in Table 7. Following dilution, the pH's of the formulations were estimated to be ~5.5-6.5, using a universal pH indicator solution (Ricca).

TABLE 7

Composition of solutions of Compound 4

| API (% w/v) | TWEEN 80 (% w/v) |
|---|---|
| 0.5 | 4 |
| 0.1 | 0.1 |
| 0.05 | 0.05 |

The values listed are final concentration of each component in the formulation.

Solution physical and chemical stability at ambient temperature (20-25° C.) were evaluated 10-21 days after initial formulation ($t_{final}$). Physical stability was assessed visually. No precipitation or sedimentation in any samples was observed. All formulations maintained good chemical stability, within 10% of target concentration at $t_{final}$. The API purity as defined by % peak area for all formulations were also high, at >99% (Table 8). Formulations pH's were also measured using a universal pH indicator solution (RICCA) and confirmed be similar to those at initial time of formulation.

TABLE 8

Stability of Compound 4 (as evaluated by API concentration and purity over time)

| Target API % (w/v) | TWEEN 80 % (w/v) | $t_{final}$ (days) | API % (w/v) at t = $t_{final}$ | API % peak area* at t = $t_{final}$ |
|---|---|---|---|---|
| 0.50 | 4 | 10 | 0.51 | 99.27 |
| 0.10 | 0.1 | 21 | 0.11 | 99.47 |
| 0.05 | 0.05 | 13 | 0.05 | 99.45 |

*% peak area: the area under the signal peak that is attributed to the API as a percentage of all peaks reported by in the sample by HPLC.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A pharmaceutical composition suitable for delivery to the eye, comprising a pharmaceutically acceptable carrier and a compound of Formula (I):

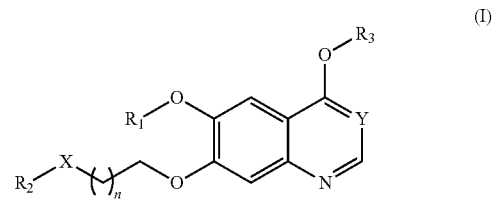

or a pharmaceutically acceptable salt thereof, wherein:
$R_1$ is H or optionally substituted $C_{1-6}$ alkyl;
$R_2$ is optionally substituted bicyclic heterocyclyl having 1 or 2 heteroatoms;
X is a bond, —O—, or —C(=O)—;
Y is N;
$R_3$ is optionally substituted heteroaryl; and
n is 0, 1, 2, 3, or 4.

2. The pharmaceutical composition of claim 1, wherein the compound of Formula (I) is a compound of Formula (II):

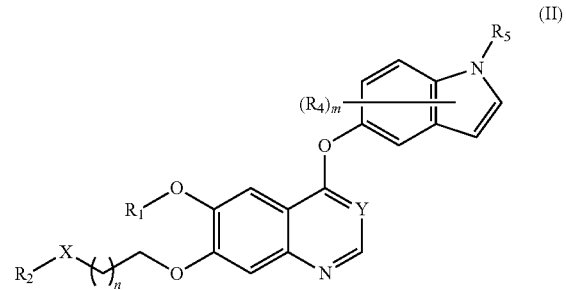

or a pharmaceutically acceptable salt thereof, wherein:
each instance of $R_4$ is independently H, optionally substituted $C_{1-6}$ alkyl, F, Cl, Br, I, CN, OH, or alkoxy;
$R_5$ is H or a nitrogen protecting group; and
m is 0, 1, 2, 3, 4, or 5.

3. The pharmaceutical composition of claim 2, wherein $R_4$ is H.

4. The pharmaceutical composition of claim 2, wherein $R_4$ is F.

5. The pharmaceutical composition of claim 2, wherein $R_4$ is $CH_3$.

6. The pharmaceutical composition of claim 1, wherein the compound of Formula (I) is a compound of Formula (III):

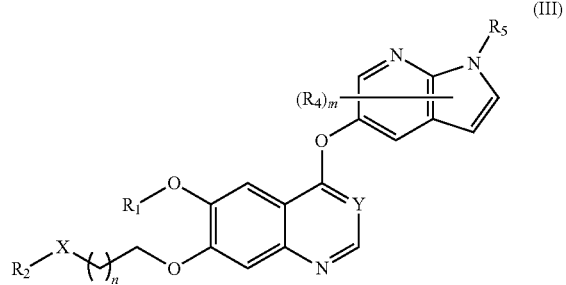

or a pharmaceutically acceptable salt thereof, wherein:
each instance of $R_4$ is independently H, optionally substituted $C_{1-6}$ alkyl, F, Cl, Br, I, CN, OH, or alkoxy;
$R_5$ is H or a nitrogen protecting group; and
m is 0, 1, 2, 3, or 4.

7. The pharmaceutical composition of claim 6, wherein $R_4$ is H.

8. The pharmaceutical composition of claim 6, wherein $R_4$ is F.

9. The pharmaceutical composition of claim 6, wherein $R_4$ is $CH_3$.

10. The pharmaceutical composition of claim 6, wherein $R_5$ is H.

11. The pharmaceutical composition of claim 1, wherein $R_1$ is $CH_3$.

12. The pharmaceutical composition of claim 1, wherein $R_2$ is

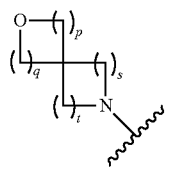

wherein p, q, s, and t are independently 0, 1, 2, 3, or 4.

13. The pharmaceutical composition of claim 12, wherein $R_2$ is

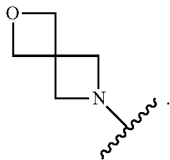

14. The pharmaceutical composition of claim 12, wherein $R_2$ is

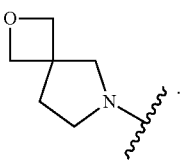

15. The pharmaceutical composition of claim 12, wherein $R_2$ is

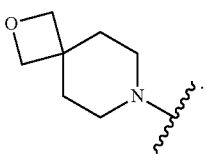 [SMILES: *N1CCC2(CC1)COC2]

16. The pharmaceutical composition of claim 1, wherein X is a bond.

17. The pharmaceutical composition of claim 1, wherein X is —C(=O)—.

18. The pharmaceutical composition of claim 1, wherein n is 1.

19. The pharmaceutical composition of claim 1, wherein n is 2.

20. The pharmaceutical composition of claim 1, wherein the compound of Formula (I) is:

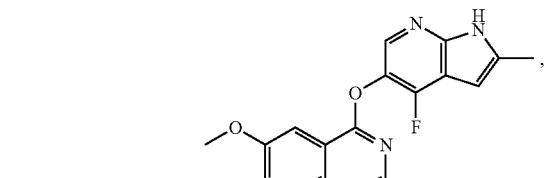,

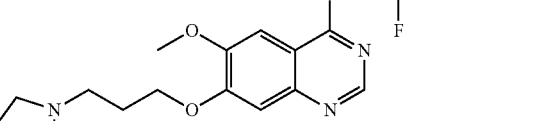,

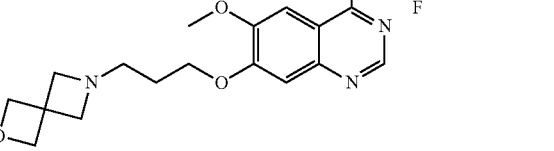,

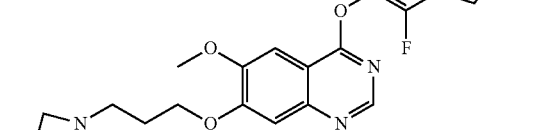,

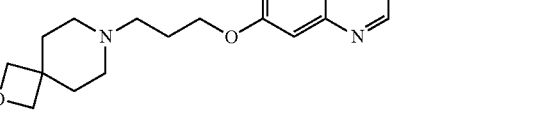,

131
-continued
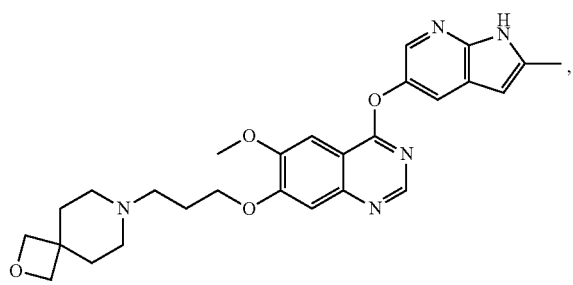 [SMILES: COc1cc2c(Oc3ccc4[nH]c(C)cc4c3F)ncnc2cc1OCCCN1CCC2(CC1)COC2]
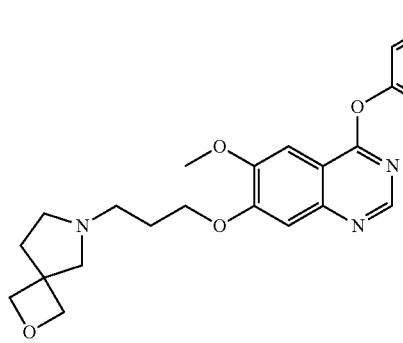
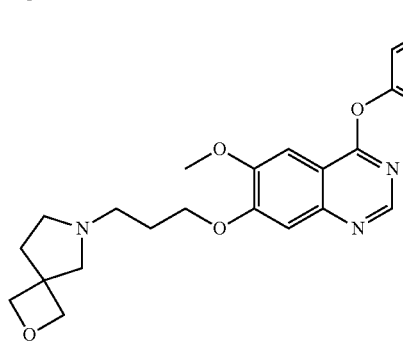
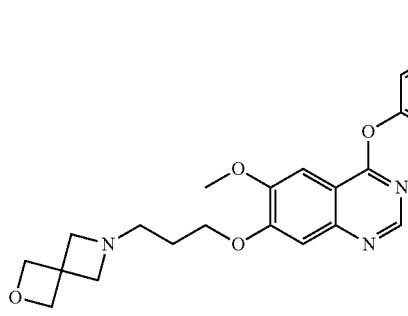
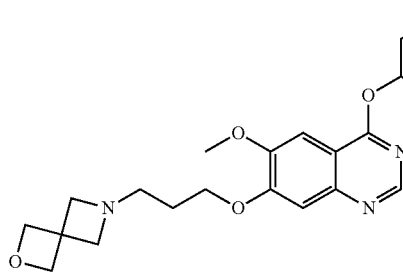
132
-continued
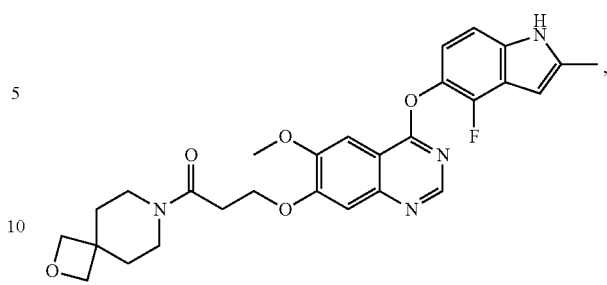
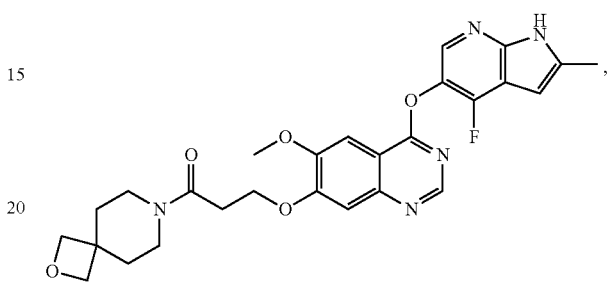
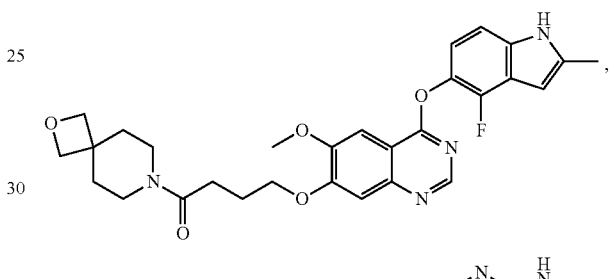
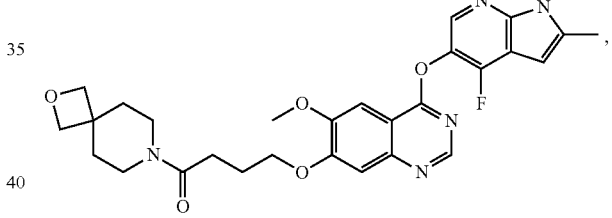
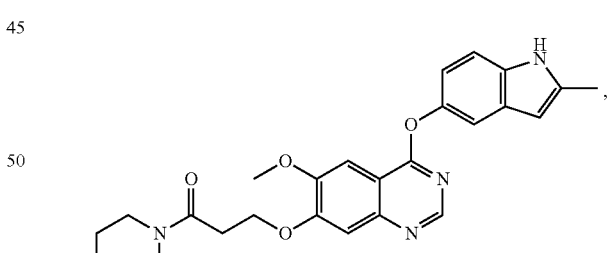
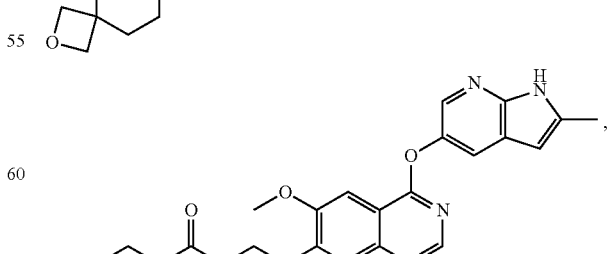
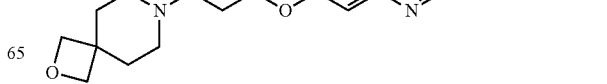

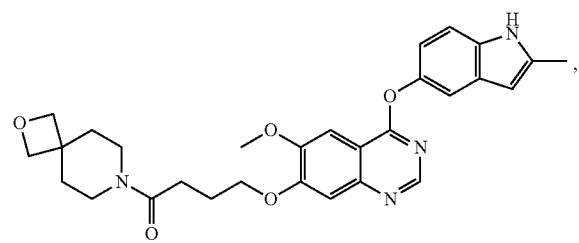
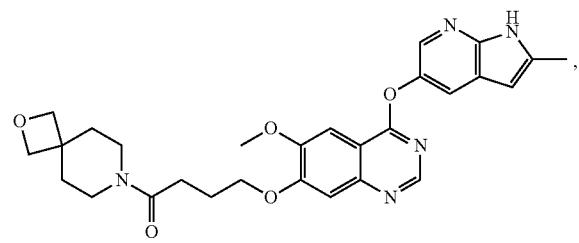
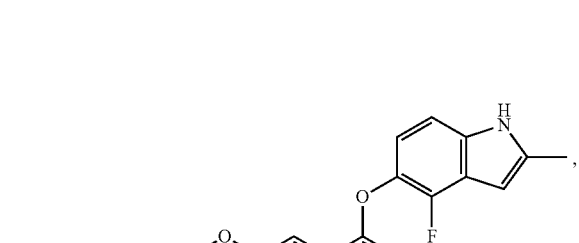
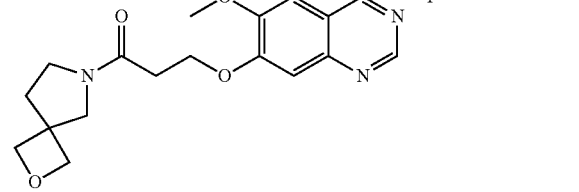
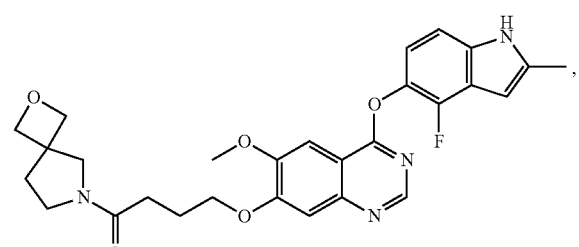
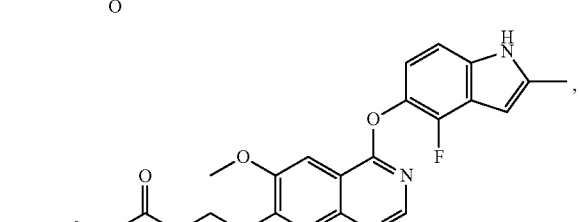
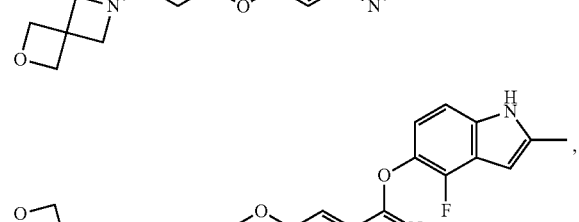
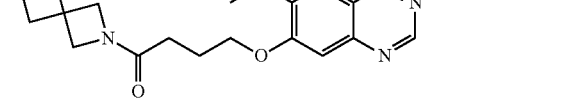
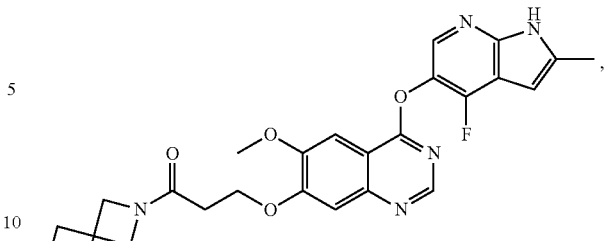
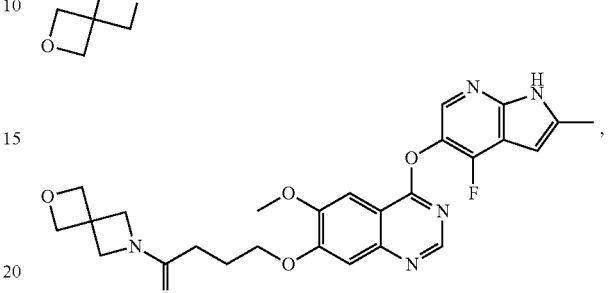
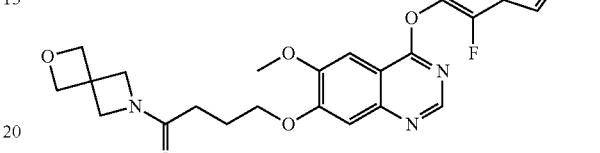
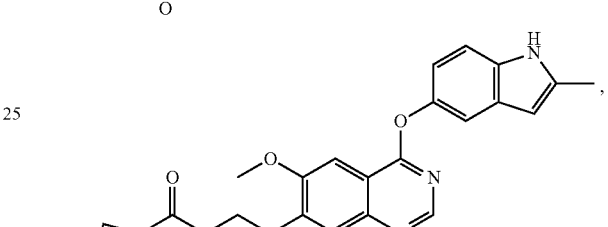
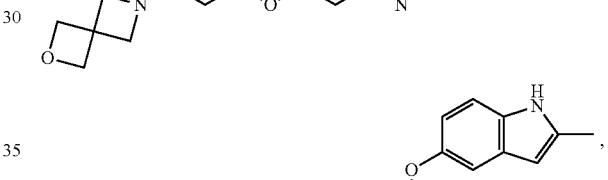
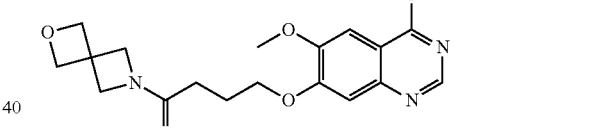
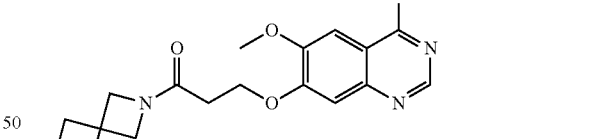
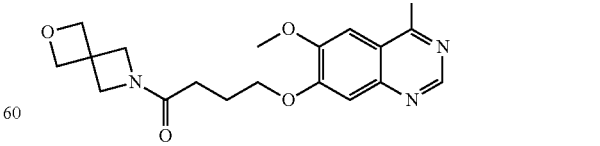
or a pharmaceutically acceptable salt thereof.
21. A method of treating an ocular disease, comprising administering the pharmaceutical composition of claim 1 to a subject in need thereof.

22. The method of claim 21, wherein the ocular disease is a retinopathy, age-related macular degeneration, corneal neovascularization, diabetic macular edema, retinal vein occlusion, or glaucoma.

23. A pharmaceutical composition for administration to an eye, comprising:

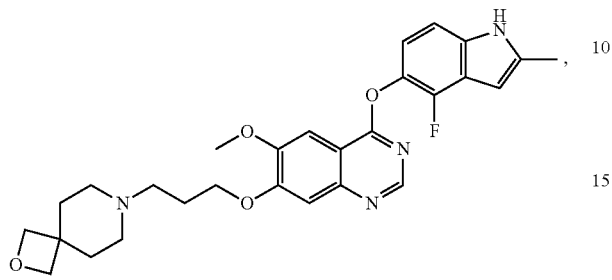

or a pharmaceutically acceptable salt thereof.

24. A method of treating an ocular disease, comprising administering the pharmaceutical composition of claim 23 to a subject in need thereof.

25. The method of claim 24, wherein the ocular disease is a retinopathy, age-related macular degeneration, corneal neovascularization, diabetic macular edema, retinal vein occlusion, or glaucoma.

* * * * *